United States Patent
Rao-Naik et al.

(10) Patent No.: US 8,097,703 B2
(45) Date of Patent: Jan. 17, 2012

(54) CD19 ANTIBODIES AND THEIR USES

(75) Inventors: Chetana Rao-Naik, Walnut Creek, CA (US); David John King, Belmont, CA (US); Jie Liu, Palo Alto, CA (US); Haichun Huang, Fremont, CA (US); David B. Passmore, San Carlos, CA (US); Alasdair Fraser Bell, Mountain View, CA (US); Josephine M. Cardarelli, San Carlos, CA (US); Chin Pan, Los Altos, CA (US); To Uyen Thi Do, Sacramento, CA (US); Sharline Chen, Sunnyvale, CA (US); Dawn M. Tanamachi, Milpitas, CA (US)

(73) Assignee: Medarex, Inc., Princeton, NJ (US)

( * ) Notice: Subject to any disclaimer, the term of this patent is extended or adjusted under 35 U.S.C. 154(b) by 647 days.

(21) Appl. No.: 11/917,750

(22) PCT Filed: Jun. 20, 2006

(86) PCT No.: PCT/US2006/024183
§ 371 (c)(1),
(2), (4) Date: Jul. 21, 2008

(87) PCT Pub. No.: WO2007/002223
PCT Pub. Date: Jan. 4, 2007

(65) Prior Publication Data
US 2009/0142349 A1    Jun. 4, 2009

Related U.S. Application Data

(60) Provisional application No. 60/692,531, filed on Jun. 20, 2005, provisional application No. 60/748,956, filed on Dec. 8, 2005, provisional application No. 60/804,083, filed on Jun. 6, 2006.

(51) Int. Cl.
*C07K 16/00* (2006.01)
*C07K 17/00* (2006.01)
*C12P 21/08* (2006.01)
*C07K 14/00* (2006.01)

(52) U.S. Cl. ............... 530/387.1; 530/387.3; 530/387.7; 530/387.9; 530/388.1; 530/388.15; 530/388.22; 530/388.7; 530/388.73; 530/391.1

(58) Field of Classification Search .......................... None
See application file for complete search history.

(56) References Cited

U.S. PATENT DOCUMENTS

| | | | |
|---|---|---|---|
| 6,653,104 B2 | 11/2003 | Goldenberg | |
| 7,109,304 B2 | 9/2006 | Hansen et al. | |
| 2002/0062009 A1 | 5/2002 | Taylor | |
| 2003/0157109 A1 | 8/2003 | Corvalan et al. | |
| 2003/0194403 A1 | 10/2003 | van de Winkel et al. | |
| 2004/0110704 A1 * | 6/2004 | Yamane et al. | 514/44 |
| 2004/0170630 A1 | 9/2004 | Huang et al. | |
| 2004/0219156 A1 | 11/2004 | Goldenberg et al. | |
| 2004/0258678 A1 | 12/2004 | Bodary et al. | |
| 2005/0070693 A1 | 3/2005 | Hansen et al. | |
| 2005/0226876 A1 | 10/2005 | Graus et al. | |
| 2006/0029601 A1 | 2/2006 | Carderelli et al. | |
| 2006/0263357 A1 | 11/2006 | Tedder et al. | |
| 2007/0003544 A1 | 1/2007 | Hanna | |
| 2007/0166306 A1 | 7/2007 | Fey et al. | |
| 2007/0264257 A1 | 11/2007 | Dunussi-Joannopoulos et al. | |

FOREIGN PATENT DOCUMENTS

| | | |
|---|---|---|
| DE | 199 30 433 | 1/2001 |
| WO | WO 96/36360 | 11/1996 |
| WO | WO 99/54440 | 10/1999 |
| WO | WO 00/67796 | 11/2000 |
| WO | WO0067795 | 11/2000 |
| WO | WO 02/100348 | 12/2002 |
| WO | WO 2005/012493 | 2/2005 |
| WO | WO 2006/121852 | 11/2006 |
| WO | WO 2007/085470 | 8/2007 |

OTHER PUBLICATIONS

Rudikoff et al. PNAS 1982 vol. 79, pp. 1979-1983.*
Rader et al. PNAS 1998. 95:8910-8915.*
Fishwild et al. (Nature Biotech. 1996, 14:845-851.*
Beiboer et al. J. Mol. Biol. 2000, 296:833-849.*
Ditzel et al. The Journal of Immunology. 1996, 157:739-749.*
Barbas et al. PNAS 1995, 92:2529-2533.*
Barbas et al. J. Am. Chem. Soc. 1994, 116:2161-2162.*
Klimka et al. British Journal of Cancer 2000, 82;2:252-260.*
Raji ATCC Catalog page. Sep. 7, 2011, pp. 1-2.*
Daudi ATCC Catalog page. Sep. 7, 2011, pp. 1-3.*
U.S. Appl. No. 12/519,149, filed Dec. 15, 2009, King et al.
Roguska M A et al.; "A Comparison of Two Murine Monoclonal Antibodies Humanized by CDR-Grafting and Variable Domain Resurfacing"; Protein Engineering, Oxford University Press, Surrey, GB; vol. 9, No. 10, 1996, pp. 895-904.

* cited by examiner

*Primary Examiner* — Chun Dahle
(74) *Attorney, Agent, or Firm* — Ashton J. Delauney

(57) ABSTRACT

The present disclosure provides isolated monoclonal antibodies, particularly human monoclonal antibodies that specifically bind to CD19 with high affinity. Nucleic acid molecules encoding such CD19 antibodies, expression vectors, host cells and methods for expressing the CD19 antibodies are also provided. Immunoconjugates, bispecific molecules and pharmaceutical compositions comprising the CD19 antibodies are also provided. Methods for detecting CD19, as well as methods for treating various B cell malignancies, including non-Hodgkin's lymphoma, are disclosed.

20 Claims, 50 Drawing Sheets

Anti-CD19 21D4 and 21D4a VH

V segment:    5-51
    D segment:    3-10
    J segment:    JH4b

```
        E   V   Q   L   V   Q   S   G   A   E   V   K   K   P   G   E   S   L
1       GAG GTG CAG CTG GTG CAG TCT GGA GCA GAG GTG AAA AAG CCC GGG GAG TCT CTG
                                                                    CDR1
                                                              ~~~~~~~~~~~~~~~~~
        K   I   S   C   K   G   S   G   Y   S   F   S   S   S   W   I   G   W
55      AAG ATC TCC TGT AAG GGT TCT GGA TAC AGC TTT AGC AGC AGC TGG ATC GGC TGG
                                                                    CDR2
                                                              ~~~~~~~~~~~~~~~~~
        V   R   Q   M   P   G   K   G   L   E   W   M   G   I   I   Y   P   D
109     GTG CGC CAG ATG CCC GGG AAA GGC CTG GAG TGG ATG GGG ATC ATC TAT CCT GAT
                        CDR2
        ~~~~~~~~~~~~~~~~~~~~~~~~~~~~~~~~~~~~~~~~~~~~~~~~~~~~
        D   S   D   T   R   Y   S   P   S   F   Q   G   Q   V   T   I   S   A
163     GAC TCT GAT ACC AGA TAC AGT CCG TCC TTC CAA GGC CAG GTC ACC ATC TCA GCC

D   K   S   I   R   T   A   Y   L   Q   W   S   S   L   K   A   S   D
217     GAC AAG TCC ATC AGG ACC GCC TAC CTG CAG TGG AGC AGC CTG AAG GCC TCG GAC
                                                            CDR3
                                                  ~~~~~~~~~~~~~~~~~~~~~~~~~~~~~
        T   A   M   Y   Y   C   A   R   H   V   T   M   I   W   G   V   I   I
271     ACC GCC ATG TAT TAC TGT GCG AGA CAT GTT ACT ATG ATT TGG GGA GTT ATT ATT
        CDR3
        ~~~~~~~~
        D   F   W   G   Q   G   T   L   V   T   V   S   S
325     GAC TTC TGG GGC CAG GGA ACC CTG GTC ACC GTC TCC TCA
```

Figure 1A

Anti-CD19 21D4 VK

V segment: L18
J segment: JK2

```
         A   I   Q   L   T   Q   S   P   S   S   L   S   A   S   V   G   D   R
1        GCC ATC CAG TTG ACC CAG TCT CCA TCC TCC CTG TCT GCA TCT GTA GGA GAC AGA

CDR1
                                       ~~~~~~~~~~~~~~~~~~~~~~~~~~~~~~~~~~~~~~~~~
         V   T   I   T   C   R   A   S   Q   G   I   S   S   A   L   A   W   Y
55       GTC ACC ATC ACT TGC CGG GCA AGT CAG GGC ATT AGC AGT GCT TTA GCC TGG TAT

CDR2
                                                             ~~~~~~~~~~~~~~~~~~~~
         Q   Q   K   P   G   K   A   P   K   L   L   I   Y   D   A   S   S   L
109      CAG CAG AAA CCA GGG AAA GCT CCT AAG CTC CTG ATC TAT GAT GCC TCC AGT TTG

CDR2
         ~~~~~~~
         E   S   G   V   P   S   R   F   S   G   S   G   S   G   T   D   F   T
163      GAA AGT GGG GTC CCA TCA AGG TTC AGC GGC AGT GGA TCT GGG ACA GAT TTC ACT

CDR3
                                                                       ~~~~~~~~~
         L   T   I   S   S   L   Q   P   E   D   F   A   T   Y   Y   C   Q   Q
217      CTC ACC ATC AGC AGC CTG CAG CCT GAA GAT TTT GCA ACT TAT TAC TGT CAA CAG

CDR3
         ~~~~~~~~~~~~~~~~~~~~~~~~~~~
         F   N   S   Y   P   Y   T   F   G   Q   G   T   K   L   E   I   K
271      TTT AAT AGT TAC CCG TAC ACT TTT GGC CAG GGG ACC AAG CTG GAG ATC AAA
```

Figure 1B

Anti-CD19 21D4a VK

V segment:   L18
   J segment:   JK3

```
          A   I   Q   L   T   Q   S   P   S   S   L   S   A   S   V   G   D   R
  1      GCC ATC CAG TTG ACC CAG TCT CCA TCC TCC CTG TCT GCA TCT GTA GGA GAC AGA

CDR1
                                          ~~~~~~~~~~~~~~~~~~~~~~~~~~~~~~~~~~~~
          V   T   I   T   C   R   A   S   Q   G   I   S   S   A   L   A   W   Y
 55      GTC ACC ATC ACT TGC CGG GCA AGT CAG GGC ATT AGC AGT GCT TTA GCC TGG TAT

CDR2
                                                                    ~~~~~~~~~~~~~~~~~~~~
          Q   Q   K   P   G   K   A   P   K   L   L   I   Y   D   A   S   S   L
109      CAG CAG AAA CCA GGG AAA GCT CCT AAG CTC CTG ATC TAT GAT GCC TCC AGT TTG

CDR2
          ~~~~~~~~
          E   S   G   V   P   S   R   F   S   G   S   G   S   G   T   D   F   T
163      GAA AGT GGG GTC CCA TCA AGG TTC AGC GGC AGT GGA TCT GGG ACA GAT TTC ACT

CDR3
                                                                            ~~~~~~~~
          L   T   I   S   S   L   Q   P   E   D   F   A   T   Y   Y   C   Q   Q
217      CTC ACC ATC AGC AGC CTG CAG CCT GAA GAT TTT GCA ACT TAT TAC TGT CAA CAG

CDR3
          ~~~~~~~~~~~~~~~~~~~~~~~~~~~~
          F   N   S   Y   P   F   T   F   G   P   G   T   K   V   D   I   K
271      TTT AAT AGT TAC CCA TTC ACT TTC GGC CCT GGG ACC AAA GTG GAT ATC AAA
```

Figure 1C

Anti-CD19 47G4 VH

V segment: 1-69
D segment: 6-19
J segment: JH5b

```
         Q   V   Q   L   V   Q   S   G   A   E   V   K   K   P   G   S   S   V
1        CAG GTC CAG CTG GTG CAG TCT GGG GCT GAG GTG AAG AAG CCT GGG TCC TCG GTG

CDR1
                                                         ~~~~~~~~~~~~~~~~~~~~
         K   V   S   C   K   D   S   G   G   T   F   S   S   Y   A   I   S   W
55       AAG GTC TCC TGC AAG GAC TCT GGA GGC ACC TTC AGC AGC TAT GCT ATC AGC TGG

CDR2
                                                              ~~~~~~~~~~~~~~~~~
         V   R   Q   A   P   G   Q   G   L   E   W   M   G   G   I   I   P   I
109      GTG CGA CAG GCC CCT GGA CAA GGA CTT GAG TGG ATG GGA GGG ATC ATC CCT ATC

CDR2
         ~~~~~~~~~~~~~~~~~~~~~~~~~~~~~~~~~~~~~~~~~~~~
         F   G   T   T   N   Y   A   Q   Q   F   Q   G   R   V   T   I   T   A
163      TTT GGT ACA ACA AAC TAC GCA CAG CAG TTC CAG GGC AGA GTC ACG ATT ACC GCG

D   E   S   T   S   T   A   Y   M   E   L   S   S   L   R   S   E   D
217      GAC GAA TCC ACG AGC ACA GCC TAC ATG GAG CTG AGC AGT CTG AGA TCT GAG GAC

CDR3
                                              ~~~~~~~~~~~~~~~~~~~~~~~~~~~~~~~~~~~~
         T   A   V   Y   Y   C   A   R   E   A   V   A   A   D   W   L   D   P
271      ACG GCC GTG TAT TAC TGT GCG AGA GAA GCA GTA GCT GCG GAC TGG TTA GAC CCC

W   G   Q   G   T   L   V   T   V   S   S
325      TGG GGC CAG GGA ACC CTG GTC ACC GTC TCC TCA
```

Figure 2A

Anti-CD19 47G4 VK

V segment: A27
J segment: JK3

```
          E   I   V   L   T   Q   S   P   G   T   L   S   L   S   P   G   E   R
1         GAA ATT GTG TTG ACG CAG TCT CCA GGC ACC CTG TCT TTG TCT CCA GGG GAA AGA
                                                    CDR1
                                          ~~~~~~~~~~~~~~~~~~~~~~~~~~~~~~~~~~~~~~~~
          A   T   L   S   C   R   A   S   Q   S   V   S   S   S   Y   L   A   W
55        GCC ACC CTC TCC TGC AGG GCC AGT CAG AGT GTT AGC AGC AGC TAC TTA GCC TGG
                                                                        CDR2
                                                                        ~~~~~~~~~~~
          Y   Q   Q   K   P   G   Q   A   P   R   L   L   I   Y   G   A   S   S
109       TAC CAG CAG AAA CCT GGC CAG GCT CCC AGG CTC CTC ATC TAT GGT GCA TCC AGC
          CDR2
          ~~~~~~~~~~~
          R   A   T   G   I   P   D   R   F   S   G   S   G   S   G   T   D   F
163       AGG GCC ACT GGC ATC CCA GAC AGG TTC AGT GGC AGT GGG TCT GGG ACA GAC TTC
                                                                            CDR3
                                                                            ~~~
          T   L   T   I   S   R   L   E   P   E   D   F   A   V   Y   Y   C   Q
217       ACT CTC ACC ATC AGC AGA CTG GAG CCT GAA GAT TTT GCA GTG TAT TAC TGT CAG
              CDR3
          ~~~~~~~~~~~~~~~~~~~~~~~~~~~~~~~
          Q   Y   G   S   S   R   F   T   F   G   P   G   T   K   V   D   I   K
271       CAG TAT GGT AGC TCA CGA TTC ACT TTC GGC CCT GGG ACC AAA GTG GAT ATC AAA
```

Figure 2B

Anti-CD19 27F3 VH

V segment:    5-51
    D segment:    6-19
    J segment:    JH6b

```
              E   V   Q   L   V   Q   S   G   A   E   V   K   K   P   G   E   S   L
1             GAG GTG CAG CTG GTG CAG TCT GGA GCA GAG GTG AAA AAG CCC GGG GAG TCT CTG

CDR1
                                                      ~~~~~~~~~~~~~~~~~~~~
              K   I   S   C   K   G   S   G   Y   S   F   T   S   Y   W   I   A   W
55            AAG ATC TCC TGT AAG GGT TCT GGA TAC AGC TTT ACC AGC TAC TGG ATC GCC TGG

CDR2
                                                                  ~~~~~~~~~~~~~~~~~~
              V   R   Q   M   P   G   K   G   L   E   W   M   G   I   I   Y   P   G
109           GTG CGC CAG ATG CCC GGG AAA GGC CTG GAG TGG ATG GGG ATC ATC TAT CCT GGT

CDR2
              ~~~~~~~~~~~~~~~~~~~~~~~~~~~~~~~~~~~~~~~~
              D   S   D   T   R   Y   S   P   S   F   Q   G   Q   V   T   I   S   A
163           GAC TCT GAT ACC AGA TAC AGC CCG TCC TTC CAA GGC CAG GTC ACC ATC TCA GCC

D   K   S   I   S   T   A   Y   L   Q   W   S   S   L   K   A   S   D
217           GAC AAG TCC ATC AGC ACC GCC TAC CTG CAG TGG AGC AGC CTG AAG GCC TCG GAC

CDR3
                                                              ~~~~~~~~~~~~~~~~~~~~~~~~~~~~~~~~~~~~~~~~
              T   A   M   Y   Y   C   A   R   Q   G   Y   S   S   G   W   D   S   Y
271           ACC GCC ATG TAT TAC TGT GCG AGA CAG GGG TAT AGC AGT GGC TGG GAC TCC TAC

CDR3
              ~~~~~~~~~~~~~~~~~~~~
              Y   G   M   G   V   W   G   Q   G   T   T   V   T   V   S   S
325           TAC GGT ATG GGC GTC TGG GGC CAA GGG ACC ACG GTC ACC GTC TCC TCA
```

Figure 3A

Anti-CD19 27F3 VK

V segment:      L18
    J segment:      JK2

```
              A   I   Q   L   T   Q   S   P   S   S   L   S   A   S   V   G   D   R
1             GCC ATC CAG TTG ACC CAG TCT CCA TCC TCC CTG TCT GCA TCT GTA GGA GAC AGA
                                              CDR1
                                              ~~~~~~~~~~~~~~~~~~~~~~~~~~~~~~~~~~~~~~
              V   T   I   T   C   R   A   S   Q   G   I   S   S   A   L   A   W   Y
55            GTC ACC ATC ACT TGC CGG GCA AGT CAG GGC ATT AGC AGT GCT TTA GCC TGG TAT
                                                                          CDR2
                                                                          ~~~~~~~~~~~~~~~~~~~~
              Q   Q   K   P   G   K   A   P   K   L   L   I   Y   D   A   S   S   L
109           CAG CAG AAA CCA GGG AAA GCT CCT AAG CTC CTG ATC TAT GAT GCC TCC AGT TTG
              CDR2
              ~~~~~~~
              E   S   G   V   P   S   R   F   S   G   S   G   S   G   T   D   F   T
163           GAA AGT GGG GTC CCA TCA AGG TTC AGC GGC AGT GGA TCT GGG ACA GAT TTC ACT
                                                                                  CDR3
                                                                                  ~~~~~~~
              L   T   I   S   S   L   Q   P   E   D   F   A   T   Y   Y   C   Q   Q
217           CTC ACC ATC AGC AGC CTG CAG CCT GAA GAT TTT GCA ACT TAT TAC TGT CAA CAG
                      CDR3
                      ~~~~~~~~~~~~~~~~~~~~~~~~~~~~~~~~
              F   N   S   Y   P   Y   T   F   G   Q   G   T   K   L   E   I   K
271           TTT AAT AGT TAC CCG TAC ACT TTT GGC CAG GGG ACC AAG CTG GAG ATC AAA
```

Figure 3B

Anti-CD19 3C10 VH

V segment:     1-69
D segment:     1-26
J segment:     JH6b

```
         Q   V   Q   L   V   Q   S   G   A   E   V   K   K   P   G   S   S   V
1        CAG GTC CAG CTG GTG CAG TCT GGG GCT GAG GTG AAG AAG CCT GGG TCC TCG GTG

CDR1
                                                         ~~~~~~~~~~~~~~~~~~~~
         K   V   S   C   K   A   S   G   G   T   F   S   S   Y   T   I   N   W
55       AAG GTC TCC TGC AAG GCT TCT GGA GGC ACC TTC AGC AGC TAT ACT ATC AAC TGG

CDR2
                                                         ~~~~~~~~~~~~~~~~~~~~
         V   R   Q   A   P   G   Q   G   L   E   W   M   G   I   I   P   I
109      GTG CGA CAG GCC CCT GGA CAA GGG CTT GAG TGG ATG GGA GGG ATC ATT CCT ATC

CDR2
~~~~~~~~~~~~~~~~~~~~~~~~~~~~~~~~~~~~~~~~~~~~~~~~~~~~~~
         F   G   I   P   N   Y   A   Q   K   F   Q   G   R   V   T   I   T   A
163      TTT GGT ATA CCT AAC TAC GCA CAG AAG TTC CAG GGT AGA GTT ACG ATT ACC GCG

D   E   S   T   N   T   A   Y   M   E   L   S   S   L   R   A   E   D
217      GAC GAA TCC ACG AAC ACA GCC TAC ATG GAG CTG AGC AGC CTG AGA GCT GAG GAC

CDR3
                                                 ~~~~~~~~~~~~~~~~~~~~~~~~~~~~
         T   A   V   Y   Y   C   A   R   A   S   G   G   S   A   D   Y   S   Y
271      ACG GCC GTT TAT TAC TGT GCG AGA GCC AGT GGT GGG AGC GCG GAC TAT TCC TAC

CDR3
         ~~~~~~~~~~~~~~
         G   M   D   V   W   G   Q   G   T   A   V   T   V   S   S
325      GGT ATG GAC GTC TGG GGC CAA GGG ACC GCG GTC ACC GTC TCC TCA
```

Figure 4A

Anti-CD19 3C10 VK

V segment:     L15
J segment:     JK2

```
          D    I    Q    M    T    Q    S    P    S    S    L    S    A    S    V    G    D    R
 1       GAC  ATC  CAG  ATG  ACC  CAG  TCT  CCA  TCC  TCA  CTG  TCT  GCA  TCT  GTA  GGA  GAC  AGA
                                                            CDR1
                                           ~~~~~~~~~~~~~~~~~~~~~~~~~~~~~~~~~~~~~~~~~~~~~~~~~~~~~
          V    T    I    T    C    R    A    S    Q    G    I    S    S    W    L    A    W    Y
55       GTC  ACC  ATC  ACT  TGT  CGG  GCG  AGT  CAG  GGT  ATT  AGC  AGC  TGG  TTA  GCC  TGG  TAT
                                                                                 CDR2
                                                                        ~~~~~~~~~~~~~~~~~~~~~~~~~
          Q    Q    K    P    E    K    A    P    K    S    L    I    Y    A    A    S    S    L
109      CAG  CAG  AAA  CCA  GAG  AAA  GCC  CCT  AAG  TCC  CTG  ATC  TAT  GCT  GCA  TCC  AGT  TTG
         CDR2
         ~~~~~~~
          Q    S    G    V    P    S    R    F    S    G    S    G    S    G    T    D    F    T
163      CAA  AGT  GGG  GTC  CCA  TCA  AGG  TTC  AGC  GGC  AGT  GGA  TCT  GGG  ACA  GAT  TTC  ACT
                                                                                           CDR3
                                                                                         ~~~~~~~~
          L    T    I    S    S    L    Q    P    E    D    F    A    T    Y    Y    C    Q    Q
217      CTC  ACC  ATC  AGC  AGC  CTG  CAG  CCT  GAA  GAT  TTT  GCA  ACT  TAC  TAC  TGC  CAA  CAG
                    CDR3
              ~~~~~~~~~~~~~~~~~~~~~~~~~~
          Y    K    R    Y    P    Y    T    F    G    Q    G    T    K    L    E    I    K
271      TAT  AAG  AGA  TAC  CCG  TAC  ACT  TTT  GGC  CAG  GGG  ACC  AAG  CTG  GAG  ATC  AAA
```

Figure 4B

Anti-CD19 5G7 VH

> V segment:    5-51
> D segment:    3-10
> J segment:    JH6b

```
        E   V   Q   L   V   Q   S   G   A   E   V   K   K   P   G   E   S   L
1       GAG GTG CAG CTG GTG CAG TCT GGA GCA GAG GTG AAA AAG CCC GGG GAG TCT CTG

CDR1
                                                                    ~~~~~~~~~~~~~~~~~~~~
        N   I   S   C   K   G   S   G   Y   S   F   T   S   Y   W   I   G   W
55      AAC ATC TCC TGT AAG GGT TCT GGA TAC AGC TTT ACC AGC TAC TGG ATC GGC TGG

CDR2
                                                                    ~~~~~~~~~~~~~~~~~~~~
        V   R   Q   M   P   G   K   G   L   E   W   M   G   I   I   Y   P   G
109     GTG CGC CAG ATG CCC GGG AAA GGC CTG GAG TGG ATG GGG ATC ATC TAT CCT GGT

CDR2
        ~~~~~~~~~~~~~~~~~~~~~~~~~~~~~~~~~~~~~~~~~~~~~~~~~~~~~
        D   S   D   T   R   Y   S   P   S   F   Q   G   Q   V   T   I   S   A
163     GAC TCT GAT ACC AGA TAC AGC CCG TCC TTC CAA GGC CAG GTC ACC ATC TCA GCC

D   K   S   I   N   T   A   Y   L   Q   W   S   S   L   K   A   S   D
217     GAC AAG TCC ATC AAC ACC GCC TAC CTG CAG TGG AGC AGC CTG AAG GCC TCG GAC

CDR3
                                                            ~~~~~~~~~~~~~~~~~~~~~~~~~~~~~~
        T   A   M   Y   Y   C   A   R   G   V   S   M   I   W   G   V   I   M
271     ACC GCC ATG TAT TAC TGT GCG AGA GGG GTT TCT ATG ATT TGG GGA GTT ATT ATG

CDR3
        ~~~~~~~~
        D   V   W   G   Q   G   T   T   V   T   V   S   S
325     GAC GTC TGG GGC CAA GGG ACC ACG GTC ACC GTC TCC TCA
```

Figure 5A

Anti-CD19 5G7 VK

V segment:   L18
J segment:   JK1

```
         A   I   Q   L   T   Q   S   P   S   S   L   S   A   S   V   G   D   R
  1     GCC ATC CAG TTG ACC CAG TCT CCA TCC TCC CTG TCT GCA TCT GTA GGA GAC AGA
                                                 CDR1
                             ~~~~~~~~~~~~~~~~~~~~~~~~~~~~~~~~~~~~~~~~~~~~~~~~~
         V   T   I   T   C   R   A   S   Q   G   I   S   S   A   L   A   W   Y
 55     GTC ACC ATC ACT TGC CGG GCA AGT CAG GGC ATT AGC AGT GCT TTA GCC TGG TAT
                                                                       CDR2
                                                                 ~~~~~~~~~~~~~~
         Q   Q   K   P   G   K   A   P   K   L   L   I   Y   D   A   S   S   L
109     CAG CAG AAA CCA GGG AAA GCT CCT AAG CTC CTG ATC TAT GAT GCC TCC AGT TTG
        CDR2
        ~~~~~~~~
         E   S   G   V   P   S   R   F   S   G   S   G   S   G   T   D   F   T
163     GAA AGT GGG GTC CCA TCA AGG TTC AGC GGC AGT GGA TCT GGG ACA GAT TTC ACT
                                                                           CDR3
                                                                       ~~~~~~~~
         L   T   I   S   S   L   Q   P   E   D   F   A   T   Y   Y   C   Q   Q
217     CTC ACC ATC AGC AGC CTG CAG CCT GAA GAT TTT GCA ACT TAT TAC TGT CAA CAG
                CDR3
        ~~~~~~~~~~~~~~~~~~~~~~~~~~~~
         F   N   S   Y   P   W   T   F   G   Q   G   T   K   V   E   I   K
271     TTT AAT AGT TAC CCG TGG ACG TTC GGC CAA GGG ACC AAG GTG GAA ATC AAA
```

Figure 5B

Anti-CD19 13F1 VH

V segment: 5-51
D segment: 6-19
J segment: JH6b

```
      E   V   Q   L   V   Q   S   G   A   E   V   K   K   P   G   E   S   L
1     GAG GTG CAG CTG GTG CAG TCT GGA GCA GAG GTG AAA AAG CCC GGG GAG TCT CTG
                                                                  CDR1
                                                        ~~~~~~~~~~~~~~~~~~~~
      Q   I   S   C   K   G   S   G   Y   T   F   T   N   Y   W   I   A   W
55    CAG ATC TCC TGT AAG GGT TCT GGA TAC ACC TTT ACC AAC TAC TGG ATC GCC TGG
                                                              CDR2
                                                    ~~~~~~~~~~~~~~~~~~~~~~~~
      V   R   Q   M   P   G   K   G   L   E   W   M   G   I   I   Y   P   G
109   GTG CGC CAG ATG CCC GGG AAA GGC CTG GAG TGG ATG GGG ATC ATC TAT CCT GGT
                  CDR2
      ~~~~~~~~~~~~~~~~~~~~~~~~~~~~~~~~~~~~~~~~~~~~~~~~~~~~
      D   S   D   T   R   Y   S   P   S   F   Q   G   Q   V   T   I   S   A
163   GAC TCT GAT ACC AGA TAC AGC CCG TCC TTC CAA GGC CAG GTC ACC ATC TCA GCC

D   K   S   I   S   T   A   Y   L   Q   W   S   G   L   K   A   S   D
217   GAC AAG TCC ATC AGC ACC GCC TAC CTA CAG TGG AGC GGC CTG AAG GCC TCG GAC
                                                          CDR3
                                              ~~~~~~~~~~~~~~~~~~~~~~~~~~~~~~
      T   A   M   Y   Y   C   A   R   Q   G   Y   S   S   G   W   R   S   Y
271   ACC GCC ATG TAT TAC TGT GCG AGA CAG GGA TAT AGC AGT GGC TGG CGC TCC TAC
              CDR3
      ~~~~~~~~~~~~~~~~~~~~
      Y   G   M   G   V   W   G   Q   G   T   T   V   T   V   S   S
325   TAC GGT ATG GGC GTC TGG GGC CAA GGG ACC ACG GTC ACC GTC TCC TCA
```

Figure 6A

Anti-CD19 13F1 VK

V segment: L18
J segment: JK2

```
        A   I   Q   L   T   Q   S   P   S   S   L   S   A   S   V   G   D   R
1       GCC ATC CAG TTG ACC CAG TCT CCA TCC TCC CTG TCT GCA TCT GTA GGA GAC AGA
                                                CDR1
                                        ~~~~~~~~~~~~~~~~~~~~~~~~~~~~~~~~~~~~~~
        V   T   I   T   C   R   A   S   Q   G   I   S   S   A   L   A   W   Y
55      GTC ACC ATC ACT TGC CGG GCA AGT CAG GGC ATT AGC AGT GCT TTA GCC TGG TAT
                                                                CDR2
                                                        ~~~~~~~~~~~~~~~~~~~~~~
        Q   Q   K   P   G   K   A   P   K   L   L   I   Y   D   A   S   S   L
109     CAG CAG AAA CCA GGG AAA GCT CCT AAG CTC CTG ATC TAT GAT GCC TCC AGT TTG

CDR2
        ~~~~~~~
        E   S   G   V   P   S   R   F   S   G   S   G   S   G   T   D   F   T
163     GAA AGT GGG GTC CCA TCA AGG TTC AGC GGC AGT GGA TCT GGG ACA GAT TTC ACT
                                                                        CDR3
                                                                        ~~~~~~~
        L   T   I   S   S   L   Q   P   E   D   F   A   T   Y   Y   C   Q   Q
217     CTC ACC ATC AGC AGC CTG CAG CCT GAA GAT TTT GCA ACT TAT TAC TGT CAA CAG

CDR3
        ~~~~~~~~~~~~~~~~~~~~~~~~~~~~~~
        F   N   S   Y   P   H   T   F   G   Q   G   T   K   L   E   I   K
271     TTT AAT AGT TAC CCT CAC ACT TTT GGC CAG GGG ACC AAG CTG GAG ATC AAA
```

Figure 6B

Anti-CD19 46E8 VH

V segment:      5-51
    D segment:      6-19
    J segment:      JH6b

```
          E   V   Q   L   V   Q   S   G   A   E   V   K   K   P   G   E   S   L
1         GAG GTG CAG CTG GTG CAG TCT GGA GCA GAG GTG AAA AAG CCC GGG GAG TCT CTG
                                                                CDR1
                                                       ~~~~~~~~~~~~~~~~~~~~~~
          Q   I   S   C   K   G   S   G   Y   T   F   T   N   Y   W   I   A   W
55        CAG ATC TCC TGT AAG GGT TCT GGA TAC ACC TTT ACC AAC TAC TGG ATC GCC TGG
                                                                     CDR2
                                                            ~~~~~~~~~~~~~~~~~~~~~
          V   R   Q   M   P   G   K   G   L   E   W   M   G   I   I   Y   P   G
109       GTG CGC CAG ATG CCC GGG AAA GGC CTG GAG TGG ATG GGG ATC ATC TAT CCT GGT
                  CDR2
          ~~~~~~~~~~~~~~~~~~~~~~~~~~~~~~~~~~~~~~~~~~~~~~~~~~
          D   S   D   T   R   Y   S   P   S   F   Q   G   Q   V   T   I   S   A
163       GAC TCT GAT ACC AGA TAC AGC CCG TCC TTC CAA GGC CAG GTC ACC ATC TCA GCC

D   K   S   I   S   T   A   Y   L   Q   W   S   G   L   K   A   S   D
217       GAC AAG TCC ATC AGC ACC GCC TAC CTA CAG TGG AGC GGC CTG AAG GCC TCG GAC
                                                                CDR3
                                                       ~~~~~~~~~~~~~~~~~~~~~~~~~~~~~
          T   A   M   Y   Y   C   A   R   Q   G   Y   S   S   G   W   R   S   Y
271       ACC GCC ATG TAT TAC TGT GCG AGA CAG GGA TAT AGC AGT GGC TGG CGC TCC TAC
              CDR3
          ~~~~~~~~~~~~~~~~~~~~
          Y   G   M   G   V   W   G   Q   G   T   T   V   T   V   S   S
325       TAC GGT ATG GGC GTC TGG GGC CAA GGG ACC ACG GTC ACC GTC TCC TCA
```

Figure 7A

Anti-CD19 46E8 VK

V segment:   L18
J segment:   JK2

```
         A   I   Q   L   T   Q   S   P   S   S   L   S   A   S   V   G   D   R
  1     GCC ATC CAG TTG ACC CAG TCT CCA TCC TCC CTG TCT GCA TCT GTA GGA GAC AGA
                                         CDR1
                              ~~~~~~~~~~~~~~~~~~~~~~~~~~~~~~~~~~~~~~~~~~~~~~~
         V   T   I   T   C   R   A   S   Q   G   I   S   S   A   L   A   W   Y
 55     GTC ACC ATC ACT TGC CGG GCA AGT CAG GGC ATT AGC AGT GCT TTA GCC TGG TAT
                                                                    CDR2
                                                         ~~~~~~~~~~~~~~~~~~~~~
         Q   Q   K   P   G   K   A   P   K   L   L   I   Y   D   A   S   S   L
109     CAG CAG AAA CCA GGG AAA GCT CCT AAG CTC CTG ATC TAT GAT GCC TCC AGT TTG
        CDR2
        ~~~~~~~~
         E   S   G   V   P   S   R   F   S   G   S   G   S   G   T   D   F   T
163     GAA AGT GGG GTC CCA TCA AGG TTC AGC GGC AGT GGA TCT GGG ACA GAT TTC ACT
                                                                          CDR3
                                                                         ~~~~~~
         L   T   I   S   S   L   Q   P   E   D   F   A   T   Y   Y   C   Q   Q
217     CTC ACC ATC AGC AGC CTG CAG CCT GAA GAT TTT GCA ACT TAT TAC TGT CAA CAG
              CDR3
        ~~~~~~~~~~~~~~~~~~~~~~~~~~~~~~~~~
         F   N   S   Y   P   H   T   F   G   Q   G   T   K   L   E   I   K
271     TTT AAT AGT TAC CCT CAC ACT TTT GGC CAG GGG ACC AAG CTG GAG ATC AAA
```

Figure 7B

Anti-CD19 21D4, 21D4a VH region

```
                                                                    CDR1
5-51 germline   E V Q L V Q S G A E V K K P G E S L K I S C K G S G Y S F T S Y W I G W
21D4      VH    - - - - - - - - - - - - - - - - - - - - - - - - - - - - S - - - - - -
21D4a     VH    - - - - - - - - - - - - - - - - - - - - - - - - - - - - S - - - - - -

CDR2
5-51 germline   V R Q M P G K G L E W M G I I I Y P G D S D T R Y S P S F Q G Q V T I S A
21D4      VH    - - - - - - - - - - - - - - - - - - D - - - - - - - - - - - - - - - - -
21D4a     VH    - - - - - - - - - - - - - - - - - - D - - - - - - - - - - - - - - - - -

CDR3
5-51 germline   D K S I S T A Y L Q W S S L K A S D T A M Y Y C A R
21D4      VH    - - - - - - R - - - - - - - - - - - - - - - - - - - H V T M I W G V I H
21D4a     VH    - - - - - - R - - - - - - - - - - - - - - - - - - - H V T M I W G V I H JH4b germline   D Y W G Q G T L V T V S S
21D4      VH    - F - - - - - - - - - - -    (JH4b)
21D4a     VH    - F - - - - - - - - - - -    (JH4b)
```

Figure 8

Anti-CD19 47G4 VH region

```
                                              CDR1
1-69 germline   Q V Q L V Q S G A E V K K P G S S V K V S C K A S G G T F S S Y A I S W
47G4 VH         - - - - - - - - - - - - - - - - - - - - - - D - - - - - - - - - - - -

CDR2
1-69 germline   V R Q A P G Q G L E W M G G I I P I F G T A N Y A Q K F Q G R V T I T A
47G4 VH         - - - - - - - - - - - - - - - - - - - T - - - - - Q - - - - - -

CDR3
1-69 germline   D E S T S T A Y M E L S S L R S E D T A V Y Y C A R
JH5b germline                                                       E A V A A D     W F D P
47G4 VH         - - - - - - - - - - - - - - - - - - - - - - - - - - - - - - - - -   - - - - L JH5b germline   W G Q G T L V T V S S   (JH5b)
47G4 VH         - - - - - - - - - - -
```

Figure 9

Anti-CD19 27F3 VH region

```
                       CDR1
5-51 germline  E V Q L V Q S G A E V K K P G E S L K I S C K G S G Y S F T S Y W I G W
27F3 VH        - - - - - - - - - - - - - - - - - - - - - - - - - - - - - - - - - - A CDR2
5-51 germline  V R Q M P G K G L E W M G I I Y P G D S D T R Y S P S F Q G Q V T I S A
27F3 VH        - - - - - - - - - - - - - - - - - - - - - - - - - - - - - - - - - - -

CDR3
5-51 germline  D K S I S T A Y L Q W S S L K A S D T A M Y Y C A R
JH6b germline                                                       Q G Y S S G W D S Y Y
27F3 VH        - - - - - - - - - - - - - - - - - - - - - - - - -  - Q G Y S S G W D S Y Y JH6b germline  Y G M D V W G Q G T T V T V S S   (JH6b)
27F3 VH        - - - G - - - - - - - - - - - -
```

Figure 10

Anti-CD19 3C10 VH region

```
                                                                    CDR1
1-69 germline    Q V Q L V Q S G A E V K K P G S S V K V S C K A S G G T F S S Y A I S W
3C10 VH          - - - - - - - - - - - - - - - - - - - - - - - - - - - - - - - T - N -

CDR2
1-69 germline    V R Q A P G Q G L E W M G G I I P I F G T A N Y A Q K F Q G R V T I T A
3C10 VH          - - - - - - - - - - - - - - - I P - - - - - - - - - - - - - - - - - -

1-69 germline    D E S T S T A Y M E L S S L R S E D T A V Y Y C A R
JH6b germline
3C10 VH          - - - N - - - - - - - - - - - - - - A - - - - - - -

CDR3
                                                          ─────────────────────
                                                          A S G G S A D - Y Y Y S

JH6b germline    G M D V W G Q G T T V T V S S                (JH6b)
3C10 VH          - - - - - - - - - - A - - - -
```

Figure 11

Anti-CD19 5G7 VH region

```
                                                                CDR1
5-51 germline    E V Q L V Q S G A E V K K P G E S L K I S C K G S G Y S F T S Y W I G W
5G7 VH           - - - - - - - - - - - - - - - - - - - - - - - - - N - - - - - - - - -

CDR2
5-51 germline    V R Q M P G K G L E W M G I I Y P G D S D T R Y S P S F Q G Q V T I S A
5G7 VH           - - - - - - - - - - - - - - - - - - - - - - - - - - - - - - - - - - -

CDR3
5-51 germline    D K S I S T A Y L Q W S S L K A S D T A M Y Y C A R
JH6b germline
5G7 VH           - - - - - - - - N - - - - - - - - - - - - - - - - -  G V S M I W G V I  M JH6b germline    D V W G Q G T T V T V S S   (JH6b)
5G7 VH           - - - - - - - - - - - - -
```

Figure 12

Anti-CD19 13F1 VH region

```
                                                              CDR1
5-51 germline  E V Q L V Q S G A E V K K P G E S L K I S C K G S G Y S F T S Y W I G W
13F1 VH        - - - - - - - - - - - - - - - - - - - - - - - - - - T - - N - - - A -

CDR2
5-51 germline  V R Q M P G K G L E W M G I I Y P G D S D T R Y S P S F Q G Q V T I S A
13F1 VH        - - - - - - - - - - - - - - - - - Q - - - - - - - - - - - - - - - - -

CDR3
5-51 germline  D K S I S T A Y L Q W S S L K A S D T A M Y Y C A R
JH6b germline                                                       Q G Y S S G W   Y Y
13F1 VH        - - - - - - - - - - - - - - - - - - - - - - - - -   - - - - - - R S - -

JH6b germline  Y G M D V W G Q G T T V T V S S   (JH6b)
13F1 VH        - - - - - G - - - - - - - - - -
```

Figure 13

Anti-CD19 46E8 VH region

```
                                                           CDR1
5-51 germline   E V Q L V Q S G A E V K K P G E S L K I S C K G S G Y S F T S Y W I G W
46E8 VH         - - - - - - - - - - - - - - - - - - - - Q - - - - - T - N - - - A CDR2
5-51 germline   V R Q M P G K G L E W M G I I Y P G D S D T R Y S P S F Q G Q V T I S A
46E8 VH         - - - - - - - - - - - - - - - - - - - - - - - - - - - - - - - - - -

CDR3
5-51 germline   D K S I S T A Y L Q W S S L K A S D T A M Y Y C A R
JH6b germline                                                      - Q G Y S S G W R S Y Y
46E8 VH         - - - - - - - - - - - G - - - - - - - - - - - - -

CDR3
JH6b germline   Y G M D V W G Q G T T V T V S S    (JH6b)
46E8 VH         - - - G - - - - - - - - - - - -
```

Figure 14

Anti-CD19 21D4 VK region

```
                         CDR1
L18 germline    A I Q L T Q S P S S L S A S V G D R V T I T C R A S Q G I S S
21D4 VK         - - - - - - - - - - - - - - - - - - - - - - - - - - - - - - -

────────────              CDR2
L18 germline    A L A W Y Q Q K P G K A P K L L I Y D A S S L E S G V P S R F
21D4 VK         - - - - - - - - - - - - - - - - - - - - - - - - - - - - - - -

CDR3
L18 germline    S G S G S G T D F T L T I S S L Q P E D F A T Y Y C Q Q F N S
21D4 VK         - - - - - - - - - - - - - - - - - - - - - - - - - - - - - - -

L18 germline      Y P
JK2 germline      Y T F G Q G T K L E I K    (JK2)
21D4 VK         - - - - - - - - - - - - -
```

Figure 15

Anti-CD19 21D4a VK region

```
                                                      CDR1
L18 germline    A I Q L T Q S P S S L S A S V G D R V T I T C R A S Q G I S S
21D4a VK        - - - - - - - - - - - - - - - - - - - - - - - - - - - - - -

CDR2
L18 germline    A L A W Y Q Q K P G K A P K L L I Y D A S S L E S G V P S R F
21D4a VK        - - - - - - - - - - - - - - - - - - - - - - - - - - - - - -

CDR3
L18 germline    S G S G T D F T L T I S S L Q P E D F A T Y Y C Q Q F N S
21D4a VK        - - - - - - - - - - - - - - - - - - - - - - - - - - - - -

L18 germline    Y P
JK3 germline         F T F G P G T K V D I K        (JK3)
21D4a VK        - -  - - - - - - - - - - - -
```

Figure 16

Anti-CD19 47G4 VK region

```
                        CDR1
A27 germline    E I V L T Q S P G T L S L S P G E R A T L S C R A S Q S V S S
47G4 VK         - - - - - - - - - - - - - - - - - - - - - - - - - - - - - -

CDR2
A27 germline    S Y L A W Y Q Q K P G Q A P R L L I Y G A S S R A T G I P D R
47G4 VK         - - - - - - - - - - - - - - - - - - - - - - - - - - - - - -

CDR3
A27 germline    F S G S G S G T D F T L T I S R L E P E D F A V Y Y C Q Q Y G
47G4 VK         - - - - - - - - - - - - - - - - - - - - - - - - - - - - - -

A27 germline    S S
JK3 germline          F T F G P G T K V D I K   (JK3)
47G4 VK         - -   - R - - - - - - - - - -
```

Figure 17

Anti-CD19 27F3 VK region

```
                                                                CDR1
L18 germline   A I Q L T Q S P S S L S A S V G D R V T I T C R A S Q G I S S
27F3 VK        - - - - - - - - - - - - - - - - - - - - - - - - - - - - - -

CDR2
L18 germline   A L A W Y Q Q K P G K A P K L L I Y D A S S L E S G V P S R F
27F3 VK        - - - - - - - - - - - - - - - - - - - - - - - - - - - - - -

CDR3
L18 germline   S G S G S G T D F T L T I S S L Q P E D F A T Y Y C Q Q F N N
27F3 VK        - - - - - - - - - - - - - - - - - - - - - - - - - - - - - - S L18 germline   Y P
JK2 germline        Y T F G Q G T K L E I K     (JK2)
27F3 VK        - -  - - - - - - - - - - - -
```

Figure 18

Anti-CD19 3C10 VK region

```
                        CDR1
L15 germline    D I Q M T Q S P S S L S A S V G D R V T I T C R A S Q G I S S
3C10 VK         - - - - - - - - - - - - - - - - - - - - - - - - - - - - - -

CDR2
L15 germline    W L A W Y Q Q K P E K A P K S L I Y A A S S L Q S G V P S R F
3C10 VK         - - - - - - - - - - - - - - - - - - - - - - - - - - - - - -

CDR3
L15 germline    S G S G S G T D F T L T I S S L Q P E D F A T Y Y C Q Q Y N S
3C10 VK         - - - - - - - - - - - - - - - - - - - - - - - - - - - - K R Y P
L15 germline    - -    Y T F G Q G T K L E I K    (JK2)
JK2 germline
3C10 VK         - -    - - - - - - - - - - - -
```

Figure 19

Anti-CD19 5G7 VK region

```
                             CDR1
L18 germline  A I Q L T Q S P S S L S A S V G D R V T I T C R A S Q G I S S
5G7 VK        - - - - - - - - - - - - - - - - - - - - - - - - - - - - - -

CDR2
L18 germline  A L A W Y Q Q K P G K A P K L L I Y D A S S L E S G V P S R F
5G7 VK        - - - - - - - - - - - - - - - - - - - - - - - - - - - - - -

CDR3
L18 germline  S G S G S G T D F T L T I S S L Q P E D F A T Y Y C Q Q F N N
5G7 VK        - - - - - - - - - - - - - - - - - - - - - - - - - - - - - S Y P
L18 germline  
L18 JK1 germline  W T F G Q G T K V E I K    (JK1)
5G7 VK        - - - - - - - - - - - -
```

Figure 20

Anti-CD19 13F1 VK region

```
                                                     CDR1
L18 germline    A I Q L T Q S P S S L S A S V G D R V T I T C R A S Q G I S S
13F1 VK         - - - - - - - - - - - - - - - - - - - - - - - - - - - - - -

CDR2
L18 germline    A L A W Y Q Q K P G K A P K L L I Y D A S S L E S G V P S R F
13F1 VK         - - - - - - - - - - - - - - - - - - - - - - - - - - - - - -

CDR3
L18 germline    S G S G S G T D F T L T I S S L Q P E D F A T Y Y C Q Q F N N
13F1 VK         - - - - - - - - - - - - - - - - - - - - - - - - - - - - - -

L18 germline              Y P
JK2 germline    T F G Q G T K L E I K      (JK2)
13F1 VK         - - H - - - - - - - -
```

Figure 21

Anti-CD19 46E8 VK region

```
                                                        CDR1
L18 germline   A I Q L T Q S P S S L S A S V G D R V T I T C R A S Q G I S S
46E8 VK        - - - - - - - - - - - - - - - - - - - - - - - - - - - - - - -

CDR2
L18 germline   A L A W Y Q Q K P G K A P K L L I Y D A S S L E S G V P S R F
46E8 VK        - - - - - - - - - - - - - - - - - - - - - - - - - - - - - - -

CDR3
L18 germline   S G S G S G T D F T L T I S S L Q P E D F A T Y Y C Q Q F N N
46E8 VK        - - - - - - - - - - - - - - - - - - - - - - - - - - - - - - -

CDR3
L18 germline    Y P
JK2 germline         T F G Q G T K L E I K           (JK2)
46E8 VK        - - H - - - - - - - - - - - -
```

Figure 22

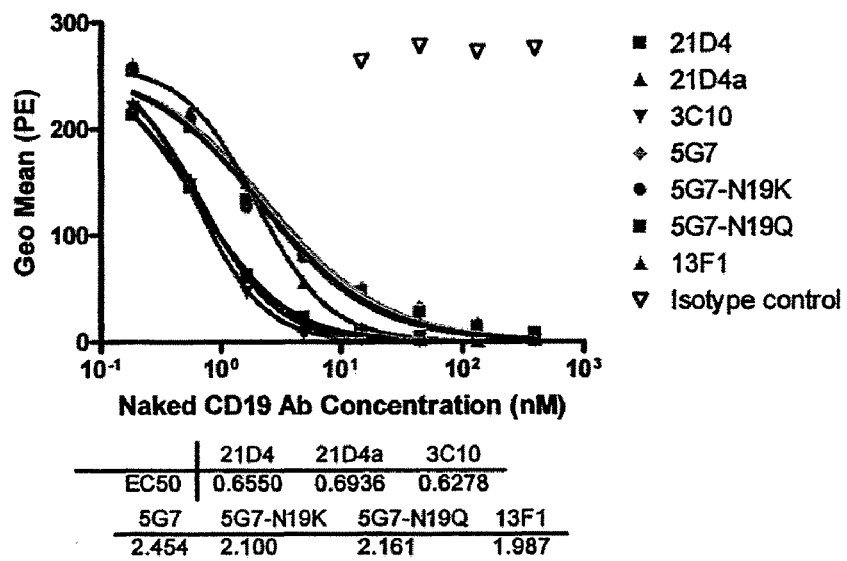
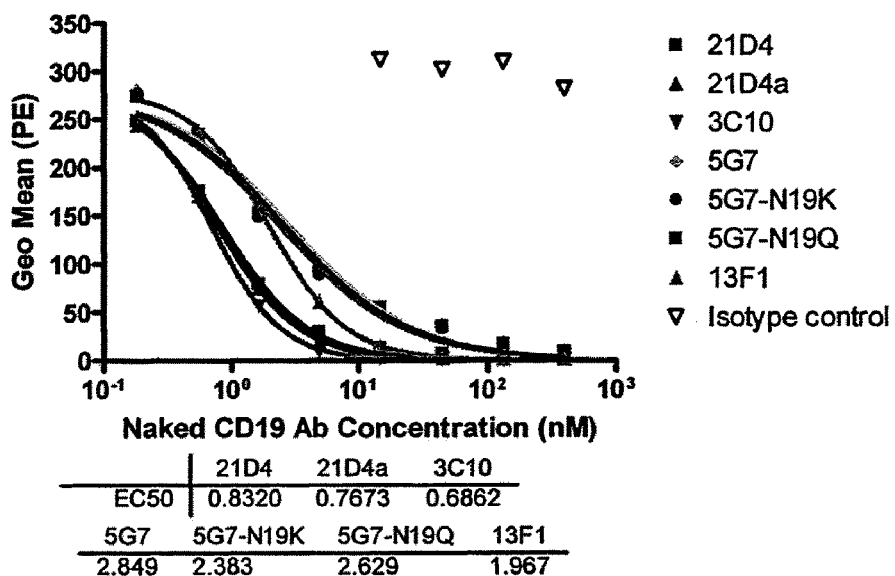
Figure 24

A)
Single Dose Efficacy of naked antibodies on ARH-77 tumors
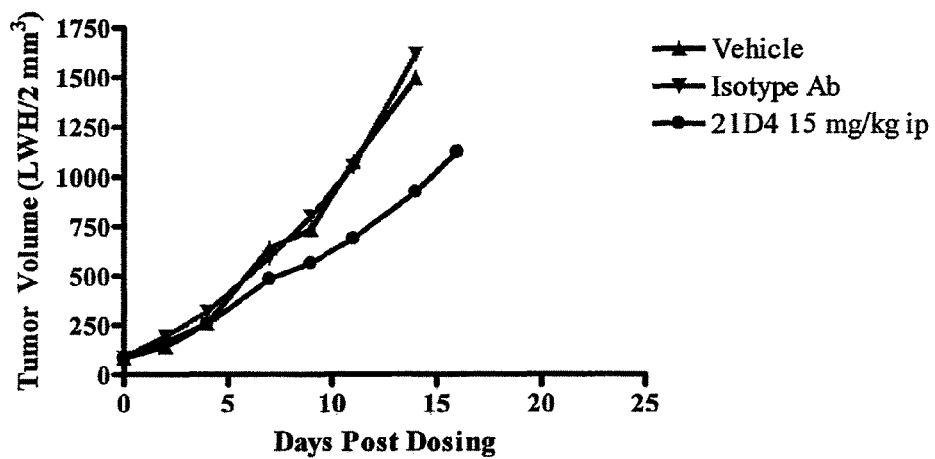
B)
Efficacy of single dose naked αCD19 Ab on Raji tumors
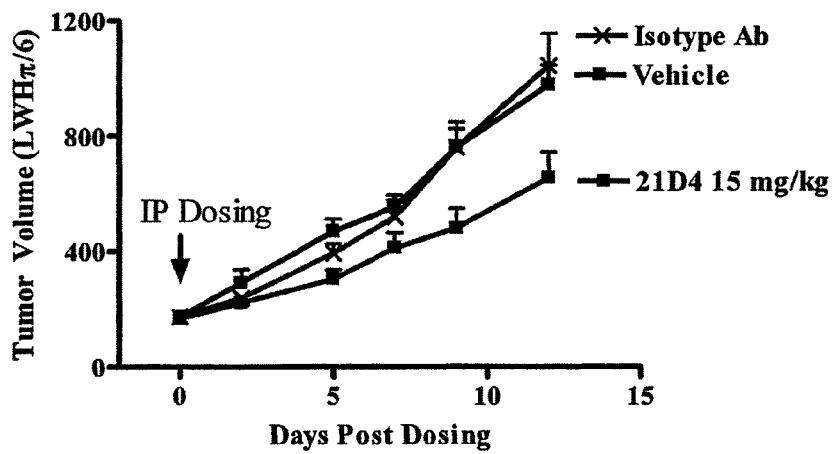
Figure 30

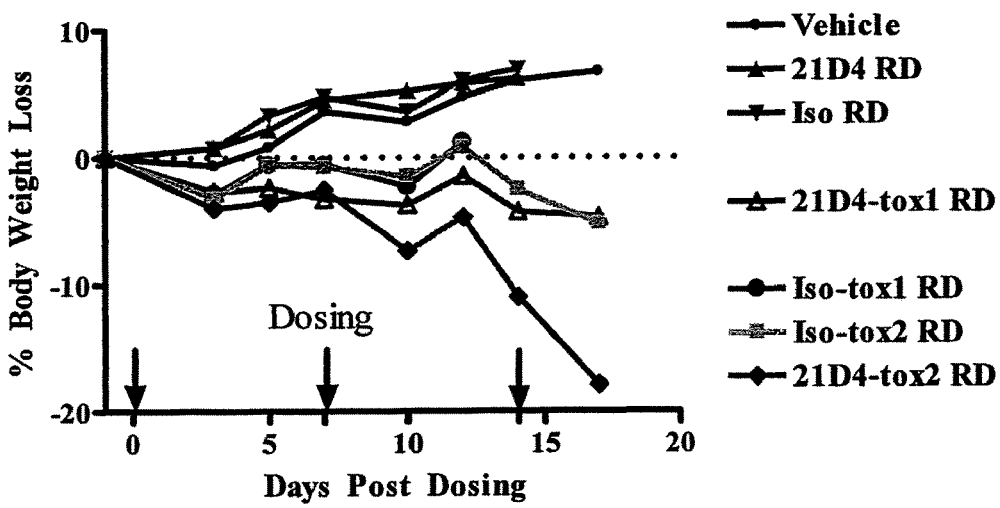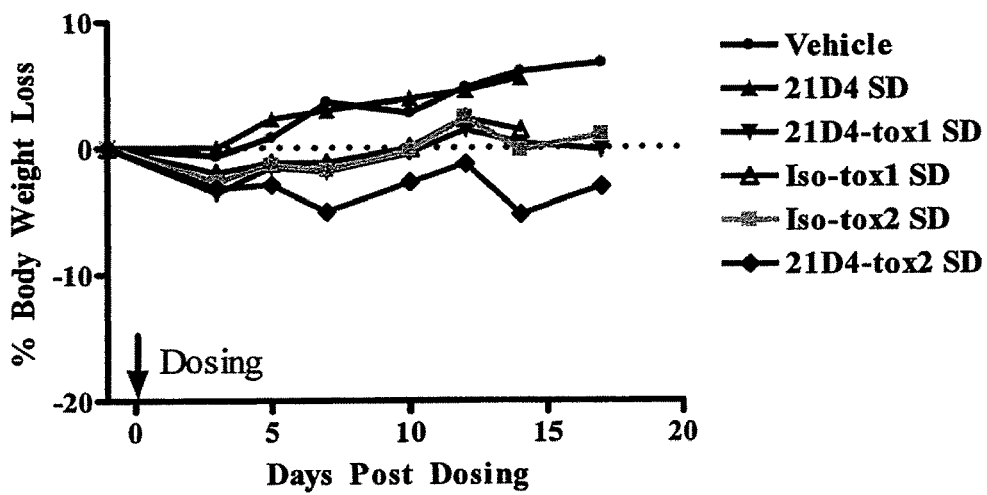
Figure 33

A

SEQUENCE LISTING

<160> NUMBER OF SEQ ID NOS: 87

<210> SEQ ID NO 1
<211> LENGTH: 121
<212> TYPE: PRT
<213> ORGANISM: Homo sapiens

<400> SEQUENCE: 1

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Ser Ser Ser
            20                  25                  30

Trp Ile Gly Trp Val Arg Gln Met Pro Gly Lys Gly Leu Glu Trp Met
        35                  40                  45

Gly Ile Ile Tyr Pro Asp Asp Ser Asp Thr Arg Tyr Ser Pro Ser Phe
    50                  55                  60

Gln Gly Gln Val Thr Ile Ser Ala Asp Lys Ser Ile Arg Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Thr Met Ile Trp Gly Val Ile Ile Asp Phe Trp Gly
            100                 105                 110

Gln Gly Thr Leu Val Thr Val Ser Ser
        115                 120

<210> SEQ ID NO 2
<211> LENGTH: 119
<212> TYPE: PRT
<213> ORGANISM: Homo sapiens

<400> SEQUENCE: 2

Gln Val Gln Leu Val Gln Ser Gly Ala Glu Val Lys Lys Pro Gly Ser
 1               5                  10                  15

Ser Val Lys Val Ser Cys Lys Asp Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Gln Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Val Ala Ala Asp Trp Leu Asp Pro Trp Gly Gln Gly
            100                 105                 110

Thr Leu Val Thr Val Ser Ser
        115

<210> SEQ ID NO 3
<211> LENGTH: 124
<212> TYPE: PRT
<213> ORGANISM: Homo sapiens

<400> SEQUENCE: 3

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr

```
                    20                  25                  30
Trp Ile Ala Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gly Tyr Ser Ser Gly Trp Asp Ser Tyr Tyr Gly Met Gly
            100                 105                 110

Val Trp Gly Gln Gly Thr Thr Val Thr Val Ser Ser
        115                 120

<210> SEQ ID NO 4
<211> LENGTH: 123
<212> TYPE: PRT
<213> ORGANISM: Homo sapiens

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Met
        35                  40                  45

Gly Gly Ile Ile Pro Ile Phe Gly Ile Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ala Glu Asp Thr Ala Val Tyr Tyr Cys
                85                  90                  95

Ala Arg Ala Ser Gly Gly Ser Ala Asp Tyr Ser Tyr Gly Met Asp Val
            100                 105                 110

Trp Gly Gln Gly Thr Ala Val Thr Val Ser Ser
        115                 120

<210> SEQ ID NO 5
<211> LENGTH: 121
<212> TYPE: PRT
<213> ORGANISM: Homo sapiens

<400> SEQUENCE: 5

Glu Val Gln Leu Val Gln Ser Gly Ala Glu Val Lys Lys Pro Gly Glu
1               5                   10                  15

Ser Leu Asn Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Val Ser Met Ile Trp Gly Val Ile Met Asp Val Trp Gly
            100                 105                 110
```

```
Gln Gly Thr Thr Val Thr Val Ser Ser
        115                 120

<210> SEQ ID NO 6
<211> LENGTH: 124
<212> TYPE: PRT
<213> ORGANISM: Homo sapiens

<400> SEQUENCE: 6

Glu Val Gln Leu Val Gln Ser Gly Ala Glu Val Lys Lys Pro Gly Glu
1               5                   10                  15

Ser Leu Gln Ile Ser Cys Lys Gly Ser Gly Tyr Thr Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Gly Leu Lys Ala Ser Asp Thr Ala Met Tyr Tyr Cys
                85                  90                  95

Ala Arg Gln Gly Tyr Ser Ser Gly Trp Arg Ser Tyr Tyr Gly Met Gly
            100                 105                 110

Val Trp Gly Gln Gly Thr Thr Val Thr Val Ser Ser
        115                 120

<210> SEQ ID NO 7
<211> LENGTH: 124
<212> TYPE: PRT
<213> ORGANISM: Homo sapiens

<400> SEQUENCE: 7

Glu Val Gln Leu Val Gln Ser Gly Ala Glu Val Lys Lys Pro Gly Glu
1               5                   10                  15

Ser Leu Gln Ile Ser Cys Lys Gly Ser Gly Tyr Thr Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Gly Leu Lys Ala Ser Asp Thr Ala Met Tyr Tyr Cys
                85                  90                  95

Ala Arg Gln Gly Tyr Ser Ser Gly Trp Arg Ser Tyr Tyr Gly Met Gly
            100                 105                 110

Val Trp Gly Gln Gly Thr Thr Val Thr Val Ser Ser
        115                 120

<210> SEQ ID NO 8
<211> LENGTH: 107
<212> TYPE: PRT
<213> ORGANISM: Homo sapiens

<400> SEQUENCE: 8

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
```

-continued

```
                    20                  25                  30
Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys
            100                 105

<210> SEQ ID NO 9
<211> LENGTH: 107
<212> TYPE: PRT
<213> ORGANISM: Homo sapiens

<400> SEQUENCE: 9

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys
            100                 105

<210> SEQ ID NO 10
<211> LENGTH: 108
<212> TYPE: PRT
<213> ORGANISM: Homo sapiens

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Arg
                85                  90                  95

Phe Thr Phe Gly Pro Gly Thr Lys Val Asp Ile Lys
            100                 105

<210> SEQ ID NO 11
<211> LENGTH: 107
<212> TYPE: PRT
<213> ORGANISM: Homo sapiens
```

```
<400> SEQUENCE: 11

Ala Ile Gln Leu Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Ala
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Tyr
                 85                  90                  95

Thr Phe Gly Gln Gly Thr Lys Leu Glu Ile Lys
                100                 105

<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Lys Arg Tyr Pro Tyr
                 85                  90                  95

Thr Phe Gly Gln Gly Thr Lys Leu Glu Ile Lys
                100                 105

<210> SEQ ID NO 13
<211> LENGTH: 107
<212> TYPE: PRT
<213> ORGANISM: Homo sapiens

<400> SEQUENCE: 13

Ala Ile Gln Leu Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Ala
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Trp
                 85                  90                  95

Thr Phe Gly Gln Gly Thr Lys Val Glu Ile Lys
```

<210> SEQ ID NO 14
<211> LENGTH: 107
<212> TYPE: PRT
<213> ORGANISM: Homo sapiens

<400> SEQUENCE: 14

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro His
                85                  90                  95

Thr Phe Gly Gln Gly Thr Lys Leu Glu Ile Lys
            100                 105

<210> SEQ ID NO 15
<211> LENGTH: 107
<212> TYPE: PRT
<213> ORGANISM: Homo sapiens

<400> SEQUENCE: 15

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro His
                85                  90                  95

Thr Phe Gly Gln Gly Thr Lys Leu Glu Ile Lys
            100                 105

<210> SEQ ID NO 16
<211> LENGTH: 5
<212> TYPE: PRT
<213> ORGANISM: Homo sapiens

<400> SEQUENCE: 16

Ser Ser Trp Ile Gly
 1               5

<210> SEQ ID NO 17
<211> LENGTH: 5
<212> TYPE: PRT
<213> ORGANISM: Homo sapiens

<400> SEQUENCE: 17

Ser Tyr Ala Ile Ser

-continued

```
<210> SEQ ID NO 18
<211> LENGTH: 5
<212> TYPE: PRT
<213> ORGANISM: Homo sapiens

<400> SEQUENCE: 18

Ser Tyr Trp Ile Ala
 1               5

<210> SEQ ID NO 19
<211> LENGTH: 5
<212> TYPE: PRT
<213> ORGANISM: Homo sapiens

<400> SEQUENCE: 19

Ser Tyr Thr Ile Asn
 1               5

<210> SEQ ID NO 20
<211> LENGTH: 5
<212> TYPE: PRT
<213> ORGANISM: Homo sapiens

<400> SEQUENCE: 20

Ser Tyr Trp Ile Gly
 1               5

<210> SEQ ID NO 21
<211> LENGTH: 5
<212> TYPE: PRT
<213> ORGANISM: Homo sapiens

<400> SEQUENCE: 21

Asn Tyr Trp Ile Ala
 1               5

<210> SEQ ID NO 22
<211> LENGTH: 5
<212> TYPE: PRT
<213> ORGANISM: Homo sapiens

<400> SEQUENCE: 22

Asn Tyr Trp Ile Ala
 1               5

<210> SEQ ID NO 23
<211> LENGTH: 17
<212> TYPE: PRT
<213> ORGANISM: Homo sapiens

<400> SEQUENCE: 23

Ile Ile Tyr Pro Asp Asp Ser Asp Thr Arg Tyr Ser Pro Ser Phe Gln
 1               5                  10                  15

Gly

<210> SEQ ID NO 24
<211> LENGTH: 17
<212> TYPE: PRT
<213> ORGANISM: Homo sapiens

<400> SEQUENCE: 24

Gly Ile Ile Pro Ile Phe Gly Thr Thr Asn Tyr Ala Gln Gln Phe Gln
 1               5                  10                  15
```

Gly

<210> SEQ ID NO 25
<211> LENGTH: 17
<212> TYPE: PRT
<213> ORGANISM: Homo sapiens

<400> SEQUENCE: 25

Ile Ile Tyr Pro Gly Asp Ser Asp Thr Arg Tyr Ser Pro Ser Phe Gln
1               5                   10                  15

Gly

<210> SEQ ID NO 26
<211> LENGTH: 17
<212> TYPE: PRT
<213> ORGANISM: Homo sapiens

<400> SEQUENCE: 26

Gly Ile Ile Pro Ile Phe Gly Ile Pro Asn Tyr Ala Gln Lys Phe Gln
1               5                   10                  15

Gly

<210> SEQ ID NO 27
<211> LENGTH: 17
<212> TYPE: PRT
<213> ORGANISM: Homo sapiens

<400> SEQUENCE: 27

Ile Ile Tyr Pro Gly Asp Ser Asp Thr Arg Tyr Ser Pro Ser Phe Gln
1               5                   10                  15

Gly

<210> SEQ ID NO 28
<211> LENGTH: 17
<212> TYPE: PRT
<213> ORGANISM: Homo sapiens

<400> SEQUENCE: 28

Ile Ile Tyr Pro Gly Asp Ser Asp Thr Arg Tyr Ser Pro Ser Phe Gln
1               5                   10                  15

Gly

<210> SEQ ID NO 29
<211> LENGTH: 17
<212> TYPE: PRT
<213> ORGANISM: Homo sapiens

<400> SEQUENCE: 29

Ile Ile Tyr Pro Gly Asp Ser Asp Thr Arg Tyr Ser Pro Ser Phe Gln
1               5                   10                  15

Gly

<210> SEQ ID NO 30
<211> LENGTH: 12
<212> TYPE: PRT
<213> ORGANISM: Homo sapiens

<400> SEQUENCE: 30

His Val Thr Met Ile Trp Gly Val Ile Ile Asp Phe
1               5                   10

```
<210> SEQ ID NO 31
<211> LENGTH: 10
<212> TYPE: PRT
<213> ORGANISM: Homo sapiens

<400> SEQUENCE: 31

Glu Ala Val Ala Ala Asp Trp Leu Asp Pro
1               5                   10

<210> SEQ ID NO 32
<211> LENGTH: 15
<212> TYPE: PRT
<213> ORGANISM: Homo sapiens

<400> SEQUENCE: 32

Gln Gly Tyr Ser Ser Gly Trp Asp Ser Tyr Tyr Gly Met Gly Val
1               5                   10                  15

<210> SEQ ID NO 33
<211> LENGTH: 14
<212> TYPE: PRT
<213> ORGANISM: Homo sapiens

<400> SEQUENCE: 33

Ala Ser Gly Gly Ser Ala Asp Tyr Ser Tyr Gly Met Asp Val
1               5                   10

<210> SEQ ID NO 34
<211> LENGTH: 12
<212> TYPE: PRT
<213> ORGANISM: Homo sapiens

<400> SEQUENCE: 34

Gly Val Ser Met Ile Trp Gly Val Ile Met Asp Val
1               5                   10

<210> SEQ ID NO 35
<211> LENGTH: 15
<212> TYPE: PRT
<213> ORGANISM: Homo sapiens

<400> SEQUENCE: 35

Gln Gly Tyr Ser Ser Gly Trp Arg Ser Tyr Tyr Gly Met Gly Val
1               5                   10                  15

<210> SEQ ID NO 36
<211> LENGTH: 15
<212> TYPE: PRT
<213> ORGANISM: Homo sapiens

<400> SEQUENCE: 36

Gln Gly Tyr Ser Ser Gly Trp Arg Ser Tyr Tyr Gly Met Gly Val
1               5                   10                  15

<210> SEQ ID NO 37
<211> LENGTH: 11
<212> TYPE: PRT
<213> ORGANISM: Homo sapiens

<400> SEQUENCE: 37

Arg Ala Ser Gln Gly Ile Ser Ser Ala Leu Ala
1               5                   10

<210> SEQ ID NO 38
<211> LENGTH: 12
<212> TYPE: PRT
```

<213> ORGANISM: Homo sapiens

<400> SEQUENCE: 38

Arg Ala Ser Gln Ser Val Ser Ser Tyr Leu Ala
 1               5                  10

<210> SEQ ID NO 39
<211> LENGTH: 11
<212> TYPE: PRT
<213> ORGANISM: Homo sapiens

<400> SEQUENCE: 39

Arg Ala Ser Gln Gly Ile Ser Ser Ala Leu Ala
 1               5                  10

<210> SEQ ID NO 40
<211> LENGTH: 11
<212> TYPE: PRT
<213> ORGANISM: Homo sapiens

<400> SEQUENCE: 40

Arg Ala Ser Gln Gly Ile Ser Ser Trp Leu Ala
 1               5                  10

<210> SEQ ID NO 41
<211> LENGTH: 11
<212> TYPE: PRT
<213> ORGANISM: Homo sapiens

<400> SEQUENCE: 41

Arg Ala Ser Gln Gly Ile Ser Ser Ala Leu Ala
 1               5                  10

<210> SEQ ID NO 42
<211> LENGTH: 11
<212> TYPE: PRT
<213> ORGANISM: Homo sapiens

<400> SEQUENCE: 42

Arg Ala Ser Gln Gly Ile Ser Ser Ala Leu Ala
 1               5                  10

<210> SEQ ID NO 43
<211> LENGTH: 11
<212> TYPE: PRT
<213> ORGANISM: Homo sapiens

<400> SEQUENCE: 43

Arg Ala Ser Gln Gly Ile Ser Ser Ala Leu Ala
 1               5                  10

<210> SEQ ID NO 44
<211> LENGTH: 7
<212> TYPE: PRT
<213> ORGANISM: Homo sapiens

<400> SEQUENCE: 44

Asp Ala Ser Ser Leu Glu Ser
 1               5

<210> SEQ ID NO 45
<211> LENGTH: 7
<212> TYPE: PRT
<213> ORGANISM: Homo sapiens

<400> SEQUENCE: 45

```
Gly Ala Ser Ser Arg Ala Thr
  1               5
```

<210> SEQ ID NO 46
<211> LENGTH: 7
<212> TYPE: PRT
<213> ORGANISM: Homo sapiens
<400> SEQUENCE: 46

```
Asp Ala Ser Ser Leu Glu Ser
  1               5
```

<210> SEQ ID NO 47
<211> LENGTH: 7
<212> TYPE: PRT
<213> ORGANISM: Homo sapiens
<400> SEQUENCE: 47

```
Ala Ala Ser Ser Leu Gln Ser
  1               5
```

<210> SEQ ID NO 48
<211> LENGTH: 7
<212> TYPE: PRT
<213> ORGANISM: Homo sapiens
<400> SEQUENCE: 48

```
Asp Ala Ser Ser Leu Glu Ser
  1               5
```

<210> SEQ ID NO 49
<211> LENGTH: 7
<212> TYPE: PRT
<213> ORGANISM: Homo sapiens
<400> SEQUENCE: 49

```
Asp Ala Ser Ser Leu Glu Ser
  1               5
```

<210> SEQ ID NO 50
<211> LENGTH: 7
<212> TYPE: PRT
<213> ORGANISM: Homo sapiens
<400> SEQUENCE: 50

```
Asp Ala Ser Ser Leu Glu Ser
  1               5
```

<210> SEQ ID NO 51
<211> LENGTH: 9
<212> TYPE: PRT
<213> ORGANISM: Homo sapiens
<400> SEQUENCE: 51

```
Gln Gln Phe Asn Ser Tyr Pro Tyr Thr
  1               5
```

<210> SEQ ID NO 52
<211> LENGTH: 9
<212> TYPE: PRT
<213> ORGANISM: Homo sapiens
<400> SEQUENCE: 52

```
Gln Gln Phe Asn Ser Tyr Pro Phe Thr
  1               5
```

<210> SEQ ID NO 53
<211> LENGTH: 9
<212> TYPE: PRT
<213> ORGANISM: Homo sapiens

<400> SEQUENCE: 53

Gln Gln Tyr Gly Ser Ser Arg Phe Thr
1               5

<210> SEQ ID NO 54
<211> LENGTH: 9
<212> TYPE: PRT
<213> ORGANISM: Homo sapiens

<400> SEQUENCE: 54

Gln Gln Phe Asn Ser Tyr Pro Tyr Thr
1               5

<210> SEQ ID NO 55
<211> LENGTH: 9
<212> TYPE: PRT
<213> ORGANISM: Homo sapiens

<400> SEQUENCE: 55

Gln Gln Tyr Lys Arg Tyr Pro Tyr Thr
1               5

<210> SEQ ID NO 56
<211> LENGTH: 9
<212> TYPE: PRT
<213> ORGANISM: Homo sapiens

<400> SEQUENCE: 56

Gln Gln Phe Asn Ser Tyr Pro Trp Thr
1               5

<210> SEQ ID NO 57
<211> LENGTH: 9
<212> TYPE: PRT
<213> ORGANISM: Homo sapiens

<400> SEQUENCE: 57

Gln Gln Phe Asn Ser Tyr Pro His Thr
1               5

<210> SEQ ID NO 58
<211> LENGTH: 9
<212> TYPE: PRT
<213> ORGANISM: Homo sapiens

<400> SEQUENCE: 58

Gln Gln Phe Asn Ser Tyr Pro His Thr
1               5

<210> SEQ ID NO 59
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 59 gag gtg cag ctg gtg cag tct gga gca gag gtg aaa aag ccc ggg gag        48
Glu Val Gln Leu Val Gln Ser Gly Ala Glu Val Lys Lys Pro Gly Glu

```
tct ctg aag atc tcc tgt aag ggt tct gga tac agc ttt agc agc agc      96
Ser Leu Lys Ile Ser Cys Lys Gly Ser Gly Tyr Ser Phe Ser Ser Ser
            20                  25                  30 tgg atc ggc tgg gtg cgc cag atg ccc ggg aaa ggc ctg gag tgg atg     144
Trp Ile Gly Trp Val Arg Gln Met Pro Gly Lys Gly Leu Glu Trp Met
        35                  40                  45 ggg atc atc tat cct gat gac tct gat acc aga tac agt ccg tcc ttc     192
Gly Ile Ile Tyr Pro Asp Asp Ser Asp Thr Arg Tyr Ser Pro Ser Phe
    50                  55                  60 caa ggc cag gtc acc atc tca gcc gac aag tcc atc agg acc gcc tac     240
Gln Gly Gln Val Thr Ile Ser Ala Asp Lys Ser Ile Arg Thr Ala Tyr
65                  70                  75                  80 ctg cag tgg agc agc ctg aag gcc tcg gac acc gcc atg tat tac tgt     288
Leu Gln Trp Ser Ser Leu Lys Ala Ser Asp Thr Ala Met Tyr Tyr Cys
                85                  90                  95 gcg aga cat gtt act atg att tgg gga gtt att att gac ttc tgg ggc     336
Ala Arg His Val Thr Met Ile Trp Gly Val Ile Ile Asp Phe Trp Gly
            100                 105                 110 cag gga acc ctg gtc acc gtc tcc tca                                 363
Gln Gly Thr Leu Val Thr Val Ser Ser
        115                 120

<210> SEQ ID NO 60
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 60 cag gtc cag ctg gtg cag tct ggg gct gag gtg aag aag cct ggg tcc      48
Gln Val Gln Leu Val Gln Ser Gly Ala Glu Val Lys Lys Pro Gly Ser
1               5                   10                  15 tcg gtg aag gtc tcc tgc aag gac tct gga ggc acc ttc agc agc tat      96
Ser Val Lys Val Ser Cys Lys Asp Ser Gly Gly Thr Phe Ser Ser Tyr
            20                  25                  30 gct atc agc tgg gtg cga cag gcc cct gga caa gga ctt gag tgg atg     144
Ala Ile Ser Trp Val Arg Gln Ala Pro Gly Gln Gly Leu Glu Trp Met
        35                  40                  45 gga ggg atc atc cct atc ttt ggt aca aca aac tac gca cag cag ttc     192
Gly Gly Ile Ile Pro Ile Phe Gly Thr Thr Asn Tyr Ala Gln Gln Phe
    50                  55                  60 cag ggc aga gtc acg att acc gcg gac gaa tcc acg agc aca gcc tac     240
Gln Gly Arg Val Thr Ile Thr Ala Asp Glu Ser Thr Ser Thr Ala Tyr
65                  70                  75                  80 atg gag ctg agc agt ctg aga tct gag gac acg gcc gtg tat tac tgt     288
Met Glu Leu Ser Ser Leu Arg Ser Glu Asp Thr Ala Val Tyr Tyr Cys
                85                  90                  95 gcg aga gaa gca gta gct gcg gac tgg tta gac ccc tgg ggc cag gga     336
Ala Arg Glu Ala Val Ala Ala Asp Trp Leu Asp Pro Trp Gly Gln Gly
            100                 105                 110 acc ctg gtc acc gtc tcc tca                                         357
Thr Leu Val Thr Val Ser Ser
        115

<210> SEQ ID NO 61
<211> LENGTH: 372
<212> TYPE: DNA
<213> ORGANISM: Homo sapiens
<220> FEATURE:
<221> NAME/KEY: CDS
```

<222> LOCATION: (1)..(372)

<400> SEQUENCE: 61

```
gag gtg cag ctg gtg cag tct gga gca gag gtg aaa aag ccc ggg gag      48
Glu Val Gln Leu Val Gln Ser Gly Ala Glu Val Lys Lys Pro Gly Glu
 1               5                  10                  15 tct ctg aag atc tcc tgt aag ggt tct gga tac agc ttt acc agc tac      96
Ser Leu Lys Ile Ser Cys Lys Gly Ser Gly Tyr Ser Phe Thr Ser Tyr
             20                  25                  30 tgg atc gcc tgg gtg cgc cag atg ccc ggg aaa ggc ctg gag tgg atg     144
Trp Ile Ala Trp Val Arg Gln Met Pro Gly Lys Gly Leu Glu Trp Met
         35                  40                  45 ggg atc atc tat cct ggt gac tct gat acc aga tac agc ccg tcc ttc     192
Gly Ile Ile Tyr Pro Gly Asp Ser Asp Thr Arg Tyr Ser Pro Ser Phe
     50                  55                  60 caa ggc cag gtc acc atc tca gcc gac aag tcc atc agc acc gcc tac     240
Gln Gly Gln Val Thr Ile Ser Ala Asp Lys Ser Ile Ser Thr Ala Tyr
 65                  70                  75                  80 ctg cag tgg agc agc ctg aag gcc tcg gac acc gcc atg tat tac tgt     288
Leu Gln Trp Ser Ser Leu Lys Ala Ser Asp Thr Ala Met Tyr Tyr Cys
                 85                  90                  95 gcg aga cag ggg tat agc agt ggc tgg gac tcc tac tac ggt atg ggc     336
Ala Arg Gln Gly Tyr Ser Ser Gly Trp Asp Ser Tyr Tyr Gly Met Gly
            100                 105                 110 gtc tgg ggc caa ggg acc acg gtc acc gtc tcc tca                     372
Val Trp Gly Gln Gly Thr Thr Val Thr Val Ser Ser
        115                 120
```

<210> SEQ ID NO 62
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 62

```
cag gtc cag ctg gtg cag tct ggg gct gag gtg aag aag cct ggg tcc      48
Gln Val Gln Leu Val Gln Ser Gly Ala Glu Val Lys Lys Pro Gly Ser
 1               5                  10                  15 tcg gtg aag gtc tcc tgc aag gct tct gga ggc acc ttc agc agc tat      96
Ser Val Lys Val Ser Cys Lys Ala Ser Gly Gly Thr Phe Ser Ser Tyr
             20                  25                  30 act atc aac tgg gtg cga cag gcc cct gga caa ggg ctt gag tgg atg     144
Thr Ile Asn Trp Val Arg Gln Ala Pro Gly Gln Gly Leu Glu Trp Met
         35                  40                  45 gga ggg atc att cct atc ttt ggt ata cct aac tac gca cag aag ttc     192
Gly Gly Ile Ile Pro Ile Phe Gly Ile Pro Asn Tyr Ala Gln Lys Phe
     50                  55                  60 cag ggt aga gtt acg att acc gcg gac gaa tcc acg aac aca gcc tac     240
Gln Gly Arg Val Thr Ile Thr Ala Asp Glu Ser Thr Asn Thr Ala Tyr
 65                  70                  75                  80 atg gag ctg agc agc ctg aga gct gag gac acg gcc gtt tat tac tgt     288
Met Glu Leu Ser Ser Leu Arg Ala Glu Asp Thr Ala Val Tyr Tyr Cys
                 85                  90                  95 gcg aga gcc agt ggt ggg agc gcg gac tat tcc tac ggt atg gac gtc     336
Ala Arg Ala Ser Gly Gly Ser Ala Asp Tyr Ser Tyr Gly Met Asp Val
            100                 105                 110 tgg ggc caa ggg acc gcg gtc acc gtc tcc tca                         369
Trp Gly Gln Gly Thr Ala Val Thr Val Ser Ser
        115                 120
```

<210> SEQ ID NO 63
<211> LENGTH: 363
<212> TYPE: DNA
<213> ORGANISM: Homo sapiens
<220> FEATURE:
<221> NAME/KEY: CDS
<222> LOCATION: (1)..(363)

<400> SEQUENCE: 63

| gag gtg cag ctg gtg cag tct gga gca gag gtg aaa aag ccc ggg gag | 48 |
| Glu Val Gln Leu Val Gln Ser Gly Ala Glu Val Lys Lys Pro Gly Glu | |
| 1               5                   10                  15 | |

| tct ctg aac atc tcc tgt aag ggt tct gga tac agc ttt acc agc tac | 96 |
| Ser Leu Asn Ile Ser Cys Lys Gly Ser Gly Tyr Ser Phe Thr Ser Tyr | |
|             20                  25                  30 | |

| tgg atc ggc tgg gtg cgc cag atg ccc ggg aaa ggc ctg gag tgg atg | 144 |
| Trp Ile Gly Trp Val Arg Gln Met Pro Gly Lys Gly Leu Glu Trp Met | |
|         35                  40                  45 | |

| ggg atc atc tat cct ggt gac tct gat acc aga tac agc ccg tcc ttc | 192 |
| Gly Ile Ile Tyr Pro Gly Asp Ser Asp Thr Arg Tyr Ser Pro Ser Phe | |
|     50                  55                  60 | |

| caa ggc cag gtc acc atc tca gcc gac aag tcc atc aac acc gcc tac | 240 |
| Gln Gly Gln Val Thr Ile Ser Ala Asp Lys Ser Ile Asn Thr Ala Tyr | |
| 65                  70                  75                  80 | |

| ctg cag tgg agc agc ctg aag gcc tcg gac acc gcc atg tat tac tgt | 288 |
| Leu Gln Trp Ser Ser Leu Lys Ala Ser Asp Thr Ala Met Tyr Tyr Cys | |
|                 85                  90                  95 | |

| gcg aga ggg gtt tct atg att tgg gga gtt att atg gac gtc tgg ggc | 336 |
| Ala Arg Gly Val Ser Met Ile Trp Gly Val Ile Met Asp Val Trp Gly | |
|             100                 105                 110 | |

| caa ggg acc acg gtc acc gtc tcc tca | 363 |
| Gln Gly Thr Thr Val Thr Val Ser Ser | |
|         115                 120 | |

<210> SEQ ID NO 64
<211> LENGTH: 372
<212> TYPE: DNA
<213> ORGANISM: Homo sapiens
<220> FEATURE:
<221> NAME/KEY: CDS
<222> LOCATION: (1)..(372)

<400> SEQUENCE: 64

| gag gtg cag ctg gtg cag tct gga gca gag gtg aaa aag ccc ggg gag | 48 |
| Glu Val Gln Leu Val Gln Ser Gly Ala Glu Val Lys Lys Pro Gly Glu | |
| 1               5                   10                  15 | |

| tct ctg cag atc tcc tgt aag ggt tct gga tac acc ttt acc aac tac | 96 |
| Ser Leu Gln Ile Ser Cys Lys Gly Ser Gly Tyr Thr Phe Thr Asn Tyr | |
|             20                  25                  30 | |

| tgg atc gcc tgg gtg cgc cag atg ccc ggg aaa ggc ctg gag tgg atg | 144 |
| Trp Ile Ala Trp Val Arg Gln Met Pro Gly Lys Gly Leu Glu Trp Met | |
|         35                  40                  45 | |

| ggg atc atc tat cct ggt gac tct gat acc aga tac agc ccg tcc ttc | 192 |
| Gly Ile Ile Tyr Pro Gly Asp Ser Asp Thr Arg Tyr Ser Pro Ser Phe | |
|     50                  55                  60 | |

| caa ggc cag gtc acc atc tca gcc gac aag tcc atc agc acc gcc tac | 240 |
| Gln Gly Gln Val Thr Ile Ser Ala Asp Lys Ser Ile Ser Thr Ala Tyr | |
| 65                  70                  75                  80 | |

| cta cag tgg agc ggc ctg aag gcc tcg gac acc gcc atg tat tac tgt | 288 |
| Leu Gln Trp Ser Gly Leu Lys Ala Ser Asp Thr Ala Met Tyr Tyr Cys | |
|                 85                  90                  95 | |

| gcg aga cag gga tat agc agt ggc tgg cgc tcc tac tac ggt atg ggc | 336 |
| Ala Arg Gln Gly Tyr Ser Ser Gly Trp Arg Ser Tyr Tyr Gly Met Gly | |
|             100                 105                 110 | |

```
gtc tgg ggc caa ggg acc acg gtc acc gtc tcc tca                    372
Val Trp Gly Gln Gly Thr Thr Val Thr Val Ser Ser
            115                 120
```

<210> SEQ ID NO 65
<211> LENGTH: 372
<212> TYPE: DNA
<213> ORGANISM: Homo sapiens
<220> FEATURE:
<221> NAME/KEY: CDS
<222> LOCATION: (1)..(372)

<400> SEQUENCE: 65

```
gag gtg cag ctg gtg cag tct gga gca gag gtg aaa aag ccc ggg gag     48
Glu Val Gln Leu Val Gln Ser Gly Ala Glu Val Lys Lys Pro Gly Glu
  1               5                  10                  15 tct ctg cag atc tcc tgt aag ggt tct gga tac acc ttt acc aac tac     96
Ser Leu Gln Ile Ser Cys Lys Gly Ser Gly Tyr Thr Phe Thr Asn Tyr
             20                  25                  30 tgg atc gcc tgg gtg cgc cag atg ccc ggg aaa ggc ctg gag tgg atg    144
Trp Ile Ala Trp Val Arg Gln Met Pro Gly Lys Gly Leu Glu Trp Met
         35                  40                  45 ggg atc atc tat cct ggt gac tct gat acc aga tac agc ccg tcc ttc    192
Gly Ile Ile Tyr Pro Gly Asp Ser Asp Thr Arg Tyr Ser Pro Ser Phe
     50                  55                  60 caa ggc cag gtc acc atc tca gcc gac aag tcc atc agc acc gcc tac    240
Gln Gly Gln Val Thr Ile Ser Ala Asp Lys Ser Ile Ser Thr Ala Tyr
 65                  70                  75                  80 cta cag tgg agc ggc ctg aag gcc tcg gac acc gcc atg tat tac tgt    288
Leu Gln Trp Ser Gly Leu Lys Ala Ser Asp Thr Ala Met Tyr Tyr Cys
                 85                  90                  95 gcg aga cag gga tat agc agt ggc tgg cgc tcc tac tac ggt atg ggc    336
Ala Arg Gln Gly Tyr Ser Ser Gly Trp Arg Ser Tyr Tyr Gly Met Gly
            100                 105                 110 gtc tgg ggc caa ggg acc acg gtc acc gtc tcc tca                    372
Val Trp Gly Gln Gly Thr Thr Val Thr Val Ser Ser
            115                 120
```

<210> SEQ ID NO 66
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 66

```
gcc atc cag ttg acc cag tct cca tcc tcc ctg tct gca tct gta gga     48
Ala Ile Gln Leu Thr Gln Ser Pro Ser Ser Leu Ser Ala Ser Val Gly
  1               5                  10                  15 gac aga gtc acc atc act tgc cgg gca agt cag ggc att agc agt gct     96
Asp Arg Val Thr Ile Thr Cys Arg Ala Ser Gln Gly Ile Ser Ser Ala
             20                  25                  30 tta gcc tgg tat cag cag aaa cca ggg aaa gct cct aag ctc ctg atc    144
Leu Ala Trp Tyr Gln Gln Lys Pro Gly Lys Ala Pro Lys Leu Leu Ile
         35                  40                  45 tat gat gcc tcc agt ttg gaa agt ggg gtc cca tca agg ttc agc ggc    192
Tyr Asp Ala Ser Ser Leu Glu Ser Gly Val Pro Ser Arg Phe Ser Gly
     50                  55                  60 agt gga tct ggg aca gat ttc act ctc acc atc agc agc ctg cag cct    240
Ser Gly Ser Gly Thr Asp Phe Thr Leu Thr Ile Ser Ser Leu Gln Pro
 65                  70                  75                  80 gaa gat ttt gca act tat tac tgt caa cag ttt aat agt tac ccg tac    288
Glu Asp Phe Ala Thr Tyr Tyr Cys Gln Gln Phe Asn Ser Tyr Pro Tyr
```

```
Glu Asp Phe Ala Thr Tyr Tyr Cys Gln Gln Phe Asn Ser Tyr Pro Tyr
                85                  90                  95 act ttt ggc cag ggg acc aag ctg gag atc aaa                          321
Thr Phe Gly Gln Gly Thr Lys Leu Glu Ile Lys
            100                 105

<210> SEQ ID NO 67
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 67 gcc atc cag ttg acc cag tct cca tcc tcc ctg tct gca tct gta gga     48
Ala Ile Gln Leu Thr Gln Ser Pro Ser Ser Leu Ser Ala Ser Val Gly
1               5                   10                  15 gac aga gtc acc atc act tgc cgg gca agt cag ggc att agc agt gct     96
Asp Arg Val Thr Ile Thr Cys Arg Ala Ser Gln Gly Ile Ser Ser Ala
                20                  25                  30 tta gcc tgg tat cag cag aaa cca ggg aaa gct cct aag ctc ctg atc    144
Leu Ala Trp Tyr Gln Gln Lys Pro Gly Lys Ala Pro Lys Leu Leu Ile
            35                  40                  45 tat gat gcc tcc agt ttg gaa agt ggg gtc cca tca agg ttc agc ggc    192
Tyr Asp Ala Ser Ser Leu Glu Ser Gly Val Pro Ser Arg Phe Ser Gly
        50                  55                  60 agt gga tct ggg aca gat ttc act ctc acc atc agc agc ctg cag cct    240
Ser Gly Ser Gly Thr Asp Phe Thr Leu Thr Ile Ser Ser Leu Gln Pro
65                  70                  75                  80 gaa gat ttt gca act tat tac tgt caa cag ttt aat agt tac cca ttc    288
Glu Asp Phe Ala Thr Tyr Tyr Cys Gln Gln Phe Asn Ser Tyr Pro Phe
                85                  90                  95 act ttc ggc cct ggg acc aaa gtg gat atc aaa                        321
Thr Phe Gly Pro Gly Thr Lys Val Asp Ile Lys
            100                 105

<210> SEQ ID NO 68
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 68 gaa att gtg ttg acg cag tct cca ggc acc ctg tct ttg tct cca ggg     48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc     96
Glu Arg Ala Thr Leu Ser Cys Arg Ala Ser Gln Ser Val Ser Ser Ser
                20                  25                  30 tac tta gcc tgg tac cag cag aaa cct ggc cag gct ccc agg ctc ctc    144
Tyr Leu Ala Trp Tyr Gln Gln Lys Pro Gly Gln Ala Pro Arg Leu Leu
            35                  40                  45 atc tat ggt gca tcc agc agg gcc act ggc atc cca gac agg ttc agt    192
Ile Tyr Gly Ala Ser Ser Arg Ala Thr Gly Ile Pro Asp Arg Phe Ser
        50                  55                  60 ggc agt ggg tct ggg aca gac ttc act ctc acc atc agc aga ctg gag    240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agc tca cga    288
Pro Glu Asp Phe Ala Val Tyr Tyr Cys Gln Gln Tyr Gly Ser Ser Arg
                85                  90                  95
```

```
ttc act ttc ggc cct ggg acc aaa gtg gat atc aaa              324
Phe Thr Phe Gly Pro Gly Thr Lys Val Asp Ile Lys
            100                 105
```

<210> SEQ ID NO 69
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 69

```
gcc atc cag ttg acc cag tct cca tcc tcc ctg tct gca tct gta gga    48
Ala Ile Gln Leu Thr Gln Ser Pro Ser Ser Leu Ser Ala Ser Val Gly
  1               5                  10                  15 gac aga gtc acc atc act tgc cgg gca agt cag ggc att agc agt gct    96
Asp Arg Val Thr Ile Thr Cys Arg Ala Ser Gln Gly Ile Ser Ser Ala
                 20                  25                  30 tta gcc tgg tat cag cag aaa cca ggg aaa gct cct aag ctc ctg atc   144
Leu Ala Trp Tyr Gln Gln Lys Pro Gly Lys Ala Pro Lys Leu Leu Ile
             35                  40                  45 tat gat gcc tcc agt ttg gaa agt ggg gtc cca tca agg ttc agc ggc   192
Tyr Asp Ala Ser Ser Leu Glu Ser Gly Val Pro Ser Arg Phe Ser Gly
         50                  55                  60 agt gga tct ggg aca gat ttc act ctc acc atc agc agc ctg cag cct   240
Ser Gly Ser Gly Thr Asp Phe Thr Leu Thr Ile Ser Ser Leu Gln Pro
 65                  70                  75                  80 gaa gat ttt gca act tat tac tgt caa cag ttt aat agt tac ccg tac   288
Glu Asp Phe Ala Thr Tyr Tyr Cys Gln Gln Phe Asn Ser Tyr Pro Tyr
                 85                  90                  95 act ttt ggc cag ggg acc aag ctg gag atc aaa                       321
Thr Phe Gly Gln Gly Thr Lys Leu Glu Ile Lys
                100                 105
```

<210> SEQ ID NO 70
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 70

```
gac atc cag atg acc cag tct cca tcc tca ctg tct gca tct gta gga    48
Asp Ile Gln Met Thr Gln Ser Pro Ser Ser Leu Ser Ala Ser Val Gly
  1               5                  10                  15 gac aga gtc acc atc act tgt cgg gcg agt cag ggt att agc agc tgg    96
Asp Arg Val Thr Ile Thr Cys Arg Ala Ser Gln Gly Ile Ser Ser Trp
                 20                  25                  30 tta gcc tgg tat cag cag aaa cca gag aaa gcc cct aag tcc ctg atc   144
Leu Ala Trp Tyr Gln Gln Lys Pro Glu Lys Ala Pro Lys Ser Leu Ile
             35                  40                  45 tat gct gca tcc agt ttg caa agt ggg gtc cca tca agg ttc agc ggc   192
Tyr Ala Ala Ser Ser Leu Gln Ser Gly Val Pro Ser Arg Phe Ser Gly
         50                  55                  60 agt gga tct ggg aca gat ttc act ctc acc atc agc agc ctg cag cct   240
Ser Gly Ser Gly Thr Asp Phe Thr Leu Thr Ile Ser Ser Leu Gln Pro
 65                  70                  75                  80 gaa gat ttt gca act tac tac tgc caa cag tat aag aga tac ccg tac   288
Glu Asp Phe Ala Thr Tyr Tyr Cys Gln Gln Tyr Lys Arg Tyr Pro Tyr
                 85                  90                  95 act ttt ggc cag ggg acc aag ctg gag atc aaa                       321
```

```
Thr Phe Gly Gln Gly Thr Lys Leu Glu Ile Lys
            100                 105

<210> SEQ ID NO 71
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 71 gcc atc cag ttg acc cag tct cca tcc tcc ctg tct gca tct gta gga    48
Ala Ile Gln Leu Thr Gln Ser Pro Ser Ser Leu Ser Ala Ser Val Gly
1               5                   10                  15 gac aga gtc acc atc act tgc cgg gca agt cag ggc att agc agt gct    96
Asp Arg Val Thr Ile Thr Cys Arg Ala Ser Gln Gly Ile Ser Ser Ala
            20                  25                  30 tta gcc tgg tat cag cag aaa cca ggg aaa gct cct aag ctc ctg atc   144
Leu Ala Trp Tyr Gln Gln Lys Pro Gly Lys Ala Pro Lys Leu Leu Ile
        35                  40                  45 tat gat gcc tcc agt ttg gaa agt ggg gtc cca tca agg ttc agc ggc   192
Tyr Asp Ala Ser Ser Leu Glu Ser Gly Val Pro Ser Arg Phe Ser Gly
    50                  55                  60 agt gga tct ggg aca gat ttc act ctc acc atc agc agc ctg cag cct   240
Ser Gly Ser Gly Thr Asp Phe Thr Leu Thr Ile Ser Ser Leu Gln Pro
65                  70                  75                  80 gaa gat ttt gca act tat tac tgt caa cag ttt aat agt tac ccg tgg   288
Glu Asp Phe Ala Thr Tyr Tyr Cys Gln Gln Phe Asn Ser Tyr Pro Trp
                85                  90                  95 acg ttc ggc caa ggg acc aag gtg gaa atc aaa                       321
Thr Phe Gly Gln Gly Thr Lys Val Glu Ile Lys
            100                 105

<210> SEQ ID NO 72
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 72 gcc atc cag ttg acc cag tct cca tcc tcc ctg tct gca tct gta gga    48
Ala Ile Gln Leu Thr Gln Ser Pro Ser Ser Leu Ser Ala Ser Val Gly
1               5                   10                  15 gac aga gtc acc atc act tgc cgg gca agt cag ggc att agc agt gct    96
Asp Arg Val Thr Ile Thr Cys Arg Ala Ser Gln Gly Ile Ser Ser Ala
            20                  25                  30 tta gcc tgg tat cag cag aaa cca ggg aaa gct cct aag ctc ctg atc   144
Leu Ala Trp Tyr Gln Gln Lys Pro Gly Lys Ala Pro Lys Leu Leu Ile
        35                  40                  45 tat gat gcc tcc agt ttg gaa agt ggg gtc cca tca agg ttc agc ggc   192
Tyr Asp Ala Ser Ser Leu Glu Ser Gly Val Pro Ser Arg Phe Ser Gly
    50                  55                  60 agt gga tct ggg aca gat ttc act ctc acc atc agc agc ctg cag cct   240
Ser Gly Ser Gly Thr Asp Phe Thr Leu Thr Ile Ser Ser Leu Gln Pro
65                  70                  75                  80 gaa gat ttt gca act tat tac tgt caa cag ttt aat agt tac cct cac   288
Glu Asp Phe Ala Thr Tyr Tyr Cys Gln Gln Phe Asn Ser Tyr Pro His
                85                  90                  95 act ttt ggc cag ggg acc aag ctg gag atc aaa                       321
Thr Phe Gly Gln Gly Thr Lys Leu Glu Ile Lys
            100                 105
```

<210> SEQ ID NO 73
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 73

```
gcc atc cag ttg acc cag tct cca tcc tcc ctg tct gca tct gta gga      48
Ala Ile Gln Leu Thr Gln Ser Pro Ser Ser Leu Ser Ala Ser Val Gly
 1               5                  10                  15 gac aga gtc acc atc act tgc cgg gca agt cag ggc att agc agt gct      96
Asp Arg Val Thr Ile Thr Cys Arg Ala Ser Gln Gly Ile Ser Ser Ala
            20                  25                  30 tta gcc tgg tat cag cag aaa cca ggg aaa gct cct aag ctc ctg atc     144
Leu Ala Trp Tyr Gln Gln Lys Pro Gly Lys Ala Pro Lys Leu Leu Ile
        35                  40                  45 tat gat gcc tcc agt ttg gaa agt ggg gtc cca tca agg ttc agc ggc     192
Tyr Asp Ala Ser Ser Leu Glu Ser Gly Val Pro Ser Arg Phe Ser Gly
    50                  55                  60 agt gga tct ggg aca gat ttc act ctc acc atc agc agc ctg cag cct     240
Ser Gly Ser Gly Thr Asp Phe Thr Leu Thr Ile Ser Ser Leu Gln Pro
65                  70                  75                  80 gaa gat ttt gca act tat tac tgt caa cag ttt aat agt tac cct cac     288
Glu Asp Phe Ala Thr Tyr Tyr Cys Gln Gln Phe Asn Ser Tyr Pro His
                85                  90                  95 act ttt ggc cag ggg acc aag ctg gag atc aaa                         321
Thr Phe Gly Gln Gly Thr Lys Leu Glu Ile Lys
                100                 105
```

<210> SEQ ID NO 74
<211> LENGTH: 98
<212> TYPE: PRT
<213> ORGANISM: Homo sapiens

<400> SEQUENCE: 74

```
Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg
```

<210> SEQ ID NO 75
<211> LENGTH: 98
<212> TYPE: PRT
<213> ORGANISM: Homo sapiens

<400> SEQUENCE: 75

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
```

-continued

```
                    20                  25                  30
Ala Ile Ser Trp Val Arg Gln Ala Pro Gly Gln Gly Leu Glu Trp Met
                35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 76
<211> LENGTH: 95
<212> TYPE: PRT
<213> ORGANISM: Homo sapiens

<400> SEQUENCE: 76

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro
                 85                  90                  95

<210> SEQ ID NO 77
<211> LENGTH: 95
<212> TYPE: PRT
<213> ORGANISM: Homo sapiens

<400> SEQUENCE: 77

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser
                 85                  90                  95

<210> SEQ ID NO 78
<211> LENGTH: 95
<212> TYPE: PRT
<213> ORGANISM: Homo sapiens

<400> SEQUENCE: 78

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
```

```
                    20                  25                  30
Leu Ala Trp Tyr Gln Gln Lys Pro Glu Lys Ala Pro Lys Ser Leu Ile
            35                  40                  45
Tyr Ala Ala Ser Ser Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Ser Tyr Pro
                85                  90                  95

<210> SEQ ID NO 79
<211> LENGTH: 556
<212> TYPE: PRT
<213> ORGANISM: Homo sapiens

<400> SEQUENCE: 79

Met Pro Pro Pro Arg Leu Leu Phe Phe Leu Leu Phe Leu Thr Pro Met
1               5                   10                  15
Glu Val Arg Pro Glu Glu Pro Leu Val Val Lys Val Glu Glu Gly Asp
                20                  25                  30
Asn Ala Val Leu Gln Cys Leu Lys Gly Thr Ser Asp Gly Pro Thr Gln
            35                  40                  45
Gln Leu Thr Trp Ser Arg Glu Ser Pro Leu Lys Pro Phe Leu Lys Leu
        50                  55                  60
Ser Leu Gly Leu Pro Gly Leu Gly Ile His Met Arg Pro Leu Ala Ile
65                  70                  75                  80
Trp Leu Phe Ile Phe Asn Val Ser Gln Gln Met Gly Gly Phe Tyr Leu
                85                  90                  95
Cys Gln Pro Gly Pro Pro Ser Glu Lys Ala Trp Gln Pro Gly Trp Thr
                100                 105                 110
Val Asn Val Glu Gly Ser Gly Glu Leu Phe Arg Trp Asn Val Ser Asp
            115                 120                 125
Leu Gly Gly Leu Gly Cys Gly Leu Lys Asn Arg Ser Ser Glu Gly Pro
        130                 135                 140
Ser Ser Pro Ser Gly Lys Leu Met Ser Pro Lys Leu Tyr Val Trp Ala
145                 150                 155                 160
Lys Asp Arg Pro Glu Ile Trp Glu Gly Glu Pro Pro Cys Leu Pro Pro
                165                 170                 175
Arg Asp Ser Leu Asn Gln Ser Leu Ser Gln Asp Leu Thr Met Ala Pro
                180                 185                 190
Gly Ser Thr Leu Trp Leu Ser Cys Gly Val Pro Pro Asp Ser Val Ser
            195                 200                 205
Arg Gly Pro Leu Ser Trp Thr His Val His Pro Lys Gly Pro Lys Ser
        210                 215                 220
Leu Leu Ser Leu Glu Leu Lys Asp Asp Arg Pro Ala Arg Asp Met Trp
225                 230                 235                 240
Val Met Glu Thr Gly Leu Leu Leu Pro Arg Ala Thr Ala Gln Asp Ala
                245                 250                 255
Gly Lys Tyr Tyr Cys His Arg Gly Asn Leu Thr Met Ser Phe His Leu
                260                 265                 270
Glu Ile Thr Ala Arg Pro Val Leu Trp His Trp Leu Leu Arg Thr Gly
            275                 280                 285
Gly Trp Lys Val Ser Ala Val Thr Leu Ala Tyr Leu Ile Phe Cys Leu
        290                 295                 300
Cys Ser Leu Val Gly Ile Leu His Leu Gln Arg Ala Leu Val Leu Arg
```

```
                305                 310                 315                 320
Arg Lys Arg Lys Arg Met Thr Asp Pro Thr Arg Arg Phe Phe Lys Val
                    325                 330                 335

Thr Pro Pro Pro Gly Ser Gly Pro Gln Asn Gln Tyr Gly Asn Val Leu
                340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
        370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
        515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555

<210> SEQ ID NO 80
<211> LENGTH: 13
<212> TYPE: PRT
<213> ORGANISM: Homo sapiens

<400> SEQUENCE: 80

Asp Tyr Trp Gly Gln Gly Thr Leu Val Thr Val Ser Ser
1               5                   10

<210> SEQ ID NO 81
<211> LENGTH: 15
<212> TYPE: PRT
<213> ORGANISM: Homo sapiens

<400> SEQUENCE: 81

Trp Phe Asp Pro Trp Gly Gln Gly Thr Leu Val Thr Val Ser Ser
1               5                   10                  15

<210> SEQ ID NO 82
<211> LENGTH: 18
<212> TYPE: PRT
<213> ORGANISM: Homo sapiens

<400> SEQUENCE: 82

Tyr Tyr Tyr Gly Met Asp Val Trp Gly Gln Gly Thr Val Thr Val
1               5                   10                  15
```

```
<210> SEQ ID NO 83
<211> LENGTH: 14
<212> TYPE: PRT
<213> ORGANISM: Homo sapiens

<400> SEQUENCE: 83

Met Asp Val Trp Gly Gln Gly Thr Thr Val Thr Val Ser Ser
 1               5                  10

<210> SEQ ID NO 84
<211> LENGTH: 12
<212> TYPE: PRT
<213> ORGANISM: Homo sapiens

<400> SEQUENCE: 84

Tyr Thr Phe Gly Gln Gly Thr Lys Leu Glu Ile Lys
 1               5                  10

<210> SEQ ID NO 85
<211> LENGTH: 12
<212> TYPE: PRT
<213> ORGANISM: Homo sapiens

<400> SEQUENCE: 85

Phe Thr Phe Gly Pro Gly Thr Lys Val Asp Ile Lys
 1               5                  10

<210> SEQ ID NO 86
<211> LENGTH: 12
<212> TYPE: PRT
<213> ORGANISM: Homo sapiens

<400> SEQUENCE: 86

Trp Thr Phe Gly Gln Gly Thr Lys Val Glu Ile Lys
 1               5                  10

<210> SEQ ID NO 87
<211> LENGTH: 11
<212> TYPE: PRT
<213> ORGANISM: Homo sapiens

<400> SEQUENCE: 87

Thr Phe Gly Gln Gly Thr Lys Leu Glu Ile Lys
 1               5                  10
```

CD19 ANTIBODIES AND THEIR USES

CROSS-REFERENCE TO RELATED APPLICATIONS

This application is a national phase application of PCT International Application No. PCT/US2006/024183, filed Jun. 20, 2006, which claims the benefit of U.S. Provisional Patent Application No. 60/692,531, filed Jun. 20, 2005; U.S. Provisional Patent Application No. 60/748,956, filed Dec. 8, 2005; and U.S. Provisional Patent Application No. 60/804,083, filed Jun. 6, 2006; all of which are incorporated herein by reference in their entirety.

SEQUENCE LISTING

The specification further incorporates by reference the Sequence Listing submitted herewith via EFS on Dec. 14, 2007. Pursuant to 37 C.F.R. §1.52(e)(5), the Sequence Listing text file, identified as 0773750431.txt, is 59 KB and was created on Dec. 14, 2007. The Sequence Listing, electronically filed herewith, does not extend beyond the scope of the specification and thus does not contain new matter.

BACKGROUND

CD19 is a 95 kDa membrane receptor that is expressed early in B cell differentiation and continues to be expressed until the B cells are triggered to terminally differentiate (Pezzutto et al., (1987) *J Immunol.* 138:2793; Tedder et al. (1994) *Immunol Today* 15:437). The CD19 extracellular domain contains two C2-type immunoglobulin (IG)-like domains separated by a smaller potentially disulfide-linked domain. The CD19 cytoplasmic domain is structurally unique, but highly conserved between human, mouse, and guinea pig (Fujimoto et al, (1998) *Semin Immunol.* 10:267). CD19 is part of a protein complex found on the cell surface of B lymphocytes. The protein complex includes CD19, CD21 (complement receptor, type 2), CD81 (TAPA-1), and CD225 (Leu-13) (Fujimoto, supra).

CD19 is an important regulator of transmembrane signals in B cells. An increase or decrease in the cell surface density of CD19 affects B cell development and function, resulting in diseases such as autoimmunity or hypogammaglobulinemia (Fujimoto, supra). The CD19 complex potentiates the response of B cells to antigen in vivo through cross-linking of two separate signal transduction complexes found on B cell membranes. The two signal transduction complexes, associated with membrane IgM and CD19, activate phospholipase C (PLC) by different mechanisms. CD19 and B cell receptor cross-linking reduces the number of IgM molecules required to activate PLC (Fujimoto, supra; Ghetie, supra). Additionally, CD19 functions as a specialized adapter protein for the amplification of Arc family kinases (Hasegawa et al., (2001) *J Immunol* 167:3190).

CD19 binding has been shown to both enhance and inhibit B-cell activation and proliferation, depending on the amount of cross-linking that occurs (Tedder, supra). CD19 is expressed on greater than 90% of B-cell lymphomas and has been predicted to affect growth of lymphomas in vitro and in vivo (Ghetie, supra). Antibodies generated to CD19 have been murine antibodies. A disadvantage of using a murine antibody in treatment of human subjects is the human anti-mouse (HAMA) response on administration to the patient. Accordingly, the need exists for improved therapeutic antibodies against CD19 which are more effective for treating and/or preventing diseases mediated by CD19.

SUMMARY

The present invention provides isolated monoclonal antibodies, in particular human monoclonal antibodies, that bind to CD19 and that exhibit numerous desirable properties. These properties include high affinity binding to human CD19. Also provided are methods for treating a variety CD19 mediated diseases using the antibodies and compositions of the invention.

In one aspect, the invention pertains to an isolated monoclonal antibody, or an antigen-binding portion or fragment thereof wherein the antibody:
 (a) binds to human CD19 with a $K_D$ of $1 \times 10^{-7}$ M or less;
 (b) binds to Raji and Daudi B-cell tumor cells.

Preferably the antibody is a human antibody, although in alternative embodiments the antibody can be a murine antibody, a chimeric antibody or humanized antibody.

In one embodiment, the antibody binds to human CD19 with a $K_D$ of $5 \times 10^{-8}$ M or less, binds to human CD19 with a $K_D$ of $2 \times 10^{-8}$ M or less, binds to human CD19 with a $K_D$ of $1 \times 10^{-8}$ M or less, binds to human CD19 with a $K_D$ of $5 \times 10^{-9}$ M or less, binds to human CD19 with a $K_D$ of $4 \times 10^{-9}$ M or less, binds to human CD19 with a $K_D$ of $3 \times 10^{-9}$ M or less, or binds to human CD19 with a $K_D$ of $2 \times 10^{-9}$ M or less.

In another embodiment, the invention provides an isolated monoclonal antibody, or antigen binding portion thereof, wherein the antibody cross-competes for binding to CD19 with a reference antibody, wherein the antibody: (a) binds to human CD19 with a $K_D$ of $1 \times 10^{-7}$ M or less; and (b) binds to Raji and Daudi B-cell tumor cells. In various embodiments, the reference antibody comprises: (a) a heavy chain variable region comprising the amino acid sequence of SEQ ID NO: 1; and (b) a light chain variable region comprising the amino acid sequence of SEQ ID NO: 8;
 or the reference antibody comprises: (a) a heavy chain variable region comprising the amino acid sequence of SEQ ID NO: 1; and (b) a light chain variable region comprising the amino acid sequence of SEQ ID NO: 9;
 or the reference antibody comprises: (a) a heavy chain variable region comprising the amino acid sequence of SEQ ID NO: 2; and (b) a light chain variable region comprising the amino acid sequence of SEQ ID NO: 10;
 or the reference antibody comprises: (a) a heavy chain variable region comprising the amino acid sequence of SEQ ID NO: 3; and (b) a light chain variable region comprising the amino acid sequence of SEQ ID NO: 11;
 or the reference antibody comprises: (a) a heavy chain variable region comprising the amino acid sequence of SEQ ID NO: 4; and (b) a light chain variable region comprising the amino acid sequence of SEQ ID NO: 12;
 or the reference antibody comprises: (a) a heavy chain variable region comprising the amino acid sequence of SEQ ID NO: 5; and (b) a light chain variable region comprising the amino acid sequence of SEQ ID NO: 13;
 or the reference antibody comprises: (a) a heavy chain variable region comprising the amino acid sequence of SEQ ID NO: 6; and (b) a light chain variable region comprising the amino acid sequence of SEQ ID NO: 14;
 or the reference antibody comprises: (a) a heavy chain variable region comprising the amino acid sequence of SEQ ID NO: 7; and (b) a light chain variable region comprising the amino acid sequence of SEQ ID NO: 15.

In another aspect, the invention pertains to an isolated monoclonal antibody, or an antigen-binding portion or fragment thereof, comprising a heavy chain variable region that is the product of or derived from a human $V_H$ 5-51 gene, wherein the antibody specifically binds CD19. The invention also provides an isolated monoclonal antibody, or an antigen-binding portion or fragment thereof; comprising a heavy chain variable region that is the product of or derived from a human $V_H$ 1-69 gene, wherein the antibody specifically binds CD19. The invention still further provides an isolated monoclonal antibody, or an antigen-binding portion or fragment thereof; comprising a light chain variable region that is the product of or derived from a human $V_K$ L18 gene, wherein the antibody specifically binds CD19. The invention even further provides an isolated monoclonal antibody, or an antigen-binding portion or fragment thereof; comprising a light chain variable region that is the product of or derived from a human $V_K$ A27 gene, wherein the antibody specifically binds CD19. The invention even further provides an isolated monoclonal antibody, or an antigen-binding portion or fragment thereof; comprising a light chain variable region that is the product of or derived from a human $V_K$ L15 gene, wherein the antibody specifically binds CD19.

In a preferred embodiment, the invention provides an isolated monoclonal antibody, or an antigen-binding portion or fragment thereof, comprising (a) a heavy chain variable region of a human $V_H$ 5-51 or 1-69 gene; and (b) a light chain variable region of a human $V_K$ L18, A27 or $V_K$ L15; wherein the antibody specifically binds to CD19.

In another aspect, the invention provides an isolated monoclonal antibody, or antigen binding portion thereof, comprising a heavy chain variable region that comprises CDR1, CDR2, and CDR3 sequences; and a light chain variable region that comprises CDR1, CDR2, and CDR3 sequences, wherein: (a) the heavy chain variable region CDR3 sequence comprises an amino acid sequence selected from the group consisting of amino acid sequences of SEQ ID NOs: 30, 31, 32, 33, 34, 35 and 36, and conservative modifications thereof; (b) the light chain variable region CDR3 sequence comprises an amino acid sequence selected from the group consisting of amino acid sequence of SEQ ID NOs: 51, 52, 53, 54, 55, 56, 57 and 58, and conservative modifications thereof; (c) the antibody binds to human CD19 with a $K_D$ of $1 \times 10^{-7}$ M or less; and (d) binds to Raji and Daudi B-cell tumor cells.

Preferably, the heavy chain variable region CDR2 sequence comprises an amino acid sequence selected from the group consisting of amino acid sequences of SEQ ID NOs: 23, 24, 25, 26, 27, 28 and 29, and conservative modifications thereof; and the light chain variable region CDR2 sequence comprises an amino acid sequence selected from the group consisting of amino acid sequences of SEQ ID NOs: 44, 45, 46, 47, 48, 49 and 50, and conservative modifications thereof. Preferably, the heavy chain variable region CDR1 sequence comprises an amino acid sequence selected from the group consisting of amino acid sequences of SEQ ID NOs: 16, 17, 18, 19, 20, 21 and 22, and conservative modifications thereof; and the light chain variable region CDR1 sequence comprises an amino acid sequence selected from the group consisting of amino acid sequences of SEQ ID NOs: 37, 38, 39, 40, 41, 42 and 43, and conservative modifications thereof.

A preferred combination comprises:
(a) a heavy chain variable region CDR1 comprising SEQ ID NO: 16;
(b) a heavy chain variable region CDR2 comprising SEQ ID NO: 23;
(c) a heavy chain variable region CDR3 comprising SEQ ID NO: 30;
(d) a light chain variable region CDR1 comprising SEQ ID NO: 37;
(e) a light chain variable region CDR2 comprising SEQ ID NO: 44; and
(f) a light chain variable region CDR3 comprising SEQ ID NO: 51.

Another preferred combination comprises:
(a) a heavy chain variable region CDR1 comprising SEQ ID NO: 16;
(b) a heavy chain variable region CDR2 comprising SEQ ID NO: 23;
(c) a heavy chain variable region CDR3 comprising SEQ ID NO: 30;
(d) a light chain variable region CDR1 comprising SEQ ID NO: 37;
(e) a light chain variable region CDR2 comprising SEQ ID NO: 44; and
(f) a light chain variable region CDR3 comprising SEQ ID NO: 52.

Another preferred combination comprises:
(a) a heavy chain variable region CDR1 comprising SEQ ID NO: 17;
(b) a heavy chain variable region CDR2 comprising SEQ ID NO: 24;
(c) a heavy chain variable region CDR3 comprising SEQ ID NO: 31;
(d) a light chain variable region CDR1 comprising SEQ ID NO: 38;
(e) a light chain variable region CDR2 comprising SEQ ID NO: 45; and
(f) a light chain variable region CDR3 comprising SEQ ID NO: 53.

Another preferred combination comprises:
(a) a heavy chain variable region CDR1 comprising SEQ ID NO: 18;
(b) a heavy chain variable region CDR2 comprising SEQ ID NO: 25;
(c) a heavy chain variable region CDR3 comprising SEQ ID NO: 32;
(d) a light chain variable region CDR1 comprising SEQ ID NO: 39;
(e) a light chain variable region CDR2 comprising SEQ ID NO: 46; and
(f) a light chain variable region CDR3 comprising SEQ ID NO: 54.

Another preferred combination comprises:
(a) a heavy chain variable region CDR1 comprising SEQ ID NO: 19;
(b) a heavy chain variable region CDR2 comprising SEQ ID NO: 26;
(c) a heavy chain variable region CDR3 comprising SEQ ID NO: 33;
(d) a light chain variable region CDR1 comprising SEQ ID NO: 40;
(e) a light chain variable region CDR2 comprising SEQ ID NO: 47; and
(f) a light chain variable region CDR3 comprising SEQ ID NO: 55.

Another preferred combination comprises:
(a) a heavy chain variable region CDR1 comprising SEQ ID NO: 20;
(b) a heavy chain variable region CDR2 comprising SEQ ID NO: 27;
(c) a heavy chain variable region CDR3 comprising SEQ ID NO: 34;
(d) a light chain variable region CDR1 comprising SEQ ID NO: 41;

(e) a light chain variable region CDR2 comprising SEQ ID NO: 48; and
(f) a light chain variable region CDR3 comprising SEQ ID NO: 56.
Another preferred combination comprises:
(a) a heavy chain variable region CDR1 comprising SEQ ID NO: 21;
(b) a heavy chain variable region CDR2 comprising SEQ ID NO: 28;
(c) a heavy chain variable region CDR3 comprising SEQ ID NO: 35;
(d) a light chain variable region CDR1 comprising SEQ ID NO: 42;
(e) a light chain variable region CDR2 comprising SEQ ID NO: 49; and
(f) a light chain variable region CDR3 comprising SEQ ID NO: 57.
Another preferred combination comprises:
(a) a heavy chain variable region CDR1 comprising SEQ ID NO: 22;
(b) a heavy chain variable region CDR2 comprising SEQ ID NO: 29;
(c) a heavy chain variable region CDR3 comprising SEQ ID NO: 36;
(d) a light chain variable region CDR1 comprising SEQ ID NO: 43;
(e) a light chain variable region CDR2 comprising SEQ ID NO: 50; and
(f) a light chain variable region CDR3 comprising SEQ ID NO: 58.
Other preferred antibodies of the invention, or antigen binding portions thereof comprise:
(a) a heavy chain variable region comprising an amino acid sequence selected from the group consisting of SEQ ID NOs: 1, 2, 3, 4, 5, 6 and 7; and
(b) a light chain variable region comprising an amino acid sequence selected from the group consisting of SEQ ID NOs: 8, 9, 10, 11, 12, 13, 14 and 15;
wherein the antibody specifically binds CD19.

A preferred combination comprises: (a) a heavy chain variable region comprising the amino acid sequence of SEQ ID NO: 1; and (b) a light chain variable region comprising the amino acid sequence of SEQ ID NO: 8.

Another preferred combination comprises: (a) a heavy chain variable region comprising the amino acid sequence of SEQ ID NO: 1; and (b) a light chain variable region comprising the amino acid sequence of SEQ ID NO: 9.

Another preferred combination comprises: (a) a heavy chain variable region comprising the amino acid sequence of SEQ ID NO: 2; and (b) a light chain variable region comprising the amino acid sequence of SEQ ID NO: 10.

Another preferred combination comprises: (a) a heavy chain variable region comprising the amino acid sequence of SEQ ID NO: 3; and (b) a light chain variable region comprising the amino acid sequence of SEQ ID NO: 11.

Another preferred combination comprises: (a) a heavy chain variable region comprising the amino acid sequence of SEQ ID NO: 4; and (b) a light chain variable region comprising the amino acid sequence of SEQ ID NO: 12.

Another preferred combination comprises: (a) a heavy chain variable region comprising the amino acid sequence of SEQ ID NO: 5; and (b) a light chain variable region comprising the amino acid sequence of SEQ ID NO: 13.

Another preferred combination comprises: (a) a heavy chain variable region comprising the amino acid sequence of SEQ ID NO: 6; and (b) a light chain variable region comprising the amino acid sequence of SEQ ID NO: 14.

Another preferred combination comprises: (a) a heavy chain variable region comprising the amino acid sequence of SEQ ID NO: 7; and (b) a light chain variable region comprising the amino acid sequence of SEQ ID NO: 15.

In another aspect of the invention, antibodies, or antigen-binding portion or fragments thereof, are provided that compete for binding to CD19 with any of the aforementioned antibodies.

The antibodies of the invention can be, for example, full-length antibodies, for example of an IgG1 or IgG4 isotype. Alternatively, the antibodies can be antibody fragments, such as Fab, Fab' or Fab'2 fragments, or single chain antibodies.

The invention also provides an immunoconjugate comprising an antibody of the invention, or antigen-binding portion or fragment thereof, linked to a therapeutic agent such as a cytotoxin or a radioactive isotope. The invention also provides a bispecific molecule comprising an antibody, or antigen-binding portion or fragment thereof, of the invention, linked to a second functional moiety having a different binding specificity than said antibody, or antigen binding portion thereof.

Compositions comprising an antibody, or antigen-binding portion or fragment thereof, or immunoconjugate or bispecific molecule of the invention and a pharmaceutically acceptable carrier are also provided.

Nucleic acid molecules encoding the antibodies, or antigen-binding portions or fragments thereof, of the invention are also encompassed by the invention, as well as expression vectors comprising such nucleic acids and host cells comprising such expression vectors.

Other features and advantages of the instant invention will be apparent from the following detailed description and examples which should not be construed as limiting. The contents of all references, Genbank entries, patents and published patent applications cited throughout this application are expressly incorporated herein by reference.

BRIEF DESCRIPTION OF THE DRAWINGS

FIG. 1A shows the nucleotide sequence (SEQ ID NO: 59) and amino acid sequence (SEQ ID NO: 1) of the heavy chain variable region of the 21D4 and 21D4a human monoclonal antibodies. The CDR1 (SEQ ID NO: 16), CDR2 (SEQ ID NO: 23) and CDR3 (SEQ ID NO: 30) regions are delineated and the V, D and J germline derivations are indicated.

FIG. 1B shows the nucleotide sequence (SEQ ID NO: 66) and amino acid sequence (SEQ ID NO: 8) of the light chain variable region of the 21D4 human monoclonal antibody. The CDR1 (SEQ ID NO: 37), CDR2 (SEQ ID NO: 44) and CDR3 (SEQ ID NO: 51) regions are delineated and the V and J germline derivations are indicated.

FIG. 1C shows the nucleotide sequence (SEQ ID NO: 67) and amino acid sequence (SEQ ID NO: 9) of the light chain variable region of the 21D4a human monoclonal antibody. The CDR1 (SEQ ID NO: 37), CDR2 (SEQ ID NO: 44) and CDR3 (SEQ ID NO: 52) regions are delineated and the V and 3 germline derivations are indicated.

FIG. 2A shows the nucleotide sequence (SEQ ID NO: 60) and amino acid sequence (SEQ ID NO: 2) of the heavy chain variable region of the 47G4 human monoclonal antibody. The CDR1 (SEQ ID NO: 17), CDR2 (SEQ ID NO: 24) and CDR3 (SEQ ID NO: 31) regions are delineated and the V, D and J germline derivations are indicated.

FIG. 2B shows the nucleotide sequence (SEQ ID NO: 68) and amino acid sequence (SEQ ID NO: 10) of the light chain variable region of the 47G4 human monoclonal antibody. The CDR1 (SEQ ID NO: 38), CDR2 (SEQ ID NO: 45) and CDR3

Figure 23:
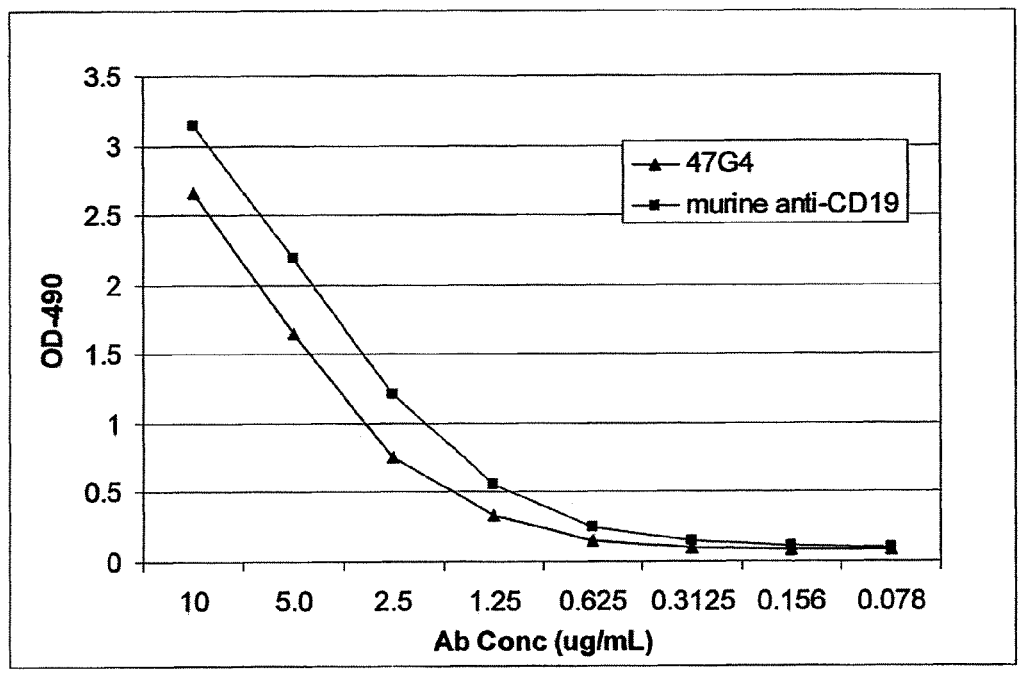
Figure 25A:
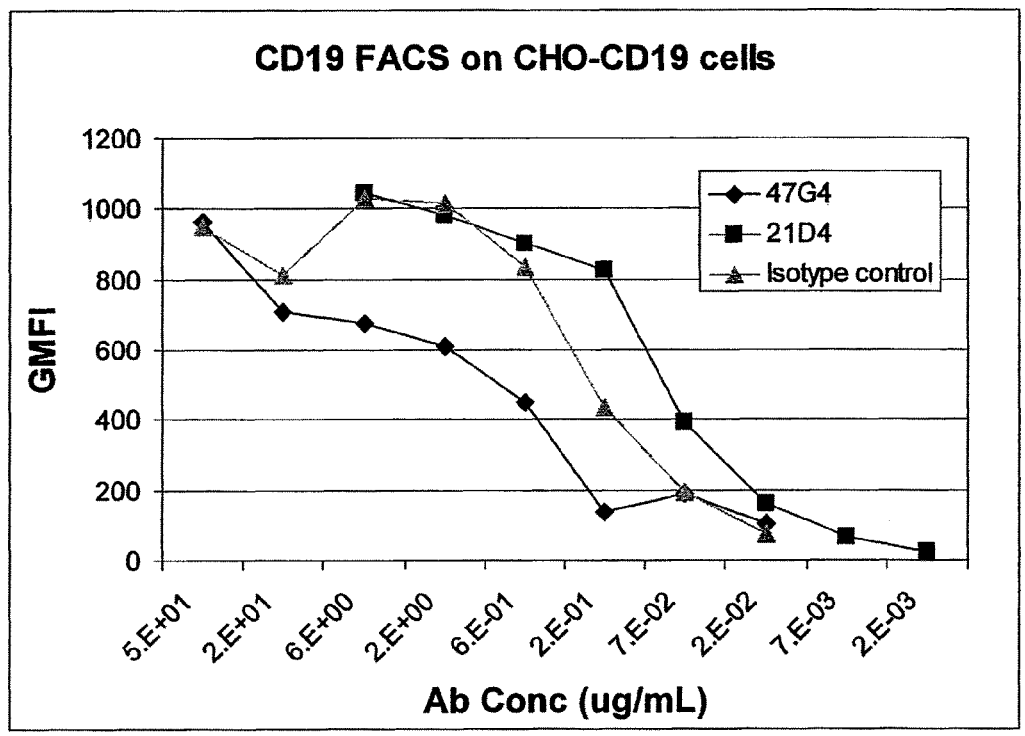
Figure 25B:
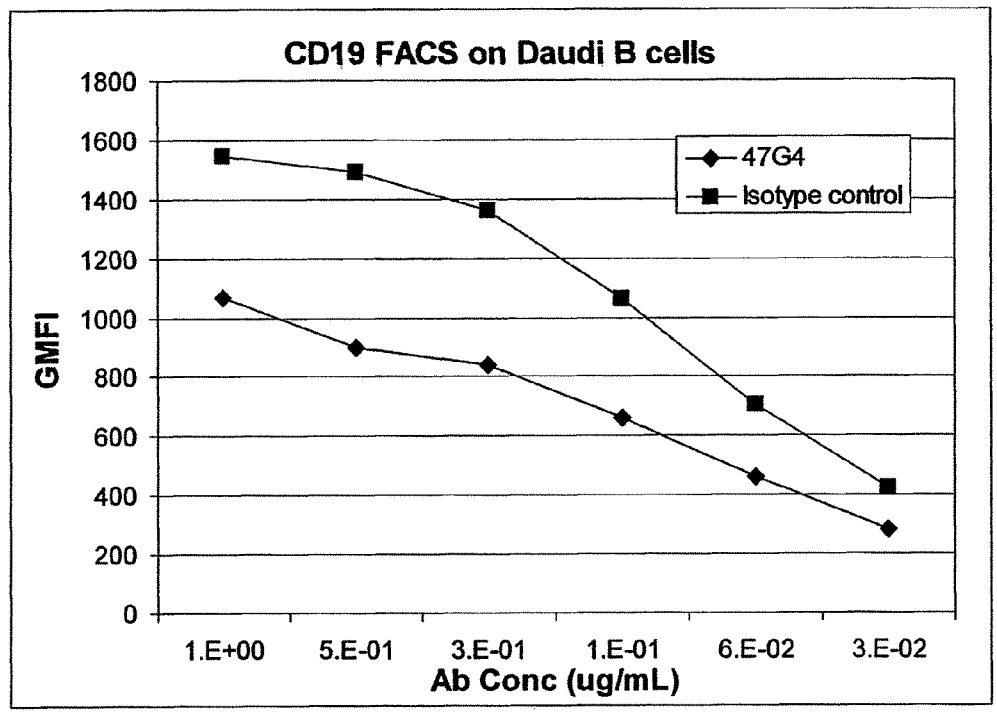
Figure 25C:
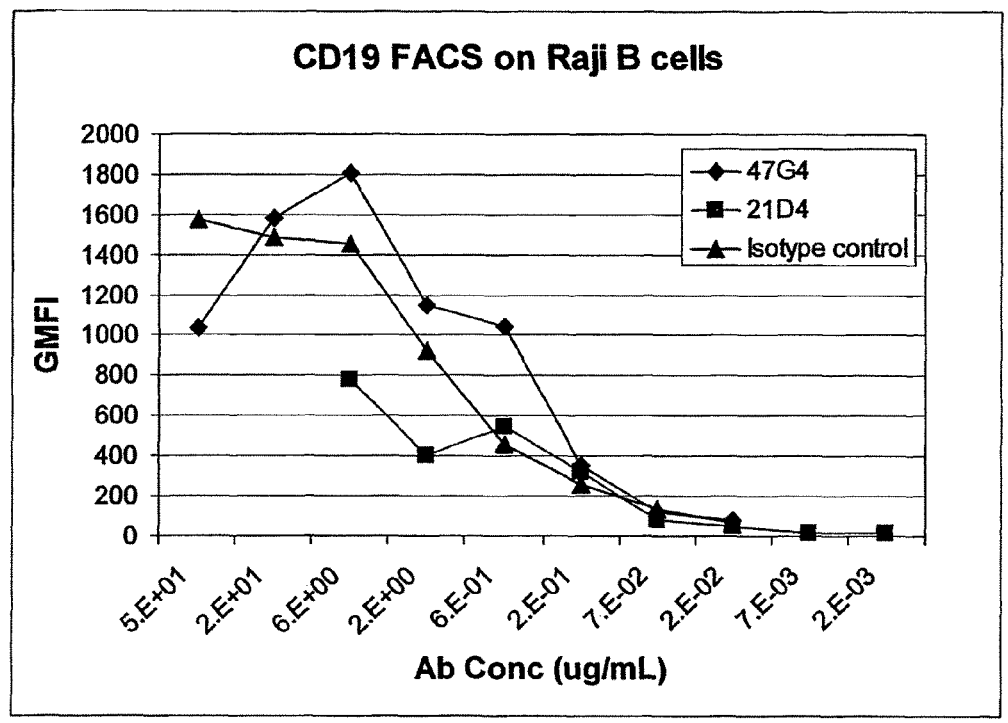
Figure 25D:
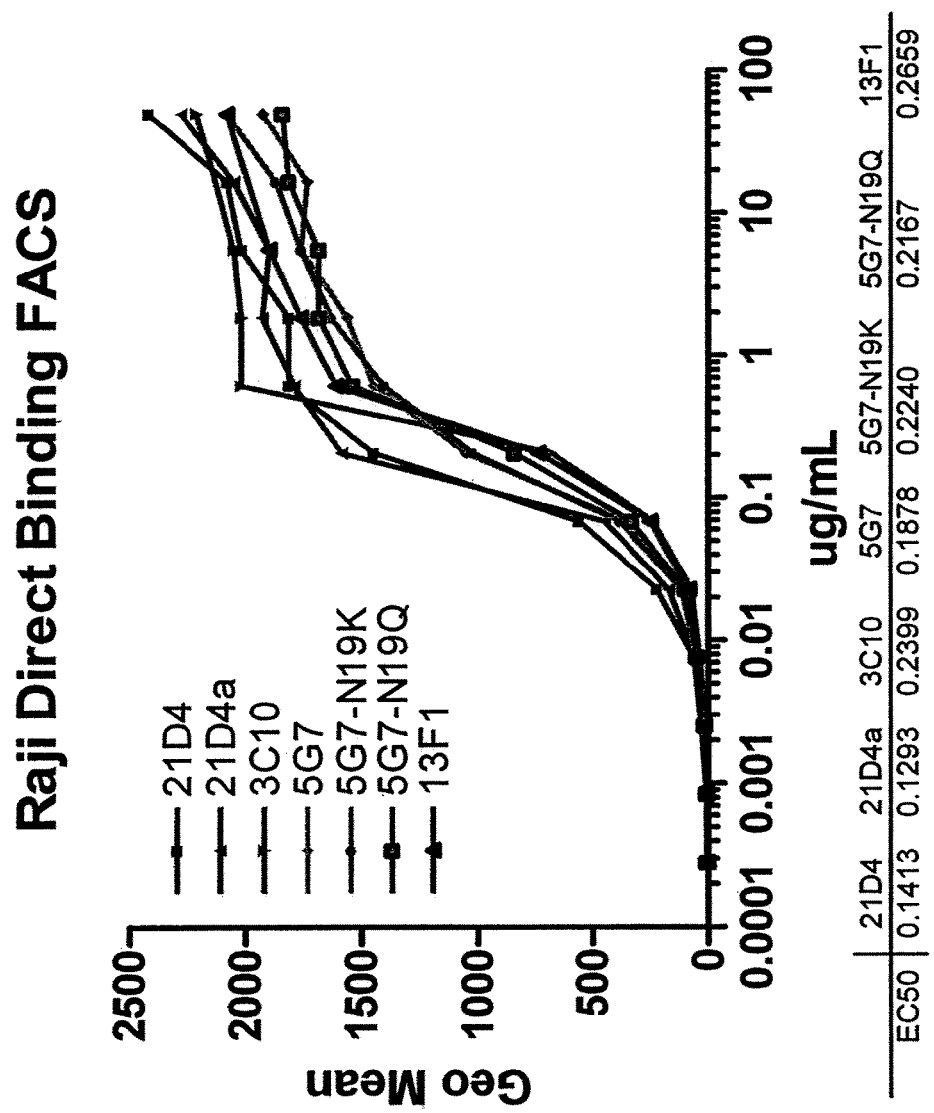

(SEQ ID NO: 53) regions are delineated and the V and J germline derivations are indicated.

FIG. 3A shows the nucleotide sequence (SEQ ID NO: 61) and amino acid sequence (SEQ ID NO: 3) of the heavy chain variable region of the 27F3 human monoclonal antibody. The CDR1 (SEQ ID NO: 18), CDR2 (SEQ ID NO: 25) and CDR3 (SEQ ID NO: 32) regions are delineated and the V, D and J germline derivations are indicated.

FIG. 3B shows the nucleotide sequence (SEQ ID NO: 69) and amino acid sequence (SEQ ID NO: 11) of the light chain variable region of the 27F3 human monoclonal antibody. The CDR1 (SEQ ID NO: 39), CDR2 (SEQ ID NO: 46) and CDR3 (SEQ ID NO: 54) regions are delineated and the V and J germline derivations are indicated.

FIG. 4A shows the nucleotide sequence (SEQ ID NO: 62) and amino acid sequence (SEQ ID NO: 4) of the heavy chain variable region of the 3C10 human monoclonal antibody. The CDR1 (SEQ ID NO: 19), CDR2 (SEQ ID NO: 26) and CDR3 (SEQ ID NO: 33) regions are delineated and the V, D and J germline derivations are indicated.

FIG. 4B shows the nucleotide sequence (SEQ ID NO: 70) and amino acid sequence (SEQ ID NO: 12) of the light chain variable region of the 3C10 human monoclonal antibody. The CDR1 (SEQ ID NO: 40), CDR2 (SEQ ID NO: 47) and CDR3 (SEQ ID NO: 55) regions are delineated and the V and J germline derivations are indicated.

FIG. 5A shows the nucleotide sequence (SEQ ID NO: 63) and amino acid sequence (SEQ ID NO: 5) of the heavy chain variable region of the 5G7 human monoclonal antibody. The CDR1 (SEQ ID NO: 20), CDR2 (SEQ ID NO: 27) and CDR3 (SEQ ID NO: 34) regions are delineated and the V, D and J germline derivations are indicated.

FIG. 5B shows the nucleotide sequence (SEQ ID NO: 71) and amino acid sequence (SEQ ID NO: 13) of the light chain variable region of the 5G7 human monoclonal antibody. The CDR1 (SEQ ID NO: 41), CDR2 (SEQ ID NO: 48) and CDR3 (SEQ ID NO: 56) regions are delineated and the V and J germline derivations are indicated.

FIG. 6A shows the nucleotide sequence (SEQ ID NO: 64) and amino acid sequence (SEQ ID NO: 6) of the heavy chain variable region of the 13F1 human monoclonal antibody. The CDR1 (SEQ ID NO: 21), CDR2 (SEQ ID NO: 28) and CDR3 (SEQ ID NO: 35) regions are delineated and the V, D and J germline derivations are indicated.

FIG. 6B shows the nucleotide sequence (SEQ ID NO: 72) and amino acid sequence (SEQ ID NO: 14) of the light chain variable region of the 13F1 human monoclonal antibody. The CDR1 (SEQ ID NO: 42), CDR2 (SEQ ID NO: 49) and CDR3 (SEQ ID NO: 57) regions are delineated and the V and J germline derivations are indicated.

FIG. 7A shows the nucleotide sequence (SEQ ID NO: 65) and amino acid sequence (SEQ ID NO: 7) of the heavy chain variable region of the 46E8 human monoclonal antibody. The CDR1 (SEQ ID NO: 22), CDR2 (SEQ ID NO: 29) and CDR3 (SEQ ID NO: 36) regions are delineated and the V, D and J germline derivations are indicated.

FIG. 7B shows the nucleotide sequence (SEQ ID NO: 73) and amino acid sequence (SEQ ID NO: 15) of the light chain variable region of the 46E8 human monoclonal antibody. The CDR1 (SEQ ID NO: 43), CDR2 (SEQ ID NO: 50) and CDR3 (SEQ ID NO: 58) regions are delineated and the V and J germline derivations are indicated.

FIG. 8 shows the alignment of the amino acid sequence of the heavy chain variable region of 21D4 (SEQ ID NO: 1) and 21D4a (SEQ ID NO: 1), with the human germline $V_H$ 5-51 amino acid sequence (SEQ ID NO: 74). The JH4b germline is disclosed as SEQ ID NO: 80.

FIG. 9 shows the alignment of the amino acid sequence of the heavy chain variable region of 47G4 (SEQ ID NO: 2) with the human germline $V_H$ 1-69 amino acid sequences (SEQ ID NO: 75). The JH5b germline is disclosed as SEQ ID NO: 81.

FIG. 10 shows the alignment of the amino acid sequence of the heavy chain variable region of 27F3 (SEQ ID NO: 3), with the human germline $V_H$ 5-51 amino acid sequence (SEQ ID NO: 74). The JH6b germline is disclosed as SEQ ID NO: 82.

FIG. 11 shows the alignment of the amino acid sequence of the heavy chain variable region of 3C10 (SEQ ID NO: 4) with the human germline $V_H$ 1-69 amino acid sequences (SEQ ID NO: 75). The JH6b germline is disclosed as SEQ ID NO: 82.

FIG. 12 shows the alignment of the amino acid sequence of the heavy chain variable region of 5G7 (SEQ ID NO: 5), with the human germline $V_H$ 5-51 amino acid sequence (SEQ ID NO: 74). The JH6b germline is disclosed as SEQ ID NO: 83.

FIG. 13 shows the alignment of the amino acid sequence of the heavy chain variable region of 13F1 (SEQ ID NO: 6), with the human germline $V_H$ 5-51 amino acid sequence (SEQ ID NO: 74). The JH6b germline is disclosed as SEQ ID NO: 82.

FIG. 14 shows the alignment of the amino acid sequence of the heavy chain variable region of 46E8 (SEQ ID NO: 7), with the human germline $V_H$ 5-51 amino acid sequence (SEQ ID NO: 74). The JH6b germline is disclosed as SEQ ID NO: 82.

FIG. 15 shows the alignment of the amino acid sequence of the light chain variable region of 21D4 (SEQ ID NO: 8) with the human germline $V_k$ L18 amino acid sequence (SEQ ID NO:76). The JK2 germline is disclosed as SEQ ID NO: 84.

FIG. 16 shows the alignment of the amino acid sequence of the light chain variable region of 21D4a (SEQ ID NO: 9) with the human germline $V_k$ L18 amino acid sequence (SEQ ID NO:76). The JK3 germline is disclosed as SEQ ID NO: 85.

FIG. 17 shows the alignment of the amino acid sequence of the light chain variable region of 47G4 (SEQ ID NO: 10) with the human germline $V_k$ A27 amino acid sequence (SEQ ID NO:77). The JK3 germline is disclosed as SEQ ID NO: 85.

FIG. 18 shows the alignment of the amino acid sequence of the light chain variable region of 27F3 (SEQ ID NO: 11) with the human germline $V_k$ L18 amino acid sequence (SEQ ID NO:76). The JK2 germline is disclosed as SEQ ID NO: 84.

FIG. 19 shows the alignment of the amino acid sequence of the light chain variable region of 3C10 (SEQ ID NO: 12) with the human germline $V_k$ L15 amino acid sequence (SEQ ID NO:78). The JK2 germline is disclosed as SEQ ID NO: 84.

FIG. 20 shows the alignment of the amino acid sequence of the light chain variable region of 5G7 (SEQ ID NO: 13) with the human germline $V_k$ L18 amino acid sequence (SEQ ID NO:76). The JK1 germline is disclosed as SEQ ID NO: 86.

FIG. 21 shows the alignment of the amino acid sequence of the light chain variable region of 13F1 (SEQ ID NO: 14) with the human germline $V_k$ L18 amino acid sequence (SEQ ID NO:76). The JK2 germline is disclosed as SEQ ID NO: 87.

FIG. 22 shows the alignment of the amino acid sequence of the light chain variable region of 46E8 (SEQ ID NO: 15) with the human germline $V_k$ L18 amino acid sequence (SEQ ID NO:76). The JK2 germline is disclosed as SEQ ID NO: 87.

FIG. 23 is a graph showing the results of experiments demonstrating that the human monoclonal antibody 47G4, directed against human CD19, specifically binds to human CD19.

FIG. 24 is a graph showing the results of experiments demonstrating that the human monoclonal antibodies against CD19 compete for binding on Raji cells.

FIG. 25A-D shows the results of flow cytometry experiments demonstrating that the human monoclonal antibodies 21D4, 21D4a, 47G4, 3C10, 5G7 and 13F1, directed against human CD19, binds the cell surface of B-cell tumor cell lines.

(A) Flow cytometry of HuMAbs 21D4 and 47G4 on CHO cells transfected with human CD19. (B) Flow cytometry of HuMAb 47G4 on Daudi B tumor cells. (C) Flow cytometry of HuMAbs 21D4 and 47G4 on Raji B tumor cells. (D) Flow cytometry of HuMAbs 21D4, 21D4a, 3C10, 5G7 and 13F1 on Raji B tumor cells.

Figure 26A:
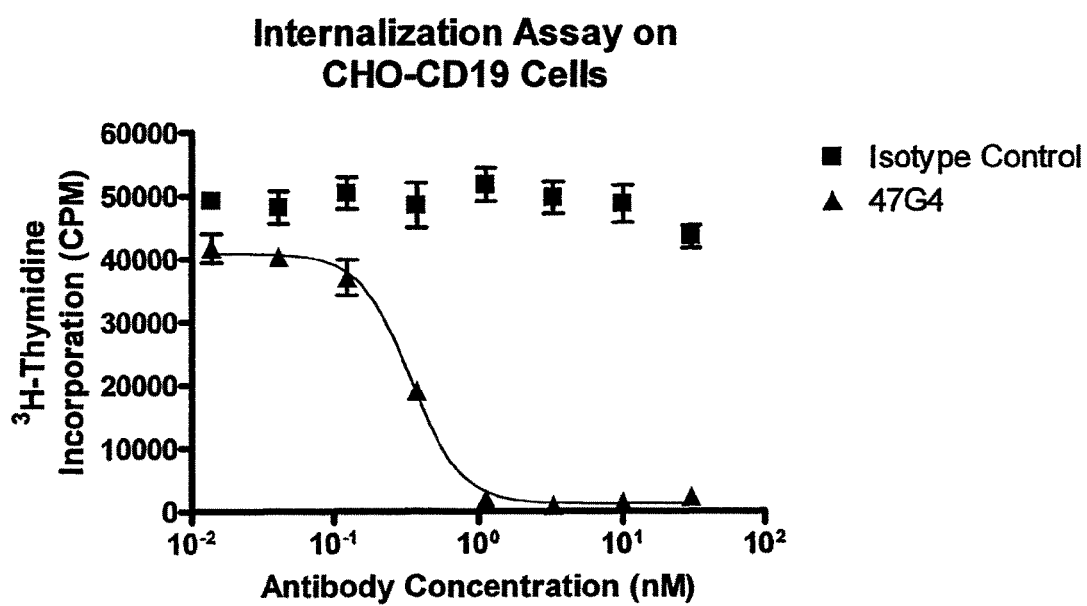
Figure 26B:
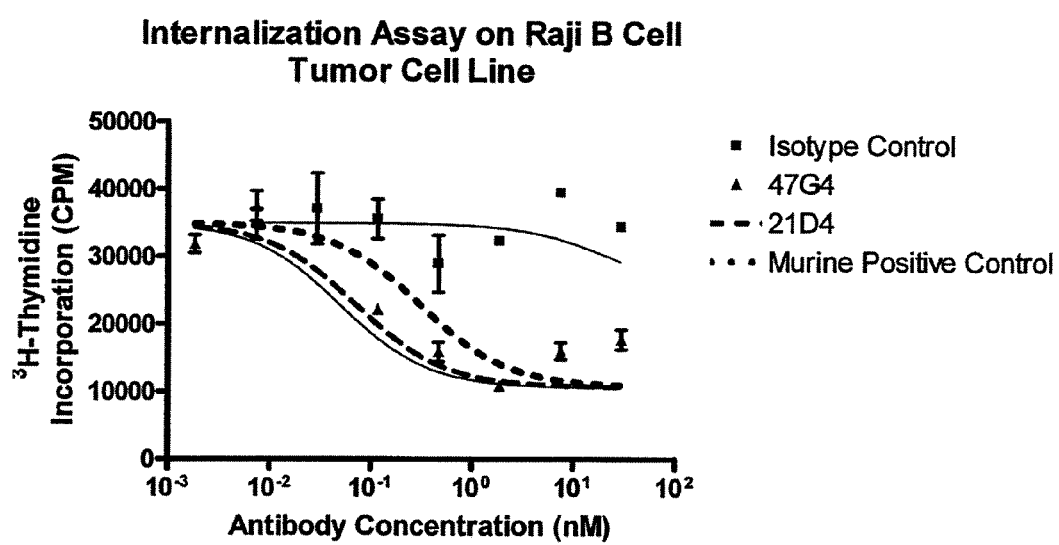

FIGS. 26A-B shows the results of internalization experiments demonstrating that the human monoclonal antibodies 21D4 and 47G4, directed against human CD19, enters CHO-CD19 and CD19-expressing Raji B tumor cells by a 3H-thymidine release assay.

(A) HuMAb 47G4 internalization into CHO-CD19 cells. (B) HuMAbs 21D4 and 47G4 internalization into Raji B tumor cells.

Figure 27:
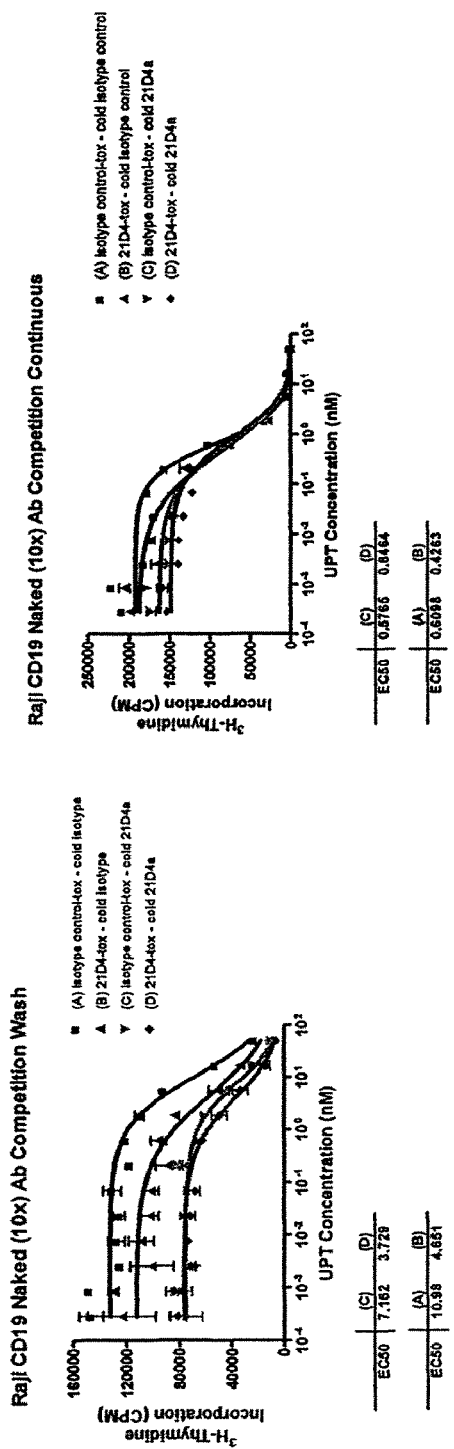

FIG. 27 shows the results of a thymidine incorporation assay demonstrating that human monoclonal antibodies directed against human CD19 kill Raji B cell tumor cells.

Figure 28:
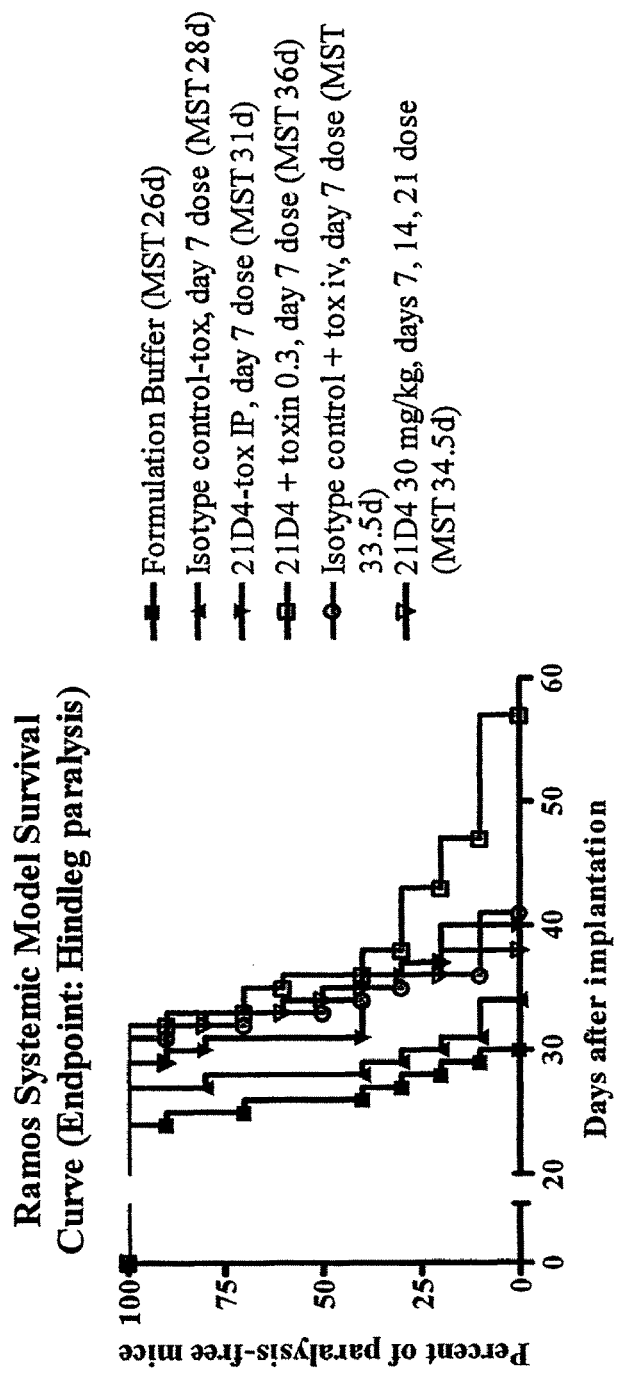

FIG. 28 shows a Kaplan-Meier plot of mouse survival in a Ramos systemic model.

Figure 29:
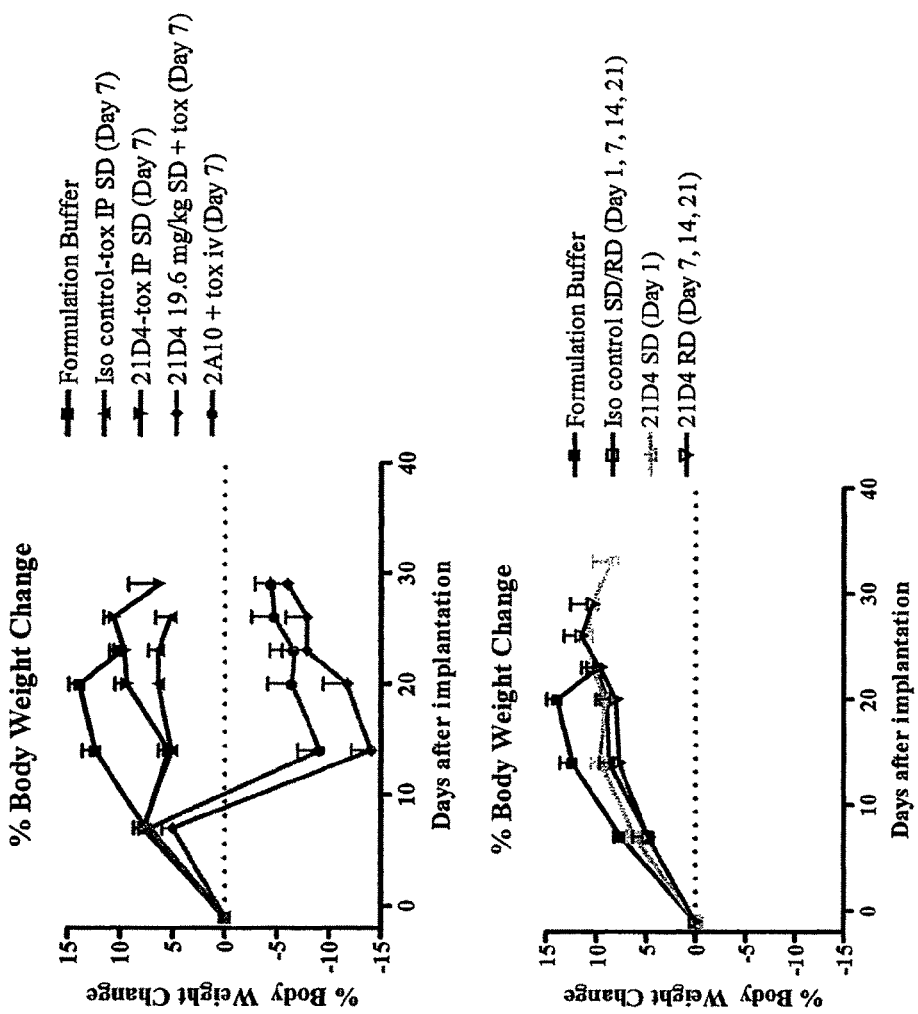

FIG. 29 shows the body weight change in mice in a Ramos systemic model.

FIG. 30A-B shows the results of an in vivo mouse tumor model study demonstrating that treatment with naked anti-CD19 antibody 21D4 has a direct inhibitory effect on lymphoma tumors in vivo. (A) ARH-77 tumors (B) Raji tumors.

Figure 31:
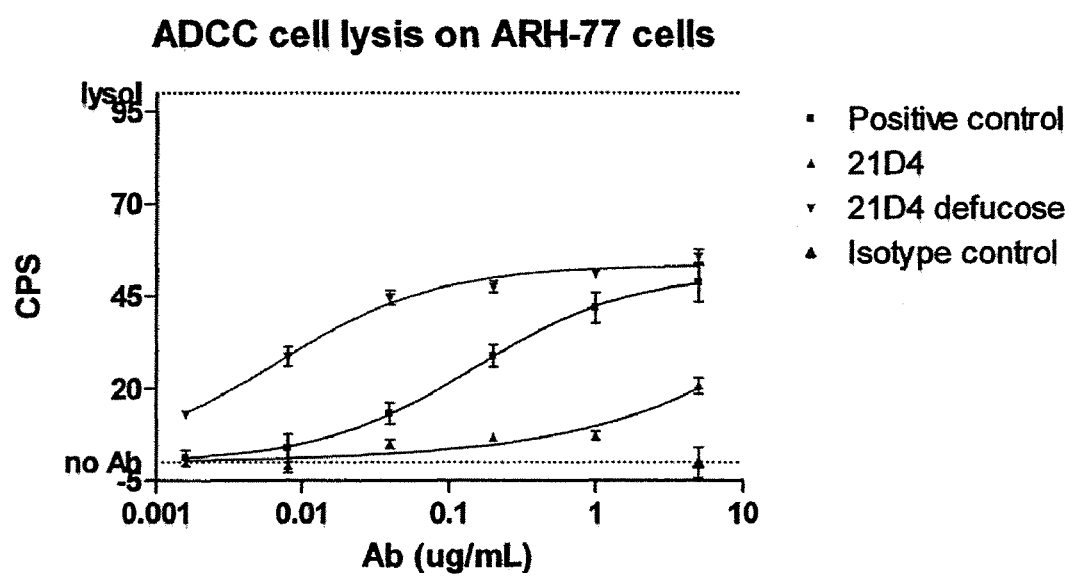

FIG. 31 shows the results of an antibody dependent cellular cytotoxicity (ADCC) assay demonstrating that nonfucosylated human monoclonal anti-CD19 antibodies have increased cell cytotoxicity on human leukemia cells in an ADCC dependent manner.

Figure 32:
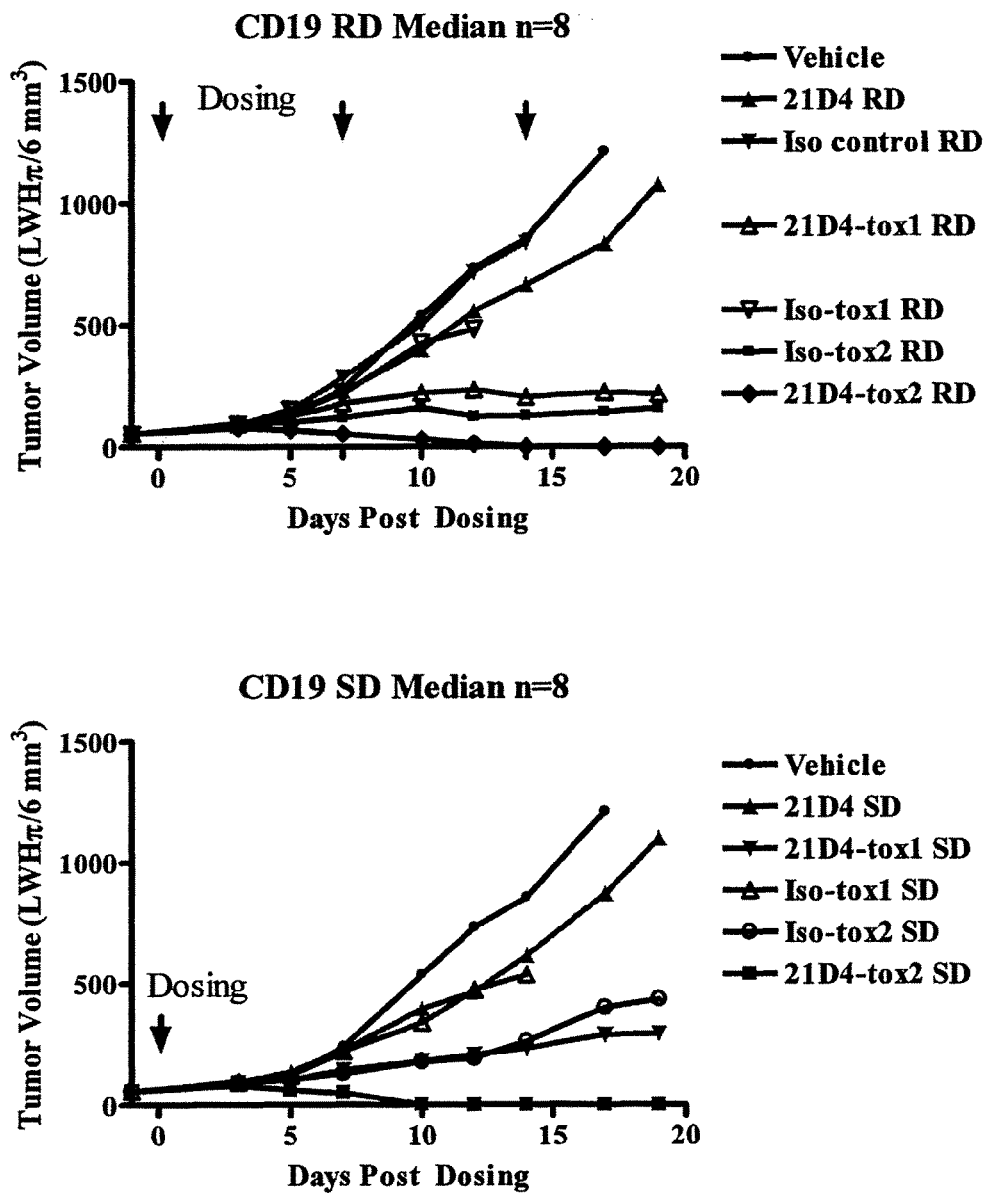

FIG. 32 shows the results of an in vivo mouse tumor model study demonstrating that toxin-conjugated anti-CD19 antibodies reduce tumor volume.

FIG. 33 shows the body weight change in mice in a Raji tumor model study.

Figure 34:
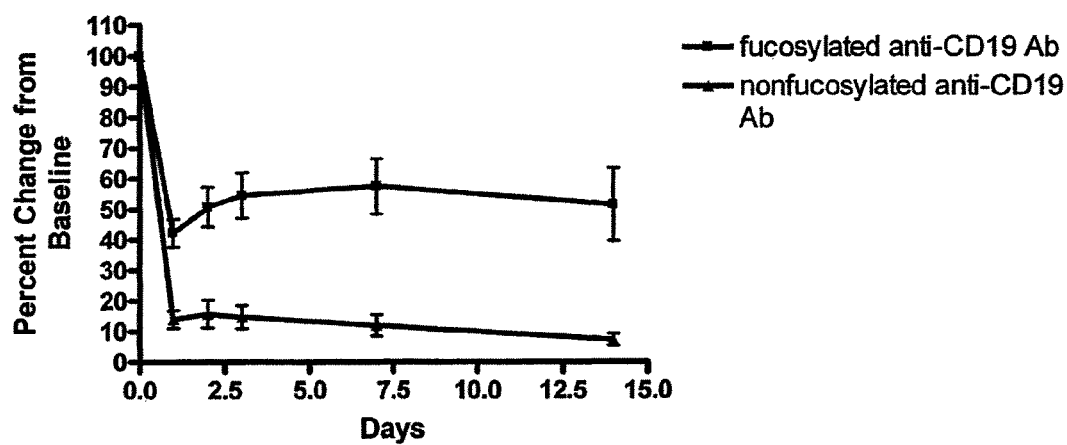

FIG. 34 shows the results of a cynomolgus monkey study showing a decreased population of CD20+ cells following treatment of fucosylated or nonfucosylated anti-CD19 HuMAbs.

Figure 35:
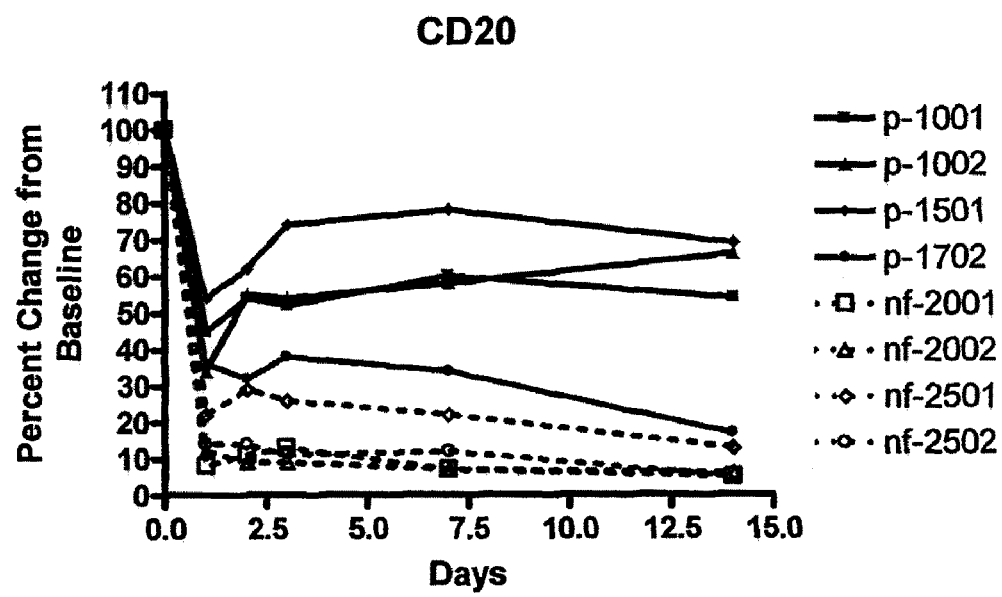

FIG. 35 shows the results of individual cynomolgus monkeys following treatment with fucosylated or nonfucosylated anti-CD19 HuMAbs.

Figure 36A:
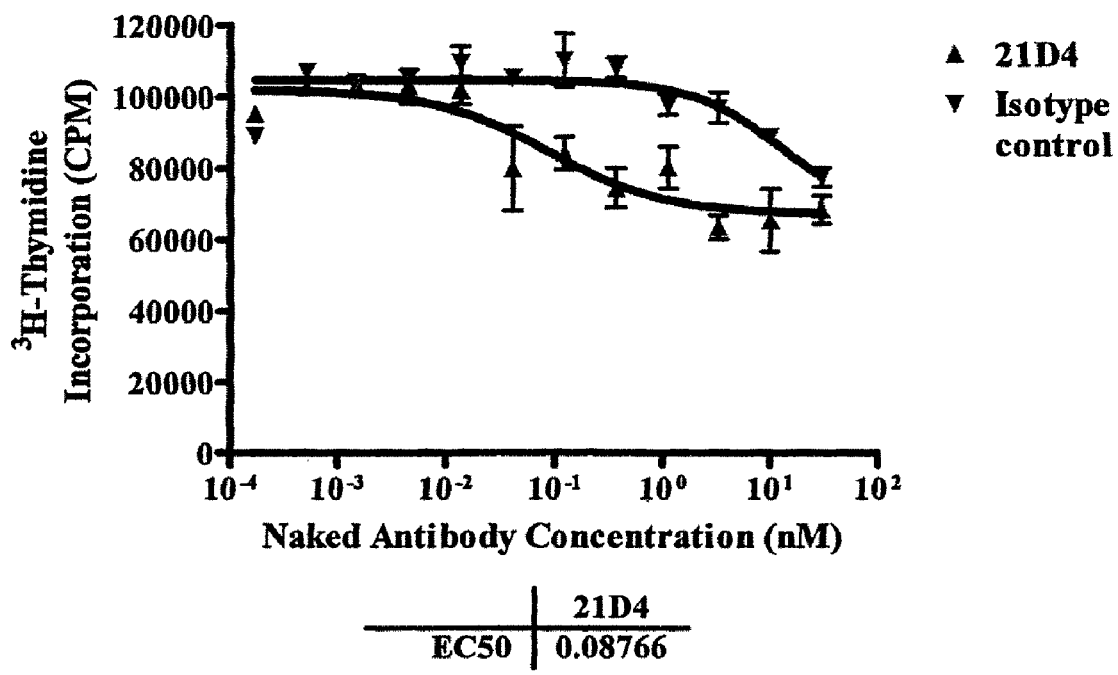
Figure 36B:
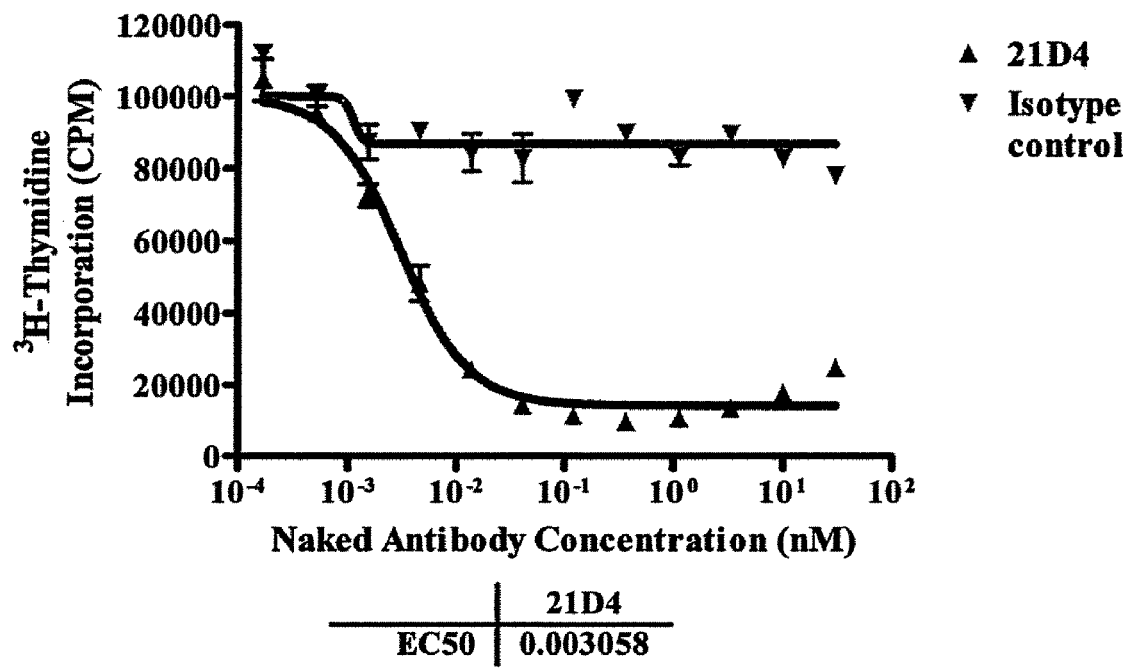
Figure 36C:
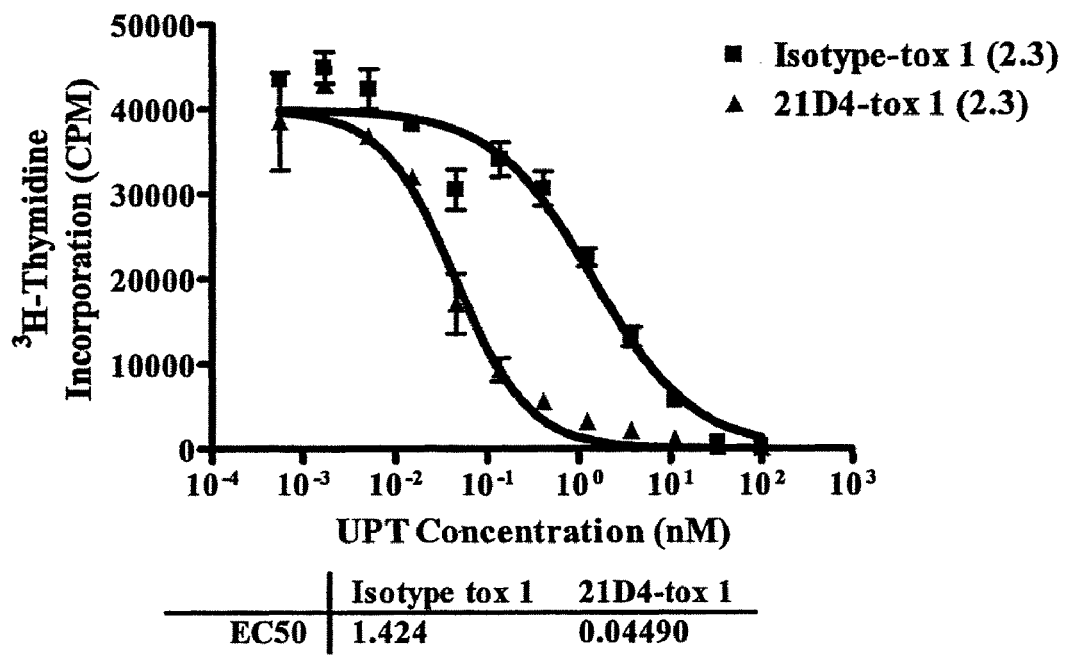

FIG. 36A-C shows the results of a thymidine incorporation assay demonstrating that human monoclonal antibodies directed against human CD19 alone or toxin-conjugated kill Raji and SU-DHL-6 B cell tumor cells.

DETAILED DESCRIPTION

The present disclosure relates to isolated monoclonal antibodies, particularly human monoclonal antibodies that bind specifically to CD19 with high affinity. In certain embodiments, the antibodies of the invention are derived from particular heavy and light chain germline sequences and/or comprise particular structural features such as CDR regions comprising particular amino acid sequences. The invention provides isolated antibodies, methods of making such antibodies, immunoconjugates and bispecific molecules comprising such antibodies and pharmaceutical compositions containing the antibodies, immunconjugates or bispecific molecules of the invention. The invention also relates to methods of using the antibodies, such as to detect CD19, as well as to treat diseases associated with expression of CD19, such as B cell malignancies that express CD19. Accordingly, the invention also provides methods of using the anti-CD19 antibodies of the invention to treat B cell malignancies, for example, in the treatment of non-Hodgkin's lymphoma, chronic lymphocytic leukemias, follicular lymphomas, diffuse large cell lymphomas of B lineage, and multiple myelomas.

In order that the present invention may be more readily understood, certain terms are first defined. Additional definitions are set forth throughout the detailed description.

The term "CD19" refers to, for example, variants, isoforms, and species homologs of human CD19. Accordingly, human antibodies of this disclosure may, in certain cases, cross-react with CD19 from species other than human. In certain embodiments, the antibodies may be completely specific for one or more human CD19 proteins and may not exhibit species or other types of non-human cross-reactivity. The complete amino acid sequence of an exemplary human CD19 has Genbank accession number NM_001770 (SEQ ID NO: 79).

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between various signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present invention is the CD19 receptor.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., CD19). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H1$ domains; (ii) a F(ab)$_2$ fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY, Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody, (vi) a dAb fragment (Ward et al., (1989) Nature 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds CD19 is substantially free of antibodies that specifically bind antigens other than CD19). An isolated antibody that specifically binds CD19 may, however, have cross-reactivity to other antigens, such as CD19 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human CD19" is intended to refer to an antibody that binds to human CD19 with a $K_D$ of $1 \times 10^{-7}$ M or less, more preferably $5 \times 10$ μM or less, more preferably $3 \times 10$ μM or less, more preferably $1 \times 10^{-8}$ M or less, even more preferably $5 \times 10^{-9}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $1 \times 10^{-7}$ M or less, more preferably $5 \times 10^{-8}$ M or less and even more preferably $1 \times 10^{-9}$ M or less and even more preferably $5\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

As used herein, the term "subject" includes any human or nonhuman animal. The term "nonhuman animal" includes all vertebrates, e.g. mammals and non-mammals, such as non-human primates, sheep, dogs, cats, horses, cows, chickens, amphibians, reptiles, etc.

Anti-CD19 Antibodies

The antibodies of the invention are characterized by particular functional features or properties of the antibodies. For example, the antibodies bind specifically to human CD19. Preferably, an antibody of the invention binds to CD19 with high affinity, for example with a $K_D$ of $1\times10^{-7}$ M or less. The anti-CD19 antibodies of the invention preferably exhibit one or more of the following characteristics:

(a) binds to human CD19 with a $K_D$ of $1\times10^{-7}$ M or less;
(b) binds to Raji and Daudi B-cell tumor cells.

Preferably, the antibody binds to human CD19 with a $K_D$ of $5\times10^{-8}$ M or less, binds to human CD19 with a $K_D$ of $1\times10^{-8}$ M or less, binds to human CD19 with a $K_D$ of $5\times10^{-9}$ M or less, binds to human CD19 with a $K_D$ of $4\times10^{-9}$ M or less, binds to human CD19 with a $K_D$ of $3\times10^{-9}$ M or less, or binds to human CD19 with a $K_D$ of $2\times10^{-9}$ M or less, or binds to human CD19 with a $K_D$ of $1\times10^{-9}$ M or less.

Standard assays to evaluate the binding ability of the antibodies toward CD19 are known in the art, including for example, ELISAs, Western blots, RIAs, and flow cytometry analysis. Suitable assays are described in detail in the Examples. The binding kinetics (e.g., binding affinity) of the antibodies also can be assessed by standard assays known in the art, such as by Scatchard or Biacore® system analysis. To assess binding to Raji or Daudi B cell tumor cells, Raji (ATCC Deposit No. CCL-86) or Daudi (ATCC Deposit No. CCL-213) cells can be obtained from publicly available sources, such as the American Type Culture Collection, and used in standard assays, such as flow cytometric analysis.

Monoclonal Antibodies 21D4, 21D4a, 47G4, 27F3, 3C10, 5G7, 13F1 and 46E8

Preferred antibodies of the invention are the human monoclonal antibodies 21D4, 21D4a, 47G4, 27F3, 3C10, 5G7, 13F1 and 46E8, isolated and structurally characterized as described in Examples 16, 17, 18, 19, 20, 21 and 22. The $V_H$ amino acid sequences of 21D4, 21D4a, 47G4, 27F3, 3C10, 5G7, 13F1 and 46E8 are shown in SEQ ID NOs: 1, 1, 2, 3, 4, 5, 6 and 7, respectively. The $V_L$ amino acid sequences of 21D4, 21D4a, 47G4, 27F3, 3C10, 5G7, 13F1 and 46E8 are shown in SEQ ID NOs: 8, 9, 10, 11, 12, 13, 14 and 15, respectively.

Given that each of these antibodies can bind to CD19, the $V_H$ and $V_L$ sequences can be "mixed and matched" to create other anti-CD19 binding molecules of the invention. CD19 binding of such "mixed and matched" antibodies can be tested using the binding assays described above and in the Examples (e.g., ELISAs). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one aspect, the invention provides an isolated monoclonal antibody, or antigen binding portion thereof comprising:

(a) a heavy chain variable region comprising an amino acid sequence selected from the group consisting of SEQ ID NOs: 1, 2, 3, 4, 5, 6 and 7; and
(b) a light chain variable region comprising an amino acid sequence selected from the group consisting of SEQ ID NOs: 8, 9, 10, 11, 12, 13, 14 and 15;

wherein the antibody specifically binds CD19, preferably human CD19.

Preferred heavy and light chain combinations include:

(a) a heavy chain variable region comprising the amino acid sequence of SEQ ID NO: 1; and (b) a light chain variable region comprising the amino acid sequence of SEQ ID NO: 8; or (a) a heavy chain variable region comprising the amino acid sequence of SEQ ID NO: 1; and (b) a light chain variable region comprising the amino acid sequence of SEQ ID NO: 9; or (a) a heavy chain variable region comprising the amino acid sequence of SEQ ID NO: 2; and (b) a light chain variable region comprising the amino acid sequence of SEQ ID NO: 10; or (a) a heavy chain variable region comprising the amino acid sequence of SEQ ID NO: 3; and (b) a light chain variable region comprising the amino acid sequence of SEQ ID NO: 11; or (a) a heavy chain variable region comprising the amino acid sequence of SEQ ID NO: 4; and (b) a light chain variable region comprising the amino acid sequence of SEQ ID NO: 12; or (a) a heavy chain variable region comprising the amino acid sequence of SEQ ID NO: 5; and (b) a light chain variable region comprising the amino acid sequence of SEQ ID NO: 13; or (a) a heavy chain variable region comprising the amino acid sequence of SEQ ID NO: 6; and (b) a light chain variable region comprising the amino acid sequence of SEQ ID NO: 14; or (a) a heavy chain variable region comprising the amino acid sequence of SEQ ID NO: 7; and (b) a light chain variable region comprising the amino acid sequence of SEQ ID NO: 15.

In another aspect, the invention provides antibodies that comprise the heavy chain and light chain CDR1s, CDR2s and CDR3s of 21D4, 21D4a, 47G4, 27F3, 3C10, 5G7, 13F1 and 46E8, or combinations thereof. The amino acid sequences of the $V_H$ CDR1s of 21D4, 21D4a, 47G4, 27F3, 3C10, 5G7, 13F1 and 46E8 are shown in SEQ ID NOs: 16, 17, 18, 19, 20, 21 and 22. The amino acid sequences of the $V_H$ CDR2s of 21D4, 21D4a, 47G4, 27F3, 3C10, 5G7, 13F1 and 46E8 are shown in SEQ ID NOs: 23, 24, 25, 26, 27, 28 and 29. The amino acid sequences of the $V_H$ CDR3s of 21D4, 21D4a, 47G4, 27F3, 3C10, 5G7, 13F1 and 46E8 are shown in SEQ ID NOs: 30, 31, 32, 33, 34, 35 and 36. The amino acid sequences of the $V_k$ CDR1s of 21D4, 21D4a, 47G4, 27F3, 3C10, 5G7, 13F1 and 46E8 are shown in SEQ ID NOs: 37, 38, 39, 40, 41, 42 and 43. The amino acid sequences of the $V_k$ CDR2s of 21D4, 21D4a, 47G4, 27F3, 3C10, 5G7, 13F1 and 46E8 are shown in SEQ ID NOs: 44, 45, 46, 47, 48, 49 and 50. The amino acid sequences of the $V_k$ CDR3s of 21D4, 21D4a, 47G4, 27F3, 3C10, 5G7, 13F1 and 46E8 are shown in SEQ ID NOs: 51, 52, 53, 54, 55, 56, 57 and 58. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to CD19 and that antigen-binding specificity is provided primarily by the CDR1, CDR2, and CDR3 regions, the V$_H$ CDR1, CDR2, and CDR3 sequences and V$_k$ CDR1, CDR2, and CDR3 sequences can be "mixed and matched" (i.e., CDRs from different antibodies can be mixed and match, although each antibody must contain a V$_H$ CDR1, CDR2, and CDR3 and a V$_k$ CDR1, CDR2, and CDR3) to create other anti-CD19 binding molecules of the invention. CD19 binding of such "mixed and matched" antibodies can be tested using the binding assays described above and in the Examples (e.g., ELISAs, Biacore® analysis). Preferably, when V$_H$ CDR sequences are mixed and matched, the CDR1, CDR2 and/or CDR3 sequence from a particular V$_H$ sequence is replaced with a structurally similar CDR sequence(s). Likewise, when V$_k$ CDR sequences are mixed and matched, the CDR1, CDR2 and/or CDR3 sequence from a particular V$_k$ sequence preferably is replaced with a structurally similar CDR sequence(s). It will be readily apparent to the ordinarily skilled artisan that novel V$_H$ and V$_L$ sequences can be created by substituting one or more V$_H$ and/or V$_L$ CDR region sequences with structurally similar sequences from the CDR sequences disclosed herein for monoclonal antibodies antibodies 21D4, 21D4a, 47G4, 27F3, 3C10, 5G7, 13F1 and 46E8.

Accordingly, in another aspect, the invention provides an isolated monoclonal antibody, or antigen binding portion thereof comprising:

(a) a heavy chain variable region CDR1 comprising an amino acid sequence selected from the group consisting of SEQ ID NOs: 16, 17, 18, 19, 20, 21 and 22;

(b) a heavy chain variable region CDR2 comprising an amino acid sequence selected from the group consisting of SEQ ID NOs: 23, 24, 25, 26, 27, 28 and 29;

(c) a heavy chain variable region CDR3 comprising an amino acid sequence selected from the group consisting of SEQ ID NOs: 30, 31, 32, 33, 34, 35 and 36;

(d) a light chain variable region. CDR1 comprising an amino acid sequence selected from the group consisting of SEQ ID NOs: 37, 38, 39, 40, 41, 42 and 43;

(e) a light chain variable region CDR2 comprising an amino acid sequence selected from the group consisting of SEQ ID NOs: 44, 45, 46, 47, 48, 49 and 50; and (f) a light chain variable region CDR3 comprising an amino acid sequence selected from the group consisting of SEQ ID NOs: 51, 52, 53, 54, 55, 56, 57 and 58;

wherein the antibody specifically binds CD19, preferably human CD19.

In a preferred embodiment, the antibody comprises:
(a) a heavy chain variable region CDR1 comprising SEQ ID NO: 16;
(b) a heavy chain variable region CDR2 comprising SEQ ID NO: 23;
(c) a heavy chain variable region CDR3 comprising SEQ ID NO: 30;
(d) a light chain variable region CDR1 comprising SEQ ID NO: 37;
(e) a light chain variable region CDR2 comprising SEQ ID NO: 44; and
(f) a light chain variable region CDR3 comprising SEQ ID NO: 51.

In another preferred embodiment, the antibody comprises:
(a) a heavy chain variable region CDR1 comprising SEQ ID NO: 16;
(b) a heavy chain variable region CDR2 comprising SEQ ID NO: 23;
(c) a heavy chain variable region CD3 comprising SEQ ID NO: 30;
(d) a light chain variable region CDR1 comprising SEQ ID NO: 37;
(e) a light chain variable region CDR2 comprising SEQ ID NO: 44; and
(e) a light chain variable region CDR3 comprising SEQ ID NO: 52.

In another preferred embodiment, the antibody comprises:
(a) a heavy chain variable region CDR1 comprising SEQ ID NO: 17;
(b) a heavy chain variable region CDR2 comprising SEQ ID NO: 24;
(c) a heavy chain variable region CDR3 comprising SEQ ID NO: 31;
(d) a light chain variable region CDR1 comprising SEQ ID NO: 38;
(e) a light chain variable region CDR2 comprising SEQ ID NO: 45; and
(f) a light chain variable region CDR3 comprising SEQ ID NO: 53.

In another preferred embodiment, the antibody comprises:
(a) a heavy chain variable region CDR1 comprising SEQ ID NO: 18;
(b) a heavy chain variable region CDR2 comprising SEQ ID NO: 25;
(c) a heavy chain variable region CDR3 comprising SEQ ID NO: 32;
(d) a light chain variable region CDR1 comprising SEQ ID NO: 39;
(e) a light chain variable region CDR2 comprising SEQ ID NO: 46; and
(f) a light chain variable region CDR3 comprising SEQ ID NO: 54.

In another preferred embodiment, the antibody comprises:
(a) a heavy chain variable region CDR1 comprising SEQ ID NO: 19;
(b) a heavy chain variable region CDR2 comprising SEQ ID NO: 26;
(c) a heavy chain variable region CDR3 comprising SEQ ID NO: 33;
(d) a light chain variable region CDR1 comprising SEQ ID NO: 40;
(e) a light chain variable region CDR2 comprising SEQ ID NO: 47; and
(f) a light chain variable region CDR3 comprising SEQ ID NO: 55.

In another preferred embodiment, the antibody comprises:
(a) a heavy chain variable region CDR1 comprising SEQ ID NO: 20;
(b) a heavy chain variable region CDR2 comprising SEQ ID NO: 27;
(c) a heavy chain variable region CDR3 comprising SEQ ID NO: 34;
(d) a light chain variable region CDR1 comprising SEQ ID NO: 41;
(e) a light chain variable region CDR2 comprising SEQ ID NO: 48; and
(f) a light chain variable region CDR3 comprising SEQ ID NO: 56.

In another preferred embodiment, the antibody comprises:
(a) a heavy chain variable region CDR1 comprising SEQ ID NO: 21;
(b) a heavy chain variable region CDR2 comprising SEQ ID NO: 28;
(c) a heavy chain variable region CDR3 comprising SEQ ID NO: 35;
(d) a light chain variable region CDR1 comprising SEQ ID NO: 42;
(e) a light chain variable region CD2 comprising SEQ ID NO: 49; and (f) a light chain variable region CDR3 comprising SEQ ID NO: 57.

In another preferred embodiment, the antibody comprises:
(a) a heavy chain variable region CDR1 comprising SEQ ID NO: 22;
(b) a heavy chain variable region CDR2 comprising SEQ ID NO: 29;
(c) a heavy chain variable region CDR3 comprising SEQ ID NO: 36;
(d) a light chain variable region CDR1 comprising SEQ ID NO: 43;
(e) a light chain variable region CDR2 comprising SEQ ID NO: 50; and
(f) a light chain variable region CDR3 comprising SEQ ID NO: 58.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., *British J. of Cancer* 83(2):252-260 (2000) (describing the production of a humanized anti-CD30 antibody using only the heavy chain variable domain CDR3 of murine anti-CD30 antibody Ki-4); Beiboer et al., *J. Mol. Biol.* 296:833-849 (2000) (describing recombinant epithelial glycoprotein-2 (EGP-2) antibodies using only the heavy chain CDR3 sequence of the parental murine MOC-31 anti-EGP-2 antibody); Rader et al., *Proc. Natl. Acad. Sci. U.S.A.* 95:8910-8915 (1998) (describing a panel of humanized anti-integrin $\alpha_v\beta_3$ antibodies using a heavy and light chain variable CDR3 domain of a murine anti-integrin $\alpha_v\beta_3$ antibody LM609 wherein each member antibody comprises a distinct sequence outside the CDR3 domain and capable of binding the same epitope as the parent muring antibody with affinities as high or higher than the parent murine antibody); Barbas et al., *J. Am. Chem. Soc.* 116:2161-2162 (1994) (disclosing that the CDR3 domain provides the most significant contribution to antigen binding); Barbas et al., *Proc. Natl. Acad. Sci. U.S.A.* 92:2529-2533 (1995) (describing the grafting of heavy chain CDR3 sequences of three Fabs (SI-1, SI-40, and SI-32) against human placental DNA onto the heavy chain of an anti-tetanus toxoid Fab thereby replacing the existing heavy chain CDR3 and demonstrating that the CDR3 domain alone conferred binding specificity); and Ditzel et al., *J. Immunol.* 157:739-749 (1996) (describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab). Each of these references is hereby incorporated by reference in its entirety.

Accordingly, the present invention provides monoclonal antibodies comprising one or more heavy and/or light chain CDR3 domains from an antibody derived from a human or non-human animal, wherein the monoclonal antibody is capable of specifically binding to CD19. Within certain aspects, the present invention provides monoclonal antibodies comprising one or more heavy and/or light chain CDR3 domains from a non-human antibody, such as a mouse or rat antibody, wherein the monoclonal antibody is capable of specifically binding to CD19. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present invention provides monoclonal antibodies comprising one or more heavy and/or light chain CDR3 domain from a human antibody, such as, for example, a human antibody obtained from a non-human animal, wherein the human antibody is capable of specifically binding to CD19. Within other aspects, the present invention provides monoclonal antibodies comprising one or more heavy and/or light chain CDR3 domain from a first human antibody, such as, for example, a human antibody obtained from a non-human animal, wherein the first human antibody is capable of specifically binding to CD19 and wherein the CDR3 domain from the first human antibody replaces a CDR3 domain in a human antibody that is lacking binding specificity for CD19 to generate a second human antibody that is capable of specifically binding to CD19. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody.

Antibodies Having Particular Germline Sequences

In certain embodiments, an antibody of the invention comprises a heavy chain variable region from a particular germline heavy chain immunoglobulin gene and/or a light chain variable region from a particular germline light chain immunoglobulin gene.

For example, in a preferred embodiment, the invention provides an isolated monoclonal antibody, or an antigen-binding portion thereof, comprising a heavy chain variable region that is the product of or derived from a human $V_H$ 5-51 gene, wherein the antibody specifically binds CD19. In another preferred embodiment, the invention provides an isolated monoclonal antibody, or an antigen-binding portion thereof, comprising a heavy chain variable region that is the product of or derived from a human $V_H$ 1-69 gene, wherein the antibody specifically binds CD19. In yet another preferred embodiment, the invention provides an isolated monoclonal antibody, or an antigen-binding portion thereof, comprising a light chain variable region that is the product of or derived from a human $V_K$ L18 gene, wherein the antibody specifically binds CD19. In yet another preferred embodiment, the invention provides an isolated monoclonal antibody, or an antigen-binding portion thereof, comprising a light chain variable region that is the product of or derived from a human $V_K$ A27 gene, wherein the antibody specifically binds CD19. In yet another preferred embodiment, the invention provides an isolated monoclonal antibody, or an antigen-binding portion thereof, comprising a light chain variable region that is the product of or derived from a human $V_K$ L15 gene, wherein the antibody specifically binds CD19. In yet another preferred embodiment, the invention provides an isolated monoclonal antibody, or antigen-binding portion thereof, wherein the antibody:
(a) comprises a heavy chain variable region that is the product of or derived from a human $V_H$ 5-51 or 1-69 gene (which genes encode the amino acid sequences set forth in SEQ ID NOs: 74 and 75, respectively);
(b) comprises a light chain variable region that is the product of or derived from a human $V_K$ L18, $V_K$ A27 or $V_K$ L15 gene (which genes encode the amino acid sequences set forth in SEQ ID NOs: 76, 77 and 78, respectively); and
(c) specifically binds to CD19, preferably human CD19.

Examples of antibodies having $V_H$ and $V_K$ of $V_H$ 5-51 and $V_K$ L18, respectively, are 21D4, 21D4a, 27F3, 5G7, 13F1 and 46E8. An example of an antibody having $V_H$ and $V_K$ of $V_H$ 1-69 and V$_K$ A27, respectively, is 47G4. An example of an antibody having V$_H$ and V$_K$ of V$_H$ 1-69 and V$_K$ L15, respectively, is 3C10.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the invention comprises heavy and light chain variable regions comprising amino acid sequences that are homologous to the amino acid sequences of the preferred antibodies described herein, and wherein the antibodies retain the desired functional properties of the anti-CD19 antibodies of the invention.

For example, the invention provides an isolated monoclonal antibody, or antigen binding portion thereof, comprising a heavy chain variable region and a light chain variable region, wherein:
  (a) the heavy chain variable region comprises an amino acid sequence that is at least 80% homologous to an amino acid sequence selected from the group consisting of SEQ ID NOs: 1, 2, 3, 4, 5, 6 and 7;
  (b) the light chain variable region comprises an amino acid sequence that is at least 80% homologous to an amino acid sequence selected from the group consisting of SEQ ID NOs: 8, 9, 10, 11, 12, 13, 14 and 15;
  (c) the antibody binds to human CD19 with a K$_D$ of $1\times10^{-7}$ M or less;
  (d) binds to Raji and Daudi B-ell tumor cells.

In various embodiments, the antibody can be, for example, a human antibody, a humanized antibody or a chimeric antibody.

In other embodiments, the V$_H$ and/or V$_L$ amino acid sequences may be 85%, 90%, 95%, 96%, 97%, 98% or 99% homologous to the sequences set forth above. An antibody having V$_H$ and V$_L$ regions having high (i.e., 80% or greater) homology to the V$_H$ and V$_L$ regions of the sequences set forth above, can be obtained by mutagenesis (e.g., site-directed or PCR-mediated mutagenesis) of nucleic acid molecules encoding SEQ ID NOs: 59, 60, 61, 62, 63, 64, 65, 66, 67, 68, 69, 70, 71, 72 or 73, followed by testing of the encoded altered antibody for retained function (i.e., the functions set forth in (c) through (d) above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions ×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can be further used as a "query sequence" for searching public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See www.ncbi.nlm.nih.gov.

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 21D4, 21D4a, 47G4, 27F3, 3C10, 5G7, 13F1 or 46E8), or conservative modifications thereof, and wherein the antibodies retain the desired functional properties of the anti-CD19 antibodies of the invention. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:
- (a) the heavy chain variable region CDR3 sequence comprises an amino acid sequence selected from the group consisting of amino acid sequences of SEQ ID NOs: 30, 31, 32, 33, 34, 35 and 36, and conservative modifications thereof;
- (b) the light chain variable region CDR3 sequence comprises an amino acid sequence selected from the group consisting of amino acid sequence of SEQ ID NOs: 51, 52, 53, 54, 55, 56, 57 and 58, and conservative modifications thereof;
- (c) the antibody binds to human CD19 with a $K_D$ of $1 \times 10^{-7}$ M or less;
- (d) binds to Raji and Daudi B-cell tumor cells.

In a preferred embodiment, the heavy chain variable region CDR2 sequence comprises an amino acid sequence selected from the group consisting of amino acid sequences of SEQ ID NOs: 23, 24, 25, 26, 27, 28 and 29, and conservative modifications thereof; and the light chain variable region CDR2 sequence comprises an amino acid sequence selected from the group consisting of amino acid sequences of SEQ ID NOs: 44, 45, 46, 47, 48, 49 and 50, and conservative modifications thereof. In another preferred embodiment, the heavy chain variable region CDR1 sequence comprises an amino acid sequence selected from the group consisting of amino acid sequences of SEQ ID NOs: 16, 17, 18, 19, 20, 21 and 22, and conservative modifications thereof; and the light chain variable region CDR1 sequence comprises an amino acid sequence selected from the group consisting of amino acid sequences of SEQ ID NOs: 37, 38, 39, 40, 41, 42 and 43, and conservative modifications thereof.

In various embodiments, the antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c) through (d) above) using the functional assays described herein.

Antibodies that Bind to the Same Epitope as Anti-CD 19 Antibodies of the Invention In another embodiment, the invention provides antibodies that bind to the same epitope on human CD19 as any of the CD19 monoclonal antibodies of the invention (i.e., antibodies that have the ability to cross-compete for binding to CD19 with any of the monoclonal antibodies of the invention). In preferred embodiments, the reference antibody for cross-competition studies can be the monoclonal antibody 21D4 (having $V_H$ and $V_L$ sequences as shown in SEQ ID NOs: 1 and 8, respectively), or the monoclonal antibody 21D4a (having $V_H$ and $V_L$ sequences as shown in SEQ ID NOs: 1 and 9, respectively), or the monoclonal antibody 47G4 (having $V_H$ and $V_L$ sequences as shown in SEQ ID NOs: 2 and 10, respectively), or the monoclonal antibody 27F3 (having $V_H$ and $V_L$ sequences as shown in SEQ ID NOs: 3 and 11, respectively), or the monoclonal antibody 3C10 (having $V_H$ and $V_L$ sequences as shown in SEQ ID NOs: 4 and 12, respectively), or the monoclonal antibody 5G7 (having $V_H$ and $V_L$ sequences as shown in SEQ ID NOs: 5 and 13, respectively), or the monoclonal antibody 13F1 (having $V_H$ and $V_L$ sequences as shown in SEQ ID NOs: 6 and 14, respectively), or the monoclonal antibody 46E8 (having $V_H$ and $V_L$ sequences as shown in SEQ ID NOs: 7 and 15, respectively. Such cross-competing antibodies can be identified based on their ability to cross-compete with 21D4, 21D4a, 47G4, 27F3, 3C10, 5G7, 13F1 or 46E8 in standard CD19 binding assays. For example, BIAcore® analysis, ELISA assays or flow cytometry may be used to demonstrate cross-competition with the antibodies of the current invention. The ability of a test antibody to inhibit the binding of, for example, 21D4, 21D4a, 47G4, 27F3, 3C10, 5G7, 13F1 or 46E8, to human CD19 demonstrates that the test antibody can compete with 21D4, 21D4a, 47G4, 27F3, 3C10, 5G7, 13F1 or 46E8 for binding to human CD19 and thus binds to the same epitope on human CD19 as 21D4, 21D4a, 47G4, 27F3, 3C10, 5G7, 13F1 or 46E8. In a preferred embodiment, the antibody that binds to the same epitope on human CD19 as 21D4, 21D4a, 47G4, 27F3, 3C10, 5G7, 13F1 or 46E8 is a human monoclonal antibody. Such human monoclonal antibodies can be prepared and isolated as described in the Examples.

Engineered and Modified Antibodies

An antibody having one or more of the $V_H$ and/or $V_L$ sequences disclosed herein can be used as starting material to engineer a modified antibody, which modified antibody may have altered properties as compared to the starting antibody. An antibody can be engineered by modifying one or more amino acids within one or both variable regions (i.e., $V_H$ and/or $V_L$), for example, within one or more CDR regions and/or within one or more framework regions. Additionally or alternatively, an antibody can be engineered by modifying residues within the constant region(s), for example, to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See.*

U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs: 16, 17, 18, 19, 20, 21 and 22, SEQ ID NOs: 23, 24, 25, 26, 27, 28 and 29, and SEQ ID NOs: 30, 31, 32, 33, 34, 35 and 36, respectively, and a light chain variable region comprising CDR1, CDR2, and CDR3 sequences comprising an amino acid sequence selected from the group consisting of SEQ ID NOs: 37, 38, 39, 40, 41, 42 and 43, SEQ ID NOs: 44, 45, 46, 47, 48, 49 and 50, and SEQ ID NOs: 51, 52, 53, 54, 55, 56, 57 and 58, respectively. Thus, such antibodies contain the $V_H$ and $V_L$ CDR sequences of monoclonal antibodies 21D4, 21D4a, 47G4, 27F3, 3C10, 5G7, 13F1 or 46E8 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" J. Mol. Biol. 227:776-798; and Cox, J. P. L. et al. (1994) "A Directory of Human Germ-line $V_H$ Segments Reveals a Strong Bias in their Usage" Eur. J. Immunol. 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank accession numbers: 1-69 (NG_0010109 NT_024637 and BC070333), 3-33 (NG_0010109 and NT_024637) and 3-7 (NG_0010109 and NT_024637). As another example, the following heavy chain germline sequences found in the HCo12 HuMAb mouse are available in the accompanying Genbank accession numbers: 1-69 (NG_0010109, NT_024637 and BC070333), 5-51 NG_0010109 and NT_024637), 4-34 (NG_0010109 and NT_024637), 3-30.3 (CAJ556644) and 3-23 (AJ406678).

Antibody protein sequences are compared against a compiled protein sequence database using one of the sequence similarity searching methods called the Gapped BLAST (Altschul et al. (1997) Nucleic Acids Research 25:3389-3402), which is well known to those skilled in the art. BLAST is a heuristic algorithm in that a statistically significant alignment between the antibody sequence and the database sequence is likely to contain high-scoring segment pairs (HSP) of aligned words. Segment pairs whose scores cannot be improved by extension or trimming is called a hit. Briefly, the nucleotide sequences of VBASE origin (http://vbase.mrc-cpe.cam.ac.uk/vbase1/list2.php) are translated and the region between and including FR1 through FR3 framework region is retained. The database sequences have an average length of 98 residues. Duplicate sequences which are exact matches over the entire length of the protein are removed. A BLAST search for proteins using the program blastp with default, standard parameters except the low complexity filter, which is turned off, and the substitution matrix of BLOSUM62, filters for top 5 hits yielding sequence matches. The nucleotide sequences are translated in all six frames and the frame with no stop codons in the matching segment of the database sequence is considered the potential hit. This is in turn confirmed using the BLAST program tblastx, which translates the antibody sequence in all six frames and compares those translations to the VBASE nucleotide sequences dynamically translated in all six frames.

The identities are exact amino acid matches between the antibody sequence and the protein database over the entire length of the sequence. The positives (identities+substitution match) are not identical but amino acid substitutions guided by the BLOSUM62 substitution matrix. If the antibody sequence matches two of the database sequences with same identity, the hit with most positives would be decided to be the matching sequence hit.

Preferred framework sequences for use in the antibodies of the invention are those that are structurally similar to the framework sequences used by selected antibodies of the invention, e.g., similar to the $V_H$ 5-51 framework sequences (SEQ ID NO: 74) and/or the $V_H$ 1-69 framework sequences (SEQ ID NO: 75) and/or the $V_K$ L18 framework sequences (SEQ ID NO: 76) and/or the $V_K$ A27 framework sequence (SEQ ID NO: 77) and/or the $V_K$ L15 framework sequence (SEQ ID NO: 78) used by preferred monoclonal antibodies of the invention. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the instant disclosure provides isolated anti-CD19 monoclonal antibodies, or antigen binding portions thereof, comprising a heavy chain variable region comprising: (a) a $V_H$ CDR1 region comprising an amino acid sequence selected from the group consisting of SEQ ID NOs: 16, 17, 18, 19, 20, 21 and 22, or an amino acid sequence having one, two, three, four or five amino acid substitutions, deletions or additions as compared to SEQ ID NOs: 16, 17, 18, 19, 20, 21 and 22; (b) a $V_H$ CDR2 region comprising an amino acid sequence selected from the group consisting of SEQ ID NOs: 23, 24, 25, 26, 27, 28 and 29, or an amino acid sequence having one, two, three, four or five amino acid substitutions, deletions or additions as compared to SEQ ID NOs: 23, 24, 25, 26, 27, 28 and 29; (c) a $V_H$ CDR3 region comprising an amino acid sequence selected from the group consisting of SEQ ID NOs: 30, 31, 32, 33, 34, 35 and 36, or an amino acid sequence having one, two, three, four or five amino acid substitutions, deletions or additions as compared to SEQ ID NOs: 30, 31, 32, 33, 34, 35 and 36; (d) a $V_K$ CDR1 region comprising an amino acid sequence selected from the group consisting of SEQ ID NOs: 37, 38, 39, 40, 41, 42 and 43, or an amino acid sequence having one, two, three, four or five amino acid substitutions, deletions or additions as compared to SEQ ID NOs: 37, 38, 39, 40, 41, 42 and 43; (e) a $V_K$ CDR2 region comprising an amino acid sequence selected from the group consisting of SEQ ID NOs: 44, 45, 46, 47, 48, 49 and 50, or an amino acid sequence having one, two, three, four or five amino acid substitutions, deletions or additions as compared to SEQ ID NOs: 44, 45, 46, 47, 48, 49 and 50; and (f) a $V_K$ CDR3 region comprising an amino acid sequence selected from the group consisting of SEQ ID NOs: 51, 52, 53, 54, 55, 56, 57 and 58, or an amino acid sequence having one, two, three, four or five amino acid substitutions, deletions or additions as compared to SEQ ID NOs: 51, 52, 53, 54, 55, 56, 57 and 58.

Engineered antibodies of the invention include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

For example, Table 1 below shows a number of amino acid changes in the framework regions of the anti-PD-1 antibodies 17D8, 2D3, 4H1, 5C4, 4A11, 7D3 and SF4 that differ from the heavy chain parent germline sequence. To return one or more of the amino acid residues in the framework region sequences to their germline configuration, the somatic mutations can be "backmutated" to the germline sequence by, for example, site-directed mutagenesis or PCR-mediated mutagenesis.

TABLE 1

Modifications to antibodies 17D8, 2D3, 4H1, 5C4, 4A11, 7D3 and 5F4 from the heavy chain germline configuration.

| Anti-CD19 Ab | Amino acid position | Amino acid of antibody | Original amino acid of germline configuration |
|---|---|---|---|
| 21D4 | 30 | S | T |
|  | 77 | R | S |
| 21D4a | 30 | S | T |
|  | 77 | R | S |
| 47G4 | 24 | D | A |
| 3C10 | 77 | N | S |
|  | 88 | A | S |
| 5G7 | 19 | N | K |
|  | 77 | N | S |
| 13F1 | 19 | Q | K |
|  | 28 | T | S |
|  | 85 | G | S |
| 46E8 | 19 | Q | K |
|  | 28 | T | S |
|  | 85 | G | S |

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CHI is modified such that the number of cysteine residues in the hinge region is altered, e.g., increased or decreased. This approach is described further in U.S. Pat. No. 5,677,425 by Bodmer et al. The number of cysteine residues in the hinge region of CHI is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or $C_L$ region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 2316, 17, 18, 19, 20, 21 and 2239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/142072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) *Biochem.* 14:5516-23).

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivative other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Antibody Physical Properties

The antibodies of the present invention may be further characterized by the various physical properties of the anti-CD19 antibodies. Various assays may be used to detect and/or differentiate different classes of antibodies based on these physical properties.

In some embodiments, antibodies of the present invention may contain one or more glycosylation sites in either the light or heavy chain variable region. The presence of one or more glycosylation sites in the variable region may result in increased immunogenicity of the antibody or an alteration of the pK of the antibody due to altered antigen binding (Marshall et at (1972) *Annu Rev Biochem* 41:673-702; Gala FA and Morrison SL (2004) *J Immunol* 172:5489-94; Wallick et al (1988) *J Exp Med* 168:1099-109; Spiro R G (2002) *Glycobiology* 12:43 R-56R; Parekh et al (1985) *Nature* 316:452-7; Mimura et al. (2000) *Mol Immunol* 37:697-706). Glycosylation has been known to occur at motifs containing an N-X-S/T sequence. Variable region glycosylation may be tested using a Glycoblot assay, which cleaves the antibody to produce a Fab, and then tests for glycosylation using an assay that measures periodate oxidation and Schiff base formation. Alternatively, variable region glycosylation may be tested using Dionex light chromatography (Dionex-LC), which cleaves saccharides from a Fab into monosaccharides and analyzes the individual saccharide content. In some instances, it is preferred to have an anti-CD19 antibody that does not contain variable region glycosylation. This can be achieved either by selecting antibodies that do not contain the glycosylation motif in the variable region or by mutating residues within the glycosylation motif using standard techniques well known in the art.

In a preferred embodiment, the antibodies of the present invention do not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain. The creation of isoaspartic acid can be measured using an iso-quant assay, which uses a reverse-phase HPLC to test for isoaspartic acid.

Each antibody will have a unique isoelectric point (pI), but generally antibodies will fall in the pH range of between 6 and 9.5. The pI for an IgG1 antibody typically falls within the pH range of 7-9.5 and the pI for an IgG4 antibody typically falls within the pH range of 6-8. Antibodies may have a pI that is outside this range. Although the effects are generally unknown, there is speculation that antibodies with a pI outside the normal range may have some unfolding and instability under in vivo conditions. The isoelectric point may be tested using a capillary isoelectric focusing assay, which creates a pH gradient and may utilize laser focusing for increased accuracy (Janini et al (2002) *Electrophoresis* 23:1605-11; Ma et al. (2001) *Chromatographia* 53:S75-89; Hunt et al (1998) *J Chromatogr A* 800:355-67). In some instances, it is preferred to have an anti-CD19 antibody that contains a pI value that falls in the normal range. This can be achieved either by selecting antibodies with a pI in the normal range, or by mutating charged surface residues using standard techniques well known in the art.

Each antibody will have a melting temperature that is indicative of thermal stability (Krishnamurthy R and Manning MC (2002) *Curr Pharm Biotechnol* 3:361-71). A higher thermal stability indicates greater overall antibody stability in vivo. The melting point of an antibody may be measure using techniques such as differential scanning calorimetry (Chen et al (2003) *Pharm Res* 20:1952-60; Ghirlando et al (1999) *Immunol Lett* 68:47-52). $T_{M1}$ indicates the temperature of the initial unfolding of the antibody. $T_{M2}$ indicates the temperature of complete unfolding of the antibody. Generally, it is preferred that the $T_{M1}$ of an antibody of the present invention is greater than 60° C., preferably greater than 65° C., even more preferably greater than 70° C. Alternatively, the thermal stability of an antibody may be measure using circular dichroism (Murray et al. (2002) *J. Chromatogr Sci* 40:343-9).

In a preferred embodiment, antibodies are selected that do not rapidly degrade. Fragmentation of an anti-CD19 antibody may be measured using capillary electrophoresis (CE) and MALDI-MS, as is well understood in the art (Alexander A J and Hughes D E (1995) *Anal Chem* 67:3626-32).

In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

Methods of Engineering Antibodies

As discussed above, the anti-CD19 antibodies having $V_H$ and $V_K$ sequences disclosed herein can be used to create new anti-CD19 antibodies by modifying the $V_H$ and/or $V_K$ sequences, or the constant region(s) attached thereto. Thus, in another aspect of the invention, the structural features of an anti-CD19 antibody of the invention, e.g. 21D4, 21D4a, 47G4, 27F3, 3C10, 5G7, 13F1 or 46E8, are used to create structurally related anti-CD19 antibodies that retain at least one functional property of the antibodies of the invention, such as binding to human CD19. For example, one or more CDR regions of 21D4, 21D4a, 47G4, 27F3, 3C10, 5G7, 13F1 or 46E8, or mutations thereof, can be combined recombinantly with known framework regions and/or other CDRs to create additional, recombinantly-engineered, anti-CD19 antibodies of the invention, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-CD19 antibody comprising:

(a) providing: (i) a heavy chain variable region antibody sequence comprising a CDR1 sequence selected from the group consisting of SEQ ID NOs: 16, 17, 18, 19, 20, 21 and 22, a CDR2 sequence selected from the group consisting of SEQ ID NOs: 23, 24, 25, 26, 27, 28 and 29, and/or a CDR3 sequence selected from the group consisting of SEQ ID NOs: 30, 31, 32, 33, 34, 35 and 36; and/or (ii) a light chain variable region antibody sequence comprising a CDR1 sequence selected from the group consisting of SEQ ID NOs: 37, 38, 39, 40, 41, 42 and 43, a CDR2 sequence selected from the group consisting of SEQ ID NOs: 44, 45, 46, 47, 48, 49 and 50, and/or a CDR3 sequence selected from the group consisting of SEQ ID NOs: 51, 52, 53, 54, 55, 56, 57 and 58;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-CD19 antibodies described herein, which functional properties include, but are not limited to:

(i) binds to human CD19 with a $K_D$ of $1 \times 10^{-7}$ M or less;

(ii) binds to Raji and Daudi B-cell tumor cells.

The functional properties of the altered antibodies can be assessed using standard assays available in the art and/or described herein, such as those set forth in the Examples (e.g., flow cytometry, binding assays).

In certain embodiments of the methods of engineering antibodies of the invention, mutations can be introduced randomly or selectively along all or part of an anti-CD19 antibody coding sequence and the resulting modified anti-CD19 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), one or more nucleic acids encoding the antibody can be recovered from the library.

Preferred nucleic acids molecules of the invention are those encoding the $V_H$ and $V_L$ sequences of the 21D4, 21D4a, 47G4, 27F3, 3C10, 5G7, 13F1 or 46E8 monoclonal antibodies. DNA sequences encoding the $V_H$ sequences of 21D4, 21D4a, 47G4, 23, 3C10, 5G7, 13F1 and 46E8 are shown in SEQ ID NOs: 59, 60, 61, 62, 63, 64 and 65, respectively. DNA sequences encoding the $V_L$ sequences of 21D4, 21D4a, 47G4, 27F3, 3C10, 5G7, 13F1 and 46E8 are shown in SEQ ID NOs: 66, 67, 68, 69, 70, 71, 72 and 73, respectively.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence $(Gly_4-Ser)_3$, such that the $V_H$ and $V_L$ sequences can be expressed as a contiguous single-chain protein, with the $V_L$ and $V_H$ regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Production of Monoclonal Antibodies

Monoclonal antibodies (mAbs) of the present invention can be produced by a variety of techniques, including conventional monoclonal antibody methodology e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the invention are human monoclonal antibodies. Such human monoclonal antibodies directed against CD19 can be generated using transgenic or transchromosomic mice carrying parts of the human immune system rather than the mouse system. These transgenic and transchromosomic mice include mice referred to herein as the HuMAb Mouse® and KM Mouse®, respectively, and are collectively referred to herein as "human Ig mice."

The HuMAb Mouse® (Medarex®, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). Preparation and use of the HuMAb Mouse®, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM Mice™", are described in detail in PCT Publication WO 02/43478 to Ishida et al.

Still further, alternative transgenic animal systems expressing human immunoglobulin genes are available in the art and can be used to raise anti-CD19 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-CD19 antibodies of the invention. For example, mice carrying both a human heavy chain transchromosome and a human light chain tranchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-CD19 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,9130, 31, 32, 33, 34, 35 and 36,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the invention, such mice can be immunized with a purified or enriched preparation of CD19 antigen and/or recombinant CD19, or cells expressing CD19, or an CD19 fusion protein, as described by Lonberg, N. et al. (1994) *Nature* 368(6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first infusion. For example, a purified or recombinant preparation (5-50 μg) of CD19 antigen can be used to immunize the human Ig mice intraperitoneally.

Detailed procedures to generate fully human monoclonal antibodies to CD19 are described in Example 1 below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-CD19 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12). Alternatively or additionally, the KM Mouse® strain can be used, as described in Example 1.

Generation of Hybridomas Producing Human Monoclonal Antibodies

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3×63-Ag8.653 nonsecreting mouse myeloma cells (ATCC, CRL 1580) with 50% PEG. Alternatively, the single cell suspension of splenic lymphocytes from immunized mice can be fused using an electric field based electrofusion method, using a CytoPulse large chamber cell fusion electroporator (CytoPulse Sciences, Inc., Glen Burnie Md.). Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days.

The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies

Antibodies of the invention also can be produced in a host cell transfectoma using, for example, a combination of recombinant DNA techniques and gene transfection methods as is well known in the art (e.g., Morrison, S. (1985) *Science* 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr− host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr− CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP 338,841 (to Bebbington). When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of the invention can be tested for binding to CD19 by, for example, standard ELISA. Briefly, microtiter plates are coated with purified CD19 at 0.25 µg/ml in PBS, and then blocked with 5% bovine serum albumin in PBS. Dilutions of antibody (e.g., dilutions of plasma from CD19-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with CD19 immunogen. Hybridomas that bind with high avidity to CD19 are subcloned and further characterized. One clone from each hybridoma, which retains the reactivity of the parent cells (by ELISA), can be chosen for making a 5-10 vial cell bank stored at −140° C., and for antibody purification.

To purify anti-CD19 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected anti-CD19 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using CD19 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4° C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-CD19 human IgGs can be further tested for reactivity with CD19 antigen by Western blotting. Briefly, CD19 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Immunoconjugates

In another aspect, the present invention features an anti-CD19 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg®; American Home Products).

Cytotoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Method for preparing radioimmunconjugates are established in the art. Examples of radioimmunoconjugates are commercially available, including Zevalin® (IDEC Pharmaceuticals) and Bexxar® (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., *Immunol. Rev.*, 62:119-58 (1982).

Bispecific Molecules

In another aspect, the present invention features bispecific molecules comprising an anti-CD19 antibody, or a fragment thereof of the invention. An antibody of the invention, or antigen-binding portions thereof can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for CD19 and a second binding specificity for a second target epitope. In a particular embodiment of the invention, the second target epitope is an Fc receptor, e.g., human FcγRI (CD64) or a human Fcα receptor (CD89). Therefore, the invention includes bispecific molecules capable of binding both to FcγR or FcαR expressing effector cells (e.g., monocytes, macrophages or polymorphonuclear cells (PMNs)), and to target cells expressing CD19. These bispecific molecules target CD19 expressing cells to effector cell and trigger Fc receptor-mediated effector cell activities, such as phagocytosis of an CD19 expressing cells, antibody dependent cell-mediated cytotoxicity (ADCC), cytokine release, or generation of superoxide anion.

In an embodiment of the invention in which the bispecific molecule is multispecific, the molecule can further include a third binding specificity, in addition to an anti-Fc binding specificity and an anti-CD19 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', F(ab')$_2$, Fv, Fd, dAb or a single chain Fv. The antibody may also be a light chain or heavy chain dimer, or any minimal fragment thereof such as a Fv or a single chain construct as described in U.S. Pat. No. 4,946,778 to Ladner et al., the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII (CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ M$^{-1}$).

The production and characterization of certain preferred anti-Fcγ monoclonal antibodies are described in PCT Publication WO 88/00052 and in U.S. Pat. No. 4,954,617 to Fanger et al., the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the 1H22 antibody is described in Graziano, R. F. et al. (1995) *J. Immunol* 155 (10): 4996-5002 and PCT Publication WO 94/10332 to Tempest et al. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5 \times 10^7$ M$^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148: 1764).

FcαRI and FcγRI are preferred trigger receptors for use in the bispecific molecules of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); and (4) mediate enhanced antigen presentation of antigens, including self-antigens, targeted to them.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-CD19 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g. Karpovsky et al. (1984) *J. Exp. Med.* 160: 1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83, and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858, all of which are expressly incorporated herein by reference.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g. an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-CD19 antibody of the present invention combined with at least one other anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-CD19 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-CD19 antibody of the invention preferably results in a decrease in severity of disease symptoms, an increase in frequency and duration of disease symptom-free periods, or a prevention of impairment or disability due to the disease affliction. For example, for the treatment of CD19$^+$ tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* L233:134); p120 (Schreier et al. (1994) *J. Biol. Chem.* 269:9090); see also K. Keinanen; M. L. Laukkanen (1994) FEBS Lett. 346:123; J. J. Killion; I. J. Fidler (1994) *Immunomethods* 4:273.

Uses and Methods

The antibodies, particularly the human antibodies, antibody compositions and methods of the present invention have numerous in vitro and in vivo diagnostic and therapeutic utilities involving the diagnosis and treatment of CD19 mediated disorders. For example, these molecules can be administered to cells in culture, in vitro or ex vivo, or to human subjects, e.g., in vivo, to treat, prevent and to diagnose a variety of disorders. As used herein, the term "subject" is intended to include human and non-human animals. Non-human animals include all vertebrates, e.g., mammals and non-mammals, such as non-human primates, sheep, dogs, cats, cows, horses, chickens, amphibians, and reptiles. Preferred subjects include human patients having disorders mediated by CD19 activity. The methods are particularly suitable for treating human patients having a disorder associated with aberrant CD19 expression. When antibodies to CD19 are administered together with another agent, the two can be administered in either order or simultaneously.

Given the specific binding of the antibodies of the invention for CD19, the antibodies of the invention can be used to specifically detect CD19 expression on the surface of cells and, moreover, can be used to purify CD19 via immunoaffinity purification.

Furthermore, given the expression of CD19 on various tumor cells, the human antibodies, antibody compositions and methods of the present invention can be used to treat a subject with a tumorigenic disorder, e.g., a disorder characterized by the presence of tumor cells expressing CD19 including, for example, non-Hodgkin's lymphoma (NHL), acute lymphocytic leukemia (ALL), chronic lymphocytic leukemia (CLL), Burkitt's lymphoma, anaplastic large-cell lymphomas (ALCL), multiple myeloma, cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-ell leukemia (T-ALL), entroblastic/centrocytic (cb/cc) follicular lymphomas cancers, diffuse large cell lymphomas of B lineage, angioimmunoblastic lymphadenopathy (AILD)-like T cell lymphoma, HIV associated body cavity based lymphomas, Embryonal Carcinomas, undifferentiated carcinomas of the rhino-pharynx (e.g., Schmincke's tumor), Castleman's disease, Kaposi's Sarcoma, Multiple Myeloma, Waldenstrom's macroglobulinemia, and other B-cell lymphomas.

Additionally, overexpression of CD19 may lead to loss of B-cell tolerance and generation of autoimmune disorders (Tedder et al. (2005) *Curr Dir Autoimmun* 8:55). This autoimmune effect has been seen by the accumulation of CD19+ B-cells in the inflamed joints of rheumatoid arthritis patients (He et al. (2001) *J Rheumatol* 28:2168). As such, the human antibodies, antibody compositions and methods of the present invention can be used to treat a subject with an autoimmune disorder, e.g., a disorder characterized by the presence of B-cells expressing CD19 including, for example, rheumatoid arthritis.

In one embodiment, the antibodies (e.g., human monoclonal antibodies, multispecific and bispecific molecules and compositions) of the invention can be used to detect levels of CD19, or levels of cells which contain CD19 on their membrane surface, which levels can then be linked to certain disease symptoms. Alternatively, the antibodies can be used to inhibit or block CD19 function which, in turn, can be linked to the prevention or amelioration of certain disease symptoms, thereby implicating CD19 as a mediator of the disease. This can be achieved by contacting a sample and a control sample with the anti-CD19 antibody under conditions that allow for the formation of a complex between the antibody and CD19. Any complexes formed between the antibody and CD19 are detected and compared in the sample and the control.

In another embodiment, the antibodies (e.g., human antibodies, multispecific and bispecific molecules and compositions) of the invention can be initially tested for binding activity associated with therapeutic or diagnostic use in vitro. For example, compositions of the invention can be tested using the flow cytometric assays described in the Examples below.

The antibodies (e.g., human antibodies, multispecific and bispecific molecules, immunoconjugates and compositions) of the invention have additional utility in therapy and diagnosis of CD19-related diseases. For example, the human monoclonal antibodies, the multispecific or bispecific molecules and the immunoconjugates can be used to elicit in vivo or in vitro one or more of the following biological activities: to inhibit the growth of and/or kill a cell expressing CD19; to mediate phagocytosis or ADCC of a cell expressing CD19 in the presence of human effector cells, or to block CD19 ligand binding to CD19.

In a particular embodiment, the antibodies (e.g., human antibodies, multispecific and bispecific molecules and compositions) are used in vivo to treat, prevent or diagnose a variety of CD19-related diseases. Examples of CD19-related diseases include, among others, autoimmune disorders, rheumatoid arthritis, cancer, non-Hodgkin's lymphoma, acute lymphocytic leukemia (ALL), chronic lymphocytic leukemia (CLL), Burkitt's lymphoma, anaplastic large-cell lymphomas (ALCL), multiple myeloma, cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (F-ALL), entroblastic/centrocytic (cb/cc) follicular lymphomas cancers, diffuse large cell lymphomas of B lineage, angioimmunoblastic lymphadenopathy (AILD)-like T cell lymphoma, HIV associated body cavity based lymphomas, Embryonal Carcinomas, undifferentiated carcinomas of the rhino-pharynx (e.g., Schmincke's tumor), Castleman's disease, Kaposi's Sarcoma, Multiple Myeloma, Waldenstrom's macroglobulinemia, and other B-ell lymphomas.

Suitable routes of administering the antibody compositions (e.g., human monoclonal antibodies, multispecific and bispecific molecules and immunoconjugates) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-CD19 antibodies of the invention can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the human anti-CD19 antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Target-specific effector cells, e.g., effector cells linked to compositions (e.g., human antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$ but will vary depending on the therapeutic purpose. In general the amount will be sufficient to obtain localization at the target cell, e.g., a tumor cell expressing CD19, and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-CD19 antibodies linked to anti-Fc-gamma R1 or anti-CD3 may be used in conjunction with IgG- or IgA-receptor specific binding agents.

Bispecific and multispecific molecules of the invention can also be used to modulate FcγR or FcγR levels on effector cells, such as by capping and elimination of receptors on the cell surface. Mixtures of anti-Fc receptors can also be used for this purpose.

The compositions (e.g., human antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multispecific and bispecific molecules) of the invention can also be lysed by complement. In yet another embodiment, the compositions of the invention do not activate complement.

The compositions (e.g., human antibodies, multispecific and bispecific molecules and immunoconjugates) of the invention can also be administered together with complement. In certain embodiments, the instant disclosure provides compositions comprising human antibodies, multispecific or bispecific molecules and serum or complement. These compositions can be advantageous when the complement is located in close proximity to the human antibodies, multispecific or bispecific molecules. Alternatively, the human antibodies, multispecific or bispecific molecules of the invention and the complement or serum can be administered separately.

Also within the scope of the present invention are kits comprising the antibody compositions of the invention (e.g., human antibodies, bispecific or multispecific molecules, or immunoconjugates) and instructions for use. The kit can further contain one or more additional reagents, such as an immunosuppressive reagent, a cytotoxic agent or a radiotoxic agent, or one or more additional human antibodies of the invention (e.g., a human antibody having a complementary activity which binds to an epitope in the CD19 antigen distinct from the first human antibody).

Accordingly, patients treated with antibody compositions of the invention can be additionally administered (prior to, simultaneously with, or following administration of a human antibody of the invention) with another therapeutic agent, such as a cytotoxic or radiotoxic agent, which enhances or augments the therapeutic effect of the human antibodies.

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

The compositions (e.g., human antibodies, multispecific and bispecific molecules) of the invention can also be used to target cells expressing FcγR or CD19, for example for labeling such cells. For such use, the binding agent can be linked to a molecule that can be detected. Thus, the invention provides methods for localizing ex vivo or in vitro cells expressing Fc receptors, such as FcγR, or CD19. The detectable label can be, e.g., a radioisotope, a fluorescent compound, an enzyme, or an enzyme co-factor.

In a particular embodiment, the invention provides methods for detecting the presence of CD19 antigen in a sample, or measuring the amount of CD19 antigen, comprising contacting the sample, and a control sample, with a human monoclonal antibody, or an antigen binding portion thereof, which specifically binds to CD19, under conditions that allow for formation of a complex between the antibody or portion thereof and CD19. The formation of a complex is then detected, wherein a difference complex formation between the sample compared to the control sample is indicative the presence of CD19 antigen in the sample.

In other embodiments, the invention provides methods for treating an CD19 mediated disorder in a subject, e.g., autoimmune disorder, rheumatoid arthritis, cancer, non-Hodgkin's lymphoma, acute lymphocytic leukemia (ALL), chronic lymphocytic leukemia (CLL), Burkitt's lymphoma, anaplastic large-cell lymphomas (ALCL), cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), entroblastic/centrocytic (cb/cc) follicular lymphomas cancers, diffuse large cell lymphomas of B lineage, angioimmunoblastic lymphadenopathy (AILD)-like T cell lymphoma, HIV associated body cavity based lymphomas, Embryonal Carcinomas, undifferentiated carcinomas of the rhino-pharynx (e.g., Schmincke's tumor), Castleman's disease, Kaposi's Sarcoma, Multiple Myeloma, Waldenstrom's macroglobulinemia, and other B-cell lymphomas, by administering to the subject the human antibodies described above. Such antibodies and derivatives thereof are used to inhibit CD19 induced activities associated with certain disorders, e.g., proliferation and differentiation. By contacting the antibody with CD19

(e.g., by administering the antibody to a subject), the ability of CD19 to induce such activities is inhibited and, thus, the associated disorder is treated. The antibody composition can be administered alone or along with another therapeutic agent, such as a cytotoxic or a radiotoxic agent which acts in conjunction with or synergistically with the antibody composition to treat or prevent the CD19 mediated disease.

In yet another embodiment, immunoconjugates of the invention can be used to target compounds (e.g., therapeutic agents, labels, cytotoxins, radiotoxoins immunosuppressants, etc.) to cells which have CD19 cell surface receptors by linking such compounds to the antibody. For example, an anti-D19 antibody can be conjugated to any of the toxin compounds described in U.S. Pat. Nos. 6,281,354 and 6,548,530, US patent publication Nos. 20030050331, 20030064984, 20030073852, and 20040087497, or published in WO 03/022806. Thus, the invention also provides methods for localizing ex vivo or in vivo cells expressing CD19 (e.g., with a detectable label, such as a radioisotope, a fluorescent compound, an enzyme, or an enzyme co-factor). Alternatively, the immunoconjugates can be used to kill cells which have CD19 cell surface receptors by targeting cytotoxins or radiotoxins to CD19.

The present invention is further illustrated by the following examples which should not be construed as further limiting. The contents of all figures and all references, patents and published patent applications cited throughout this application are expressly incorporated herein by reference.

EXAMPLES

Example 1

Generation of Human Monoclonal Antibodies Against CD19

Antigen

The B cell tumor cell lines Raji (ATCC Accession #CCL-86) and Daudi (ATCC Accession #CCL-213) were used as antigen for immunization.
Transgenic Transchromosomic KM-MOUSE®

Fully human monoclonal antibodies to CD19 were prepared using the KM strain of transgenic transchromosomic mice, which expresses human antibody genes. In this mouse strain, the endogenous mouse kappa light chain gene has been homozygously disrupted as described in Chen et al. (1993) EMBO J. 12:811-820 and the endogenous mouse heavy chain gene has been homozygously disrupted as described in Example 1 of PCT Publication WO 01/09187 for HuMab mice. The mouse carries a human kappa light chain transgene, KCo5, as described in Fishwild et al. (1996) Nature Biotechnology 14:845-851. The mouse also carries a human heavy chain transchromosome, SC20, as described in PCT Publication WO 02/43478.
KM-MOUSE® Immunizations:

To generate fully human monoclonal antibodies to CD19, cohorts of the KM-MOUSE® were immunized with either the Raji or Daudi B cell tumor cell line. General immunization schemes are described in Lonberg, N. et al. (1994) *Nature* 368(6474): 856-859; Fishwild, D. et al. (1996) Nature Biotechnology 14: 845-851 and PCT Publication WO 98/24884. The mice were 6-16 weeks of age upon the first infusion of antigen. A cell preparation was used to immunize the mice (KM-MOUSE®) intraperitonealy (IP).

Transgenic mice were immunized twice with antigen in complete Freund's adjuvant or Ribi adjuvant IP, followed by 3-21 days IP (up to a total of 11 immunizations) with the antigen in incomplete Freund's or Ribi adjuvant. The immune response was monitored by retroorbital bleeds. The plasma was screened by ELISA (as described below), and mice with sufficient titers of anti-CD19 human immunoglobulin were used for fusions. Mice were boosted intravenously with antigen 3 days before sacrifice and removal of the spleen.
Selection of a KM-MOUSE® Producing Anti-CD19 Antibodies:

To select a KM-MOUSE® producing antibodies that bound CD19, sera from immunized mice were tested by a modified ELISA as originally described by Fishwild, D. et al. (1996), supra. Briefly, microtiter plates were coated with purified recombinant CD19 fusion protein at 1-2 µg/ml in PBS, 50 µl/wells incubated 4° C. overnight-then blocked with 200 µl/well of 5% BSA in PBS. Dilutions of plasma from CD19 immunized mice were added to each well and incubated for 1-2 hours at ambient temperature. The plates were washed with PBS/Tween and then incubated with a goat-anti-human kappa light chain polyclonal antibody conjugated with alkaline phophatase for 1 hour at room temperature. After washing, the plates were developed with pNPP substrate and analyzed by spectrophotometer at OD 415-650. Mice that developed the highest titers of anti-CD19 antibodies were used for fusions. Fusions were performed as described below and hybridoma supernatants were tested for anti-CD19 activity by ELISA.
Generation of Hybridomas Producing Human Monoclonal Antibodies to CD19:

The mouse splenocytes, isolated from a KM-MOUSE®, were fused with PEG to a mouse myeloma cell line either using PEG based upon standard protocols or electric field based electrofusion using a Cyto Pulse large chamber cull fusion electroporator (Cyto Pulse Sciences, Inc., Glen Burnie, Md.). The resulting hybridomas were then screened for the production of antigen-specific antibodies. Single cell suspensions of splenic lymphocytes from immunized mice were fused to one-fourth the number of SP2/0 nonsecreting mouse myeloma cells (ATCC, CRL-1581) with 50% PEG (Sigma). Cells were plated at approximately $1 \times 10^5$/well in flat bottom microtiter plate, followed by about two week incubation in selective medium containing 10% fetal bovine serum, 10% P388DI (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1×HAT (Sigma, CRL P-7185). After 1-2 weeks, cells were cultured in medium in which the HAT was replaced with HT. Individual wells were then screened by ELISA (described above) for human anti-CD19 monoclonal IgG antibodies. Once extensive hybridoma growth occurred, medium was monitored usually after 10-14 days. The antibody secreting hybridomas were replated, screened again and, if still positive for human IgG, anti-CD19 monoclonal antibodies were subcloned at least twice by limiting dilution. The stable subclones were then cultured in vitro to generate small amounts of antibody in tissue culture medium for further characterization.

Hybridoma clones 21D4, 21D4a, 47G4, 27F3, 3C10, 5G7, 13F1 and 46E8 were selected for further analysis.

Example 2

Structural Characterization of Human Monoclonal Antibodies 21D4, 21D4a, 47G4, 27F3, 3C10, 5G7, 13F1 and 46E8

The cDNA sequences encoding the heavy and light chain variable regions of the 21D4 and 21D4a monoclonal antibodies were obtained from the 21D4 hybridoma using standard PCR techniques and were sequenced using standard DNA sequencing techniques. It is noted that the 21D4 hybridoma produces antibodies having a heavy chain that pairs with one of two light chains (SEQ ID NOs: 8 and 9). Both antibodies (i.e., 21D4 with $V_H$ and $V_L$ sequences of SEQ ID NOs: 1 and 8, respectively, and 21D4a with $V_H$ and $V_L$ sequences of SEQ ID NOs: 1 and 9, respectively) bind to CD19. The cDNA sequences encoding the heavy and light chain variable regions of the 47G4, 27F3, 3C10, 5G7, 13F1 and 46E8 monoclonal antibodies were obtained from the 21D4, 21D4a, 47G4, 27F3, 3C10, 5G7, 13F1 and 46E8 hybridomas, respectively, using standard PCR techniques and were sequenced using standard DNA sequencing techniques.

The nucleotide and amino acid sequences of the heavy chain variable region of 21D4 are shown in FIG. 1A and in SEQ ID NO: 59 and 1, respectively.

The nucleotide and amino acid sequences of the light chain variable region of 21D4 are shown in FIG. 1B and in SEQ ID NO: 66 and 8, respectively.

Comparison of the 21D4 heavy chain immunoglobulin sequence to the known human germline immunoglobulin heavy chain sequences demonstrated that the 21D4 heavy chain utilizes a $V_H$ segment from human germline $V_H$ 5-51, a D segment from the human germline 3-10, and a $J_H$ segment from human germline $J_H$ 4b. The alignment of the 21D4 $V_H$ sequence to the germline $V_H$ 5-51 sequence is shown in FIG. 8. Further analysis of the 21D4 $V_H$ sequence using the Kabat system of CDR region determination led to the delineation of the heavy chain CDR1, CDR2 and CD3 regions as shown in FIGS. 1A and 8, and in SEQ ID NOs: 16, 23 and 30, respectively.

Comparison of the 21D4 light chain immunoglobulin sequence to the known human germline immunoglobulin light chain sequences demonstrated that the 21D4 light chain utilizes a $V_L$ segment from human germline $V_K$ L18 and a $J_K$ segment from human germline JK 2. The alignment of the 21D4 $V_L$ sequence to the germline $V_K$ L18 sequence is shown in FIG. 15. Further analysis of the 21D4 $V_L$ sequence using the Kabat system of CDR region determination led to the delineation of the light chain CDR1CDR2 and CD3 regions as shown in FIGS. 1B and 15, and in SEQ ID NOs: 37, 44 and 51, respectively.

The nucleotide and amino acid sequences of the heavy chain variable region of 21D4a are shown in FIG. 1A and in SEQ ID NO: 59 and 1, respectively.

The nucleotide and amino acid sequences of the light chain variable region of 21D4a are shown in FIG. 1C and in SEQ ID NO: 67 and 9, respectively.

Comparison of the 21D4a heavy chain immunoglobulin sequence to the known human germline immunoglobulin heavy chain sequences demonstrated that the 21D4a heavy chain utilizes a $V_H$ segment from human germline $V_H$ 5-51, a D segment from the human germline 3-10, and a $J_H$ segment from human germline $J_H$ 4b. The alignment of the 21D4a $V_H$ sequence to the germline $V_H$ 5-51 sequence is shown in FIG. 8. Further analysis of the 21D4a $V_H$ sequence using the Kabat system of CDR region determination led to the delineation of the heavy chain CDR1, CDR1 and CD3 regions as shown in FIGS. 1A and 8, and in SEQ ID NOs: 16, 23 and 30, respectively.

Comparison of the 21D4a light chain immunoglobulin sequence to the known human germline immunoglobulin light chain sequences demonstrated that the 21D4a light chain utilizes a $V_L$ segment from human germline $V_K$ L18 and a $J_K$ segment from human germline JK 3. The alignment of the 21D4a $V_L$ sequence to the germline $V_K$ L18 sequence is shown in FIG. 16. Further analysis of the 21D4a $V_L$ sequence using the Kabat system of CDR region determination led to the delineation of the light chain CDR1, CDR2 and CD3 regions as shown in FIGS. 1C and 16, and in SEQ ID NOs: 37, 44 and 52, respectively.

The nucleotide and amino acid sequences of the heavy chain variable region of 47G4 are shown in FIG. 2A and in SEQ ID NO: 60 and 2, respectively.

The nucleotide and amino acid sequences of the light chain variable region of 47G4 are shown in FIG. 2B and in SEQ ID NO: 68 and 10, respectively.

Comparison of the 47G4 heavy chain immunoglobulin sequence to the known human germline immunoglobulin heavy chain sequences demonstrated that the 47G4 heavy chain utilizes a $V_H$ segment from human germline $V_H$ 1-69, a D segment from the human germline 6-19, and a $J_H$ segment from human germline $J_H$ 5b. The alignment of the 47G4 $V_H$ sequence to the germline $V_H$ 1-69 sequence is shown in FIG. 9. Further analysis of the 47G4 $V_H$ sequence using the Kabat system of CDR region determination led to the delineation of the heavy chain CDR1, CDR2 and CD3 regions as shown in FIGS. 2A and 9, and in SEQ ID NOs: 17, 24 and 31, respectively.

Comparison of the 47G4 light chain immunoglobulin sequence to the known human germline immunoglobulin light chain sequences demonstrated that the 47G4 light chain utilizes a $V_L$ segment from human germline $V_K$ A27 and a JK segment from human germline JK 3. The alignment of the 47G4 $V_L$ sequence to the germline $V_K$ A27 sequence is shown in FIG. 17. Further analysis of the 4704 $V_L$ sequence using the Kabat system of CDR region determination led to the delineation of the light chain CDR1, CDR2 and CD3 regions as shown in FIGS. 2B and 17, and in SEQ ID NOs: 38, 45 and 53, respectively.

The nucleotide and amino acid sequences of the heavy chain variable region of 27F3 are shown in FIG. 3A and in SEQ ID NO: 61 and 3, respectively.

The nucleotide and amino acid sequences of the light chain variable region of 27F3 are shown in FIG. 3B and in SEQ ID NO: 69 and 11, respectively.

Comparison of the 27F3 heavy chain immunoglobulin sequence to the known human germline immunoglobulin heavy chain sequences demonstrated that the 27F3 heavy chain utilizes a $V_H$ segment from human germline $V_H$ 5-51, a D segment from the human germline 6-19, and a $J_H$ segment from human germline $J_H$ 6b. The alignment of the 27F3 $V_H$ sequence to the germline $V_H$ 5-51 sequence is shown in FIG. 10. Further analysis of the 27F3 $V_H$ sequence using the Kabat system of CDR region determination led to the delineation of the heavy chain CDR1, CDR2 and CD3 regions as shown in FIGS. 3A and 10, and in SEQ ID NOs: 18, 25 and 32, respectively.

Comparison of the 27F3 light chain immunoglobulin sequence to the known human germline immunoglobulin light chain sequences demonstrated that the 27F3 light chain utilizes a $V_L$ segment from human germline $V_K$ L18 and a JK segment from human germline JK 2. The alignment of the 27F3 $V_L$ sequence to the germline $V_K$ L18 sequence is shown in FIG. 18. Further analysis of the 27F3 $V_L$ sequence using the Kabat system of CDR region determination led to the delineation of the light chain CDR1, CDR2 and CD3 regions as shown in FIGS. 3B and 18, and in SEQ ID NOs: 39, 46 and 54, respectively.

The nucleotide and amino acid sequences of the heavy chain variable region of 3C10 are shown in FIG. 4A and in SEQ ID NO: 62 and 4, respectively.

The nucleotide and amino acid sequences of the light chain variable region of 3C10 are shown in FIG. 4B and in SEQ ID NO: 70 and 12, respectively.

Comparison of the 3C10 heavy chain immunoglobulin sequence to the known human germline immunoglobulin heavy chain sequences demonstrated that the 3C10 heavy chain utilizes a $V_H$ segment from human germline $V_H$ 1-69, a D segment from the human germline 1-26, and a $J_H$ segment from human germline $J_H$ 6b. The alignment of the 3C10 $V_H$ sequence to the germline $V_H$ 1-69 sequence is shown in FIG. 11. Further analysis of the 3C10 $V_H$ sequence using the Kabat system of CDR region determination led to the delineation of the heavy chain CDR1, CDR2 and CD3 regions as shown in FIGS. 4A and 11, and in SEQ ID NOs: 19, 26 and 33, respectively.

Comparison of the 3C10 light chain immunoglobulin sequence to the known human germline immunoglobulin light chain sequences demonstrated that the 3C10 light chain utilizes a $V_L$ segment from human germline $V_K$ L15 and a JK segment from human germline $J_K$ 2. The alignment of the 3C10 $V_L$ sequence to the germline $V_K$ L15 sequence is shown in FIG. 19. Further analysis of the 3C10 $V_L$ sequence using the Kabat system of CDR region determination led to the delineation of the light chain CDR1, CDR2 and CD3 regions as shown in FIGS. 4B and 19, and in SEQ ID NOs: 40, 47 and 55, respectively.

The nucleotide and amino acid sequences of the heavy chain variable region of 5G7 are shown in FIG. 5A and in SEQ ID NO: 63 and 5, respectively.

The nucleotide and amino acid sequences of the light chain variable region of 5G7 are shown in FIG. 5B and in SEQ ID NO: 71 and 13, respectively.

Comparison of the 5G7 heavy chain immunoglobulin sequence to the known human germline immunoglobulin heavy chain sequences demonstrated that the 5G7 heavy chain utilizes a $V_H$ segment from human germline $V_H$ 5-51, a D segment from the human germline 3-10, and a $J_H$ segment from human germline JH 6b. The alignment of the 5G7 $V_H$ sequence to the germline $V_H$ 5-51 sequence is shown in FIG. 12. Further analysis of the 5G7 $V_H$ sequence using the Kabat system of CDR region determination led to the delineation of the heavy chain CDR1, CDR2 and CD3 regions as shown in FIGS. 5A and 12, and in SEQ ID NOs: 20, 27 and 34, respectively.

Comparison of the 5G7 light chain immunoglobulin sequence to the known human germline immunoglobulin light chain sequences demonstrated that the 5G7 light chain utilizes a $V_L$ segment from human germline $V_K$ L18 and a $J_K$ segment from human germline JK 1. The alignment of the 5G7 $V_L$ sequence to the germline $V_K$ L18 sequence is shown in FIG. 20. Further analysis of the 5G7 $V_L$ sequence using the Kabat system of CDR region determination led to the delineation of the light chain CDR1, CDR2 and CD3 regions as shown in FIGS. 5B and 20, and in SEQ ID NOs: 41, 48 and 56, respectively.

The nucleotide and amino acid sequences of the heavy chain variable region of 13F1 are shown in FIG. 6A and in SEQ ID NO: 64 and 6, respectively.

The nucleotide and amino acid sequences of the light chain variable region of 13F1 are shown in FIG. 6B and in SEQ ID NO: 72 and 14, respectively.

Comparison of the 13F1 heavy chain immunoglobulin sequence to the known human germline immunoglobulin heavy chain sequences demonstrated that the 13F1 heavy chain utilizes a $V_H$ segment from human germline $V_H$ 5-51, a D segment from the human germline 6-19, and a $J_H$ segment from human germline JH 6b. The alignment of the 13F1 $V_H$ sequence to the germline $V_H$ 5-51 sequence is shown in FIG. 13. Further analysis of the 13F1 $V_H$ sequence using the Kabat system of CDR region determination led to the delineation of the heavy chain CDR1, CDR2 and CD3 regions as shown in FIGS. 6A and 13, and in SEQ ID NOs: 21, 28 and 35, respectively.

Comparison of the 13F1 light chain immunoglobulin sequence to the known human germline immunoglobulin light chain sequences demonstrated that the 13F1 light chain utilizes a $V_L$ segment from human germline $V_K$ L18 and a JK segment from human germline JK 2. The alignment of the 13F1 $V_L$ sequence to the germline $V_K$ L18 sequence is shown in FIG. 21. Further analysis of the 13F1 $V_L$ sequence using the Kabat system of CDR region determination led to the delineation of the light chain CDR1, CDR2 and CD3 regions as shown in FIGS. 6B and 21, and in SEQ ID NOs: 42, 49 and 57, respectively.

The nucleotide and amino acid sequences of the heavy chain variable region of 46E8 are shown in FIG. 7A and in SEQ ID NO: 65 and 7, respectively.

The nucleotide and amino acid sequences of the light chain variable region of 46E8 are shown in FIG. 7B and in SEQ ID NO: 73 and 15, respectively.

Comparison of the 46E8 heavy chain immunoglobulin sequence to the known human germline immunoglobulin heavy chain sequences demonstrated that the 46E8 heavy chain utilizes a $V_H$ segment from human germline $V_H$ 5-51, a D segment from the human germline 6-19, and a $J_H$ segment from human germline JH 6b. The alignment of the 46E8 $V_H$ sequence to the germline $V_H$ 5-51 sequence is shown in FIG. 14. Further analysis of the 46E8 $V_H$ sequence using the Kabat system of CDR region determination led to the delineation of the heavy chain CDR1, CDR2 and CD3 regions as shown in FIGS. 7A and 14, and in SEQ ID NOs: 22, 29 and 36, respectively.

Comparison of the 46E8 light chain immunoglobulin sequence to the known human germline immunoglobulin light chain sequences demonstrated that the 46E8 light chain utilizes a $V_L$ segment from human germline $V_K$ L18 and a $J_K$ segment from human germline JK 2. The alignment of the 46E8 $V_L$ sequence to the germline $V_K$ L18 sequence is shown in FIG. 22. Further analysis of the 46E8 $V_L$ sequence using the Kabat system of CDR region determination led to the delineation of the light chain CDR1, CDR2 and CD3 regions as shown in FIGS. 7B and 22, and in SEQ ID NOs: 43, 50 and 58, respectively.

Example 3

Characterization of Binding Specificity and Binding Kinetics of Anti-CD19 Human Monoclonal Antibodies In this example, the binding affinity of the anti-CD19 antibodies 21D4 and 47G4 were examined by ELISA analysis.
Binding Specificity by ELISA Microtiter plates were coated with 50 µl purified full-length CD19-Fc fusion protein at 1.0 µg/ml in PBS, and then blocked with 150 µl of 1% bovine serum albumin in PBS. The plates were allowed to incubate for 30 minutes to 1 hour and washed three times. Dilutions of the HuMAb anti-CD19 antibody 47G4 was added to each well and incubated for 1 hour at 37° C. A known murine anti-CD19 antibody was used as a positive control. The plates were washed with PBS/Tween and then incubated with a goat anti-human IgG Kappa-specific secondary reagent conjugated to horseradish peroxidase for 1 hour at 37° C. After washing, the plates were developed with ABTS substrate (1.46 mMol/L), and analyzed at OD of 490 nm. The results are depicted in FIG. 23. The CD19 HuMAb 47G4 specifically bound to the human CD19 peptide.

Epitope Mapping of Anti-CD19 Antibodies

Flow cytometry was used to determine epitope grouping of anti-CD19 HuMAbs. Epitope binding of the anti-CD19 human monoclonal antibodies 21D4, 21D4a, 3C10, 5G7, 507-N19K, 5G7-N19Q and 13F1 was assessed by incubating Raji B tumor cells with 0.3 µg/ml of either biotinylated 21D4 or 21D4a anti-CD19 human monoclonal antibody, washed, and followed by the addition of a cold anti-CD19 human monoclonal antibody. An isotype control antibody was used as a negative control. Binding was detected with a FITC-labeled anti-human IgG Ab. Flow cytometric analyses were performed using a FACScan flow cytometry (Becton Dickinson, San Jose, Calif.). The results are shown in FIG. 24. Upon analysis of the data, the anti-CD19 antibodies 21D4, 21D4a, 3C10, 5G7 and 13F1 compete for the same epitope region.

Example 4

Binding of the CD19 Antibodies to a B cell-Derived Tumor Cell Line

Binding of the CD19 HuMAbs by flow cytometry to the B cell tumor lines Raji and Daudi, or to a CHO-CD19 transfected cell line was assessed. CHO cells were transfected with an expression plasmid containing the full length cDNA encoding the transmembrane form of CD19. The Raji, Daudi, and CD19-CHO cell lines were incubated with one of the following CD19 HuMAbs: 21D4, 21D4a, 47G4, 5G7, 5G7-N19K, 5G7-N19Q, 3C10 or 13F1. A known murine anti-CD19 antibody was used as a positive control. The cells were washed and detected by either a phycoerythrin-labeled anti-human or anti-mouse secondary antibody and analyzed by flow cytometry. The results for binding to the CHO-CD19 cell line, Daudi B cell line, Raji B cell line and an expanded binding set against the Raji B cell line are shown in FIGS. 25A, 25B, 25C and 25D, respectively. The human anti-CD19 monoclonal antibodies, 21D4 and 47G4, bound to the CHO-CD19 cell line. The human anti-CD19 monoclonal antibodies, 21D4, 21D4a, 47G4, 5G7, 5G7-N19K, 5G7-N19Q, 3C10 and 13F1, bound to the Raji B cell line. The anti-CD19 HuMAb antibodies 21D4, 21D4a, 3C10, 5G7, 5G7-N19K, 5G7-N19Q, and 13F1 had calculated $EC_{50}$ values of 0.1413, 0.1293, 0.2399, 0.1878, 0.2240, 0.2167 and 0.2659, respectively. 47G4 was also shown to bind the Daudi B tumor cell line. All results are shown as measured by the geometric mean fluorescent intensity (GMFI) of staining. These data show that the CD19 protein is expressed on the surface of tumor cell lines of B cell origin and that the anti-CD19 HuMAb antibodies 21D4, 21D4a, 47G4, 5G7, 5G7-N 9K, 5G7-N19Q, 3C10 and 13F1 bind to CD19 expressed on the cell surface.

Example 5

Scatchard Binding Analysis of the Anti-CD19 Human Antibodies 21D4 and 47G4 to Raji B Tumor Cells Raji cells were obtained from ATCC (Accession #CCL-86) and grown in RPMI containing 10% fetal bovine serum (FBS). The cells were washed twice with RPMI containing 10% FBS at 4° C. and the cells were adjusted to $4\times10^7$ cells/ml in RPMI media containing 10% fetal bovine serum (binding buffer containing 24 mM Tris pH 7.2, 137 mM NaCl, 2.7mN KCl, 2 mM glucose, 1 mM $CaCl_2$, 1 mM $MgCl_2$, 0.1% BSA). Millipore plates (MAFB NOB) were coated with 1% nonfat dry milk in water and stored a 4° C. overnight. The plates were washed with binding buffer and 25 µl of unlabeled antibody (1000-fold excess) in binding buffer was added to control wells in a Millipore 96 well glass fiber filter plate (non-specific binding NSB). Twenty-five microliters of buffer alone was added to the maximum binding control well (total binding). Twenty-five microliters of varying concentrations of $^{125}$I-anti-CD19 antibody 21D4 or 47G4 and 25 µl of Raji cells ($4\times10^7$ cells/ml) in binding buffer were added. The plates were incubated for 2 hours at 200 RPM on a shaker at 4° C. At the completion of the incubation the Millipore plates were washed three times with 0.2 ml of cold wash buffer (24 mM Tris pH 7.2, 500 mM NaCl, 2.7mN KCl, 2 mM glucose, 1 mM $CaCl_2$, 1 mM $MgCl_2$, 0.1% BSA). The filters were removed and counted in a gamma counter. Evaluation of equilibrium binding was performed using single site binding parameters with the Prism software (San Diego, Calif.). Using the above scatchard binding assay, the $K_D$ of the antibody for Raji cells was approximately 2.14 nM for 21D4 and 12.02 nM for 47G4.

Example 6

Internalization of Anti-CD19 Monoclonal Antibody

Anti-CD19 HuMAbs were tested for the ability to internalize into CD19-expressing Raji B tumor cells or human CHO cells transfected with CD19 using a Hum-Zap internalization assay. Hum-Zap tests for internalization of a primary human antibody through binding of a secondary antibody with affinity for human IgG conjugated to the toxin saporin.

The CHO-CD19 or Raji B tumor cell line was seeded at $1.0\times10^4$ cells/well in 100 µl wells either overnight or the following day for a two hour period. Either the anti-CD19 antibody 21D4 or 47G4 were added to the wells at a starting concentration of 30 µM and titrated down at 1:3 serial dilutions. A human isotype control antibody that is non-specific for CD19 was used as a negative control. The Hum-Zap (Advanced Targeting Systems, IT-22-25) was added at a concentration of 11 nM and plates were allowed to incubate for 48 hours. The plates were then pulsed with 1.0 HCl of $^3$H-thymidine for 18-24 hours, harvested and read in a Top Count Scintillation Counter (Packard Instruments). The results for internalization on CHO-CD19 and B tumor cells are shown in FIGS. 26A and 26B, respectively. Only the HuMAb 47G4 was tested on CHO-CD19 cells. The anti-CD19 antibody 47G4 showed an antibody concentration dependent decrease in $^3$H-thymidine incorporation on CHO-CD19 cells. Both the 21D4 and 47G4 HuMAbs showed an antibody concentration dependent decrease in $^3$H-thymidine incorporation on Raji B tumor cells. This data demonstrates that the anti-CD19 antibodies 21D4 and 47G4 internalize into CD19 expressing CHO-CD19 transfectant cells and B tumor cells.

Example 7

Assessment of Cell Killing of a Toxin-Conjugated Anti-CD19 Antibody

In this example, anti-CD19 monoclonal antibodies conjugated to a toxin were tested for the ability to kill CD19+ cell lines in a thymidine incorporation assay.

An anti-CD19 monoclonal antibody was conjugated to a toxin via a linker, such as a peptidyl, hydrazone or disulfide linker. The CD19+ expressing Raji cell line was seeded at 2.5×10⁴ cells/wells for 3 hours. An anti-CD19 antibody-toxin conjugate was added to the wells at a starting concentration of 30 nM and titrated down at 1:3 serial dilutions. An isotype control antibody that is non-specific for CD19 was used as a negative control. Ten-fold excess cold antibody, either 21D4a or an isotype control antibody is used to compete binding. Plates were allowed to incubate for 69 hours. The plates were then pulsed with 1.0 µCi of ³H-thymidine for 24 hours, harvested and read in a Top Count Scintillation Counter (Packard Instruments, Meriden, Conn.). The results are shown in FIG. 27 along with the EC50 values. This data demonstrates that the anti-CD19 antibody 21D4 kills Raji B-cell tumor cells.

Example 8

Treatment of In Vivo B Cell Tumors Using Anti-CD19 Antibodies

In this Example, SCID mice implanted with cancerous B cell tumors were treated in vivo with either naked anti-CD19 antibodies or toxin-conjugated anti-CD19 antibodies to examine the in vivo effect of the antibodies on tumor growth.

Toxin-conjugated anti-CD19 antibodies were prepared as described above. Severe combined immune deficient (SCID) mice, which lack functional B and T lymphocytes were used to study B-cell malignancies. Cells from the Ramos B tumor cell line were injected intravenously. The mice were treated either with 19.6 mg/kg of toxin-conjugate anti-CD19 antibody or 30 mg/kg naked anti-CD19 antibody. An isotype control antibody or formulation buffer was used as a negative control. The animals were dosed by intraperitoneal injection with approximately 200 µl of PBS containing antibody or vehicle. The antibody-toxin conjugate was injected as a single dose on day 7, while the naked antibody was either injected as a single dose prophylactic model on day 1 or as a treatment model on days 7, 14 and 21. The mice were monitored daily for hind leg paralysis for approximately 6 weeks. Using an electronic caliper, the tumors were measured three dimensionally (height×width×length) and tumor volume was calculated. Mice were euthanized when there was hindleg paralysis.

As documented by Kaplan-Meier analysis (FIG. 28), there was an increase in mean survival time upon treatment with toxin-conjugated anti-CD19 antibodies, naked anti-CD19 antibodies administered prophylactically or anti-CD19 antibodies administered as a treatment regimen. The largest increase in mean survival time shown was by prophylactic treatment using the naked anti-CD19 antibody.

The change in body weight was also measured and calculated as percent change in weight. The data is shown in FIG. 29. Over a 30 day period, there was a net increase change in body weight with one toxin-conjugate antibody and a net decrease change in body weight with antibody and toxin (not conjugate). There was a net increase change in body weight with either the prophylactic naked anti-CD19 antibody or the anti-CD19 antibody treatment regimen.

Example 9

Treatment of In Vivo Tumor Xenograft Model Using Naked Anti-CD19 Antibodies

Mice implanted with a lymphoma tumor were treated in vivo with naked anti-CD19 antibodies to examine the in vivo effect of the antibodies on tumor growth.

ARH-77 (human B lymphoblast leukemia; ATCC Accession No. CRL-1621) and Raji (human B lymphocyte Burkitt's lymphoma; ATCC Accession No. CCL-86) cells were expanded in vitro using standard laboratory procedures. Male CB17.SCID mice (Taconic, Hudson, N.Y.) between 6-8 weeks of age were implanted subcutaneously in the right flank with 5×10⁶ ARH-77 or Raji cells in 0.2 ml of PBS/Matrigel (1:1) per mouse. Mice were weighed and measured for tumors three dimensionally using an electronic caliper twice weekly after implantation. Tumor volumes were calculated as height×width×length/2. Mice with ARH-77 tumors averaging 80 mm³ or Raji tumors averaging 170 mm³ were randomized into treatment groups. The mice were dosed intraperitoneally with PBS vehicle, isotype control antibody or naked anti-CD19 HuMAb 2H5 on Day 0. Mice were euthanized when the tumors reached tumor end point (2000 mm³). The results are shown in FIG. 30A (ARH-77 tumors) and 30B (Raji tumors). The naked anti-CD19 antibody 21D4 extended the mean time to reaching the tumor end point volume (2000 mm³) and slowed tumor growth progression. Thus, treatment with an anti-CD19 antibody alone has a direct in vivo inhibitory effect on tumor growth.

Example 10

Production of Nonfucosylated HuMAbs

Antibodies with reduced amounts of fucosyl residues have been demonstrated to increase the ADCC ability of the antibody. In this example, the anti-CD19 HuMAb 21D4 has been produced that is lacking in fucosyl residues.

The CHO cell line Ms704-PF, which lacks the fucosyltransferase gene, FUT 8 (Biowa, Inc., Princeton, N.J.) was electroporated with a vector which expresses the heavy and light chains of antibody 21D4. Drug-resistant clones were selected by growth in Ex-Cell 325-PF CHO media (JRH Biosciences, Lenexa, Kans.) with 6 mM L-glutamine and 500 µg/ml G418 (Invitrogen, Carlsbad, Calif.). Clones were screened for IgG expression by standard ELISA assay.

Oligosaccharide Characterization of MAbs by CE-LIF

Comparative analysis of N-linked oligosaccharides derived from anti-CD19 antibodies from a CHO fucosylating cell line and the Ms704-PF derived anti-CD19 monoclonal antibody samples was done by capillary electrophoresis laser induced fluorescence (cLIF) (Chen and Evangelista (1998) Electrophoresis 15:1892). The N-linked oligosaccharides of the purified antibody were released from IgG samples (100 µg) by overnight incubation of the samples with 12.5 mU PNGaseF (Prozyme) at 40° C. Under the conditions used, the N-linked glycans from the Fc portion of HuMAb 21D4 expressed in CHO fucosylating and non-fucosylating cells were released. Following ethanol precipitation to remove MAb protein, the supernatant containing the glycans was dried by vacuum centrifugation and resuspended in 19 mM 8-aminopyrene-1,3,6-trisulfonate (APTS) (Beckman) under mild reductive amination conditions in which desialylation and loss of fucose residues was minimized (15% acetic acid and 1 M sodium cyanoborohydride in THF (Sigma)). The glycan labeling reaction was allowed to continue overnight at 40° C. followed by 25-fold dilution of sample in water. APTS-labeled glycans were applied to capillary electrophoresis with laser induced fluorescence on a P/ACE MDQ CE system (Beckman) with reverse polarity, using a 50 µm internal diameter N—CHO coated capillary (Beckman) with 50 cm effective length. Samples were pressure (8 sec.) injected and separation was carried out at 20° C. using Carbohydrate Separation Gel Buffer (Beckman) at 25 kV for 20 min. The separations were monitored using a laser-induced fluorescence detection system (Beckman) with a 3 mW argon ion laser and excitation wavelength of 488 nm and emission of 520 nm. (Ma and Nashabeh (1999) Anal. Chem. 71:5185). Differences in the oligosaccharide profile were observed between the antibody obtained from the fucosylating cell line as compared to the Ms704-PF cell line, consistent with an absence of fucose residues in the Ms704-PF derived anti-CD19 antibodies.

Monosaccharide analysis by HPLC with HPAE-PAD

IgG samples (200 µg) were subjected to acid hydrolysis using either 2 N TFA (for estimating neutral sugars) or 6 N HCl (for estimating amino sugars) at 100° C. for 4 h. Samples were dried by vacuum centrifugation at ambient temperature and were reconstituted in 200 µl water prior to analysis by HPAE-PAD (Dionex). Monosaccharides were separated using a CarboPac PA10 4×250 mm column with pre-column Amino Trap and Borate Trap (Dionex). Procedures were followed according to Dionex Technical Note 53. Monosaccharide peak identity and relative abundance were determined using monosaccharide standards (Dionex).

The nonfucosylated anti-CD19 21D4 antibody was also tested using a standard capillary isoelectric focusing kit assay (Beckman Coulter). The assay returned observed pI values of pH 8.45 for fucosylated 21D4, 8.44 and 8.21 for fucosylated 21D4a, and 8.52 and 8.30 for the nonfucosylated 21D4 antibodies.

Example 11

Assessment of ADCC Activity of Anti-CD19 Antibody

In this example, fucosylated and nonfucosylated anti-CD19 monoclonal antibodies were tested for the ability to kill CD19+ cells in the presence of effector cells via antibody dependent cellular cytotoxicity (ADCC) in a fluorescence cytotoxicity assay.

Nonfucosylated human Anti-CD19 monoclonal antibody 21D4 was prepared as described above. Human effector cells were prepared from whole blood as follows. Human peripheral blood mononuclear cells were purified from heparinized whole blood by standard Ficoll-paque separation. The cells were resuspended in RPMI1640 media containing 10% FBS (culture media) and 200 U/ml of human IL-2 and incubated overnight at 37° C. The following day, the cells were collected and washed once in culture media and resuspended at $2 \times 10^7$ cells/ml. Target CD19+ cells were incubated with BATDA reagent (Perkin Elmer, Wellesley, Mass.) at 2.5 µl BATDA per $1 \times 10^6$ target cells/mL in culture media supplemented with 2.5 mM probenecid (assay media) for 20 minutes at 37° C. The target cells were washed four times in PBS with 20 mM HEPES and 2.5 mM probenecid, spun down and brought to a final volume of $1 \times 10^5$ cells/ml in assay media.

The CD19+ cell line ARH-77 (human B lymphoblast leukemia; ATCC Accession No. CRL-1621) was tested for antibody specific ADCC to the fucosylated and non-fucosylated human anti-CD19 monoclonal antibody 21D4 using the Delfia fluorescence emission analysis as follows. The target cell line ARH77 (100 µl of labeled target cells) was incubated with 50 µl of effector cells and 50 µl of either 21D4 or nonfucosylated 21D4 antibody. A target to effector ratio of 1:50 was used throughout the experiments. A human IgG1 isotype control was used as a negative control. Following a 2100 rpm pulse spin and one hour incubation at 37° C., the supernatants were collected, quick spun again and 20 µl of supernatant was transferred to a flat bottom plate, to which 180 µl of Eu solution (Perkin Elmer, Wellesley, Mass.) was added and read in a Fusion Alpha TRF plate reader (Perkin Elmer). The % lysis was calculated as follows: (sample release−spontaneous release*100)/(maximum release−spontaneous release), where the spontaneous release is the fluorescence from wells which only contain target cells and maximum release is the fluorescence from wells containing target cells and have been treated with 3% Lysol. Cell cytotoxicity % specific lysis for the ARH-77 cell line is shown in FIG. 31. The CD19+ expressing cell line ARH-77 showed antibody mediated cytotoxicity with the HuMAb anti-CD19 antibody 21D4 and an increased percentage of specific lysis associated with the nonfucosylated form of the anti-CD19+ antibody 21D4. This data demonstrates that nonfucosylated HuMAb anti-CD19 antibodies show increased specific cytotoxicity to CD19+ expressing cells.

Example 12

Thermostability of Anti-CD19 Monoclonal Antibodies by Differential Scanning Calorimetry The thermal stability of the anti-CD19 monoclonal antibodies were compared using calorimetric analysis of their melting temperatures.

Calorimetric measurements of melting Temperatures™ were carried out on a VP-Capillary DSC differential scanning microcalorimeter platform that is combined with an autosampler (MicroCal LLC, Northampton, Mass., USA). Sample cell volume is 0.144 mL. Denaturation data on the glycosylated and deglycosylated forms of the antibodies was obtained by heating the samples, at a concentration of 2.3 µM, from 30 to 95° C. at a rate of 1° C./min. The protein samples were present in phosphate-buffered saline (PBS) at pH 7.4. The same buffer was used in the reference cell to obtain the molar heat capacity by comparison. The observed thermograms were baseline corrected and normalized data analyzed based on a 2-state model, using the software Origin v7.0. The data is shown in Table 2.

TABLE 2

Thermal stability measurement of anti-CD19 antibodies

| Clone | Thermo Stability $T_m1$ (° C.) |
|---|---|
| 21D4 | 68.7 |
| 21D4a | 69.7 |
| 5G7 | 68.5 |
| 5G7 IgG4 | 67.4 |
| 13F1 IgG4 | 68.4 |
| 46E8 | 66.4 |
| 47G4 | 67.2 |

Example 13

Assessment of Glycosylation Sites

The HuMAb anti-CD19 antibody 5G7 was found to have an N-X-S/T glycosylation motif in the variable region by sequence analysis. The presence of an N-linked sequence site (N-X-S/T) is necessary but not sufficient for addition of carbohydrate to MAb. That is, it is possible to have an N-X-S/T sequence that does not actually add a carbohydrate due protein folding and solvent accessibility. Confirmation of a glycosylation site in the variable region of 5G7 was examined by both LC-MS and Western analysis.

Liquid Chromatography-Mass Spectrometry (LC-MS) is a standard tool for determining the mass of a protein, such as an antibody. Prior to analysis, the N-linked oligosaccharides of the anti-CD19 HuMAbs 5G7 and 13F1 were released from IgG samples (100 μg) by overnight incubation of the samples with 12.5 mU PNGaseF (Prozyme) at 40° C. Under the conditions used, the N-linked glycans from the Fc portion of the HuMAbs were released. For clone 5G7, we observed two masses in high abundance; one (49,855 Da) corresponded to the predicted mass after PNGaseF digest to remove sugars in the constant region at the conserved N-linked site (N297), and a second mass (52,093 Da) consistent with addition of carbohydrate at a $2^{nd}$ site. We have found that Fab-region glycans are not removed by PNGaseF digestion; therefore, this data supports the presence of carbohydrates in the variable region of clone 5G7. For clone 13F1, the observed mass matched the predicted mass of the protein sequence without carbohydrates attached.

To confirm the above result, we completed a Western Blot assay on Fab fragments of clones 5G7 and 13F1, with a carbohydrate-specific staining method. Fab and Fc fragments were produced by adding 1.25 μg of activated papain to 25 μg of IgG samples containing 1 mM cysteine. Samples were incubated at 40° C. for 4 h and the reactions stopped with 30 mM iodoacetamide. Samples were analyzed by 4-20% Tris-Glycine SDS-PAGE followed by electro-blotting onto PVDF membrane. The carbohydrate specific staining of the blot was carried out using the Gel Code Glycoprotein Staining Kit (Pierce) following the protocol suggested by the manufacturer. The results detected Fab glycosylation in the 5G7 antibody, but not in the 13F1 antibody. These results showed that the 5G7 antibody is glycosylated in the Fab region.

As discussed above, the anti-CD19 monoclonal antibody 5G7 contains a variable region having a glycosylation site. Since glycosylation sites in the variable region may lead to increased immunogenicity of the antibody or altered pK values due to altered antigen binding, it may be advantageous to mutate the variable region N-X-S/T glycosylation motif sequence to reduce glycosylation. Using standard molecular biology techniques, the 5G7 antibody sequence was modified to change the N-I-S sequence starting at position 19 to either K-I-S (5G7-N19K) or Q-I-S (5G7-N19Q).

Example 14

Stability of Anti-CD19 Monoclonal Antibodies by Fluorescence Spectroscopy

The stability of anti-CD19 monoclonal antibodies were compared by measuring the midpoint of chemical denaturation by fluorescence spectroscopy.

Fluorescence measurements of chemical denaturation were performed on a SPEX Fluorolog 3.22 with a Micromax plate reader (SPEX, Edison, N.J.). The measurements were performed on antibody samples that had been left for 24 hours to equilibrate in 16 different concentrations of guanidinium hydrochloride in PBS buffer. The measurements were made in black, low volume, non-binding surface 384-well plates (Corning, Acton, Mass.) and required 2 μM of antibody in a well volume of 12 μL. Fluorescence was excited at 280 nm and the emission spectra were measured between 300 and 400 nm. The scan speed was 1 second per nm and slits were set to 5 nm bandpass. A buffer blank was performed using PBS and automatically subtracted from the data. The data is shown in Table 3.

TABLE 3

Fluorescence stability of anti-CD19 antibodies

| Clone | Unfolding Midpoint (M) | Aggregation Peak (M) |
|---|---|---|
| 21D4 | 3.01 | |
| 21D4a | 2.97 | |
| 5G7 | 2.91 | |
| 5G7 IgG4 | 2.63 | |
| 27F3 | 2.77 | |
| 13F1 IgG4 | 2.58 | 2.29 |
| 46E8 | 2.43 | 2.16 |
| 47G4 | 1.68 | |

Example 15

Treatment of In Vivo B Cell Raji Tumors Using Anti-CD19 Antibodies

In this Example, SCID mice implanted with cancerous B cell tumors are treated in vivo with either naked anti-CD19 antibodies or toxin-conjugated anti-CD19 antibodies to examine the in vivo effect of the antibodies on tumor growth.

Toxin-conjugated anti-CD19 antibodies were prepared as described above. Severe combined immune deficient (SCID) mice, which lack functional B and T lymphocytes were used to study B-cell malignancies. Cells from the Raji B tumor cell line were injected subcutaneously. The mice were treated with 30 mg/kg antibody or 0.3 μmole/kg (toxin) antibody-toxin conjugate. An isotype control antibody or formulation buffer was used as a negative control. The animals were dosed by intraperitoneal injection with approximately 200 μl of PBS containing antibody or vehicle. The antibody was either injected as a single dose (SD) on day 0 or as a repeat dose (RD) on days 0, 7 and 14. The mice were monitored daily for tumor growth using an electronic caliper; the tumors were measured three dimensionally (height×width×length/2) and tumor volume was calculated. Mice were euthanized when the tumors reached tumor end point (2000 mm³) or show greater than 20% weight loss. The results are shown in FIG. 32. In each case, the anti-CD19 antibody exhibiting smaller tumor volumes in comparison to the negative controls, with the toxin-conjugate antibodies showing smaller tumor volumes than treatment with naked antibody.

The change in body weight was also measured and calculated as percent change in weight. The results are shown in FIG. 33. The results showed a net decrease change in body weight with the toxin-conjugate antibodies and net increase in weight with either vehicle or naked antibodies.

Example 16

B cell Studies in Cynomolgus Monkeys

In this example, cynomolgus monkeys were injected intravenously with either parental anti-CD19 antibody or nonfucosylated (nf) anti-CD19 antibodies. Absolute leukocyte counts and leukocyte subsets were determined following dosing and compared to pre-dose values.

Blood samples taken from cynomolgus monkeys were stained with either parental CD19 antibody or nf anti-CD19 antibody and analyzed by FACS using standard methods. B-cells from all monkeys included in the study stained positive with both parental and nf anti-CD19 antibodies. Two males and two female monkeys were included in each group. Blood samples were taken at day −7 and pre-dosing. A slow bolus intravenous injection in a saphenous vein was performed and the animals were dosed with 1 mg/kg of parental or nf anti-CD19 antibody. Blood samples were taken 24 hrs, 48 hrs, 72 hrs, and days 7, 14, 21 and 28 post dosing. Blood samples were taken for PK determination, hematology and for flow cytometry. At each time point, the following cell surface antigens were monitored from blood; CD2+/CD20+ (all lymphocytes), CD20+ (3-lymphocytes), CD3+ (T-lymphocytes), CD3+/CD4+ (1-helper lymphocytes), CD3+/CD8+ (T-cytotoxic lymphocytes), CD3−/CD16+ (NK cells), CD3−/CD14+ (monocytes).

FIG. 34 shows the change in the number of CD20 positive cells when compared to the average day −7 and pre-dose values. While parental anti-CD19 antibody induced a 55% decrease in the number of CD20 positive B-cells after 24 hours, the non fucosylated antibody produced a more profound inhibition dropping the B-cell counts by approximately 90%. In the nf anti-CD19 group, the B-cell counts remained at this level at days, 2, 3 and day 7 post treatment while the parental antibody appears to begin to return back to baseline. FIG. 35 shows the % change from baseline for CD20 positive cells for each of the individual monkeys. All four monkeys treated with nf anti-CD19 antibody showed a more significant drop in the % of CD20 positive cells when compared to parental anti-CD19 antibody. Together these data imply that the nf anti-CD19 antibody is more efficacious at depleting circulating B-cells when compared to the parental antibody.

Example 17

Immunohistochemistry Studies of Anti-CD19 Antibodies

To assess the tissue binding profiles of HuMab anti-CD19, FITC conjugated 21D4 (21D4-FITC, F:P=4) and nonfucosylated 21D4 (nf21D4) (nf21D4-FITC, F:P=3) were examined in a panel of normal (non-neoplastic) human tissues, including spleen, tonsil, small intestine, cerebellum, cerebrum, heart, liver, lung, and kidney (1~2 sample/each), as well as B cell neoplasms, including chronic lymphocytic leukemia, follicular lymphoma, marginal zone lymphoma, mantle cell lymphoma, and diffuse large B cell lymphoma (1~2 sample/each). Nonfucosylated 21D4 antibodies were prepared as described above. FITC conjugated Hu-IgG$_1$ (Hu-IgG$_1$-FITC) was used as isotype control antibody.

Snap frozen and OCT embedded normal and lymphoma tissues were purchased from Cooperative Human Tissue Network (Philadelphia, Pa.) or National Disease Research Institute (Philadelphia, Pa.). Cryostat sections at 5 µm were fixed with acetone for 10 min at room temperature, and stored at −80° C. until use. Indirect peroxidase immunostaining using EnVision+System (Dako. Carpinteria, Calif.) was performed following our routine protocol. Briefly, slides were washed with PBS (Sigma, St. Louis, Mo.) twice, and then incubated with peroxidase block supplied in Dako EnVision+System for 10 minutes. After two washes with PBS, slides were incubated with Dako protein block supplemented with 1% human gamma globulins and 1 mg/ml of heat aggregated human IgG for 20 min to block the non-specific binding sites. Subsequently, primary antibodies (21D4-FITC and nf21D4-FITC at 0.4, or 2 µg/ml) or isotype control (Hu-IgG1-FITC at 0.4 or 2 µg/ml), were applied onto sections and incubated for 1 hr. Following three washes with PBS, slides were incubated with mouse anti-FITC antibody (20 µg/ml) for 30 min. After another three washes with PBS, the slides were incubated with the peroxidase-conjugated anti-mouse IgG polymer supplied in the Dako EnVision+System for 30 min. Finally, slides were washed as above and reacted with DAB substrate-chromogen solution supplied in the Dako EnVision+System for 6 min. Slides were then washed with deionized water, counterstained with Mayer's hematoxylin (Dako), dehydrated, cleared and coverslipped with Permount (Fischer Scientific, Fair Lawn, N.J.) following routine histological procedure.

Specific staining with both 21D4-FITC and nf21D4-FITC was observed in lymphoid or lymphoid-rich tissues (spleen, tonsil and small intestine) and lymphoma tissues. In spleen and tonsil, strong specific staining was primarily distributed in the B cell regions, i.e. lymphatic nodules of the spleen, mantle zone and germinal center of the tonsil. In small intestine, strong specific immunoreactivity was mainly localized in Peyer's patch or lymphoid aggregates, as well as weak to strong staining in diffuse lymphocytes in lamina propria of the mucosa. Strong staining was also displayed in tumor cells of follicular lymphoma and marginal zone lymphoma, as well as moderate to strong staining in chronic lymphocytic leukemia, diffuse large B cell lymphoma, and mantle cell lymphoma.

In normal cerebellum, cerebrum, heart, liver, lung, and kidney tissues, no meaningful staining was observed when stained with either 21D4-FITC or nf21D4-FITC except some staining in focal lymphoid cells or aggregates in lung and kidney tissues. In addition, these tissues were stained at higher concentrations up to 10 µg/ml. Similarly, no specific staining was observed as compared with isotype control antibody.

Comparisons of 21D4-FITC and nf21D4-FITC displayed similar staining patterns in all tissues. The specific staining was saturated or close to saturated at 0.4 µg/ml. However, the staining intensity by 21D4-FITC is about 0.5-1 grade stronger than that by nf21D4-FITC. This maybe partially due to higher F:P ratio of 21D4-FITC (4 vs. 3).

Example 18

Assessment of Cell Killing of an Anti-CD19 Antibody

In this example, anti-CD19 monoclonal antibodies alone or conjugated to a toxin were tested for the ability to kill CD19+ cell lines in a thymidine incorporation assay.

An anti-CD19 monoclonal antibody was conjugated to a toxin via a linker, such as a peptidyl, hydrazone or disulfide linker. The CD19+ expressing Raji or SU-DH-6 cell lines were seeded at 1×10$^4$ cells/well. Either anti-CD19 antibody alone or an anti-CD19 antibody-toxin conjugate was added to the wells at a starting concentration of 30 nM and titrated down at 1:3 serial dilutions for 8 dilutions. An isotype control antibody that is non-specific for CD19 was used as a negative control. Plates were allowed to incubate for 69 hours. The plates were then pulsed with 0.5 µCi of $^3$H-thymidine for 24 hours, harvested and read in a Top Count Scintillation Counter (Packard Instruments, Meriden, Conn.). The results are shown in FIG. 36 along with the EC50 values. FIG. 36A shows naked antibody on Raji cells. FIG. 36B shows naked antibody on SU-DHL-6 cells. FIG. 36C shows toxin-conjugated anti-CD19 antibody on SU-DHL-6 cells. This data demonstrates that the anti-CD19 antibody 21D4 binds to and kills Raji B-cell tumor cells and has an unexpectedly high level of cell killing on SU-DHL-6 cells.

Example 19

B-Cell Depletion Studies

To determine if the anti-CD19 antibodies were capable of depleting B-cells, a whole blood B-cell depletion assay was set up.

Human whole blood was purchased from AllCells Inc. (Berkeley, Calif.) and delivered the same day at room temperature. Two ml of whole blood was incubated in the absence or presence of 1-30 mg/ml of the indicated antibodies, or PBS as the untreated group. The blood-antibody mixture was incubated overnight at 37° C. with 5% $CO_2$. On the day of the experiment, the blood was lysed twice with RBC lysis buffer at 1:10 ratio by incubating for 10 minutes followed by centrifugation. After the second spin, the cell pellets were washed once with FACS buffer (PBS plus Calcium and Magnesium with 2% FBS and 20% versene), and followed by FACS staining with anti-CD3 antibody (Becton Dickinson catalog #555332) as the T-Cell makers and anti-CD22 antibody (Becton Dickinson catalog #340708) as a B-cell makers using standard Flow cytometry protocols. Cells were incubated on ice for 20 min prior to the final washes and resuspended in 5 mg/ml propidium iodide solution (Sigma cat# P4864) in FACS buffer. Data was collected by flow cytometry using a FASCalibur system and CellQuest software by Becton Dickinson, and analyzed via FlowJo software using lymphocyte size gating. Percent change was calculated by determining the % positive Bells in the non-treated group minus the % positive B-cells in the antibody treated group divided by % positive B-cells in the non treated group times 100. The results are shown in Table 4. From a healthy blood donor, 8.7% B-cells remained in the blood following an overnight incubation (no antibody). Incubating whole blood with 30 mg/ml of positive control Rituxan led to a 46% depletion in the number of B-cells when compared to the untreated, no antibody group. The group treated with non-fucosylated (nf) anti-CD19 antibody had a pronounced effect on B-cell depletion, inhibiting B-cells by ~40%. Parental antibody had a modest effect on B-cell counts.

TABLE 4

B-cell depletion from whole blood

| Sample | % Positive (CD22) | % Change |
|---|---|---|
| No antibody | 8.7 | — |
| Isotype control | 7.5 | 14.2 |
| Rituxan | 4.7 | 46.3 |
| Parental anti-CD19 mAb | 7.0 | 20.0 |
| Nf anti-CD19 mAb | 5.2 | 40.5 |

SUMMARY OF SEQUENCE LISTING

| SEQ ID NO: | SEQUENCE |
|---|---|
| 1 | $V_H$ a.a. 21D4 & 21D4a |
| 2 | $V_H$ a.a. 47G4 |
| 3 | $V_H$ a.a. 27F3 |
| 4 | $V_H$ a.a. 3C10 |
| 5 | $V_H$ a.a. 5G7 |
| 6 | $V_H$ a.a. 13F1 |
| 7 | $V_H$ a.a. 46E8 |
| 8 | $V_K$ a.a. 21D4 |
| 9 | $V_K$ a.a. 21D4a |
| 10 | $V_K$ a.a. 47G4 |
| 11 | $V_K$ a.a. 27F3 |
| 12 | $V_K$ a.a. 3C10 |
| 13 | $V_K$ a.a. 5G7 |
| 14 | $V_K$ a.a. 13F1 |
| 15 | $V_K$ a.a. 46E8 |
| 16 | $V_H$ CDR1 a.a. 21D4 & 21D4a |
| 17 | $V_H$ CDR1 a.a. 47G4 |
| 18 | $V_H$ CDR1 a.a. 27F3 |
| 19 | $V_H$ CDR1 a.a. 3C10 |
| 20 | $V_H$ CDR1 a.a. 5G7 |
| 21 | $V_H$ CDR1 a.a. 13F1 |
| 22 | $V_H$ CDR1 a.a. 46E8 |
| 23 | $V_H$ CDR2 a.a. 21D4 & 21D4a |
| 24 | $V_H$ CDR2 a.a. 47G4 |
| 25 | $V_H$ CDR2 a.a. 27F3 |
| 26 | $V_H$ CDR2 a.a. 3C10 |
| 27 | $V_H$ CDR2 a.a. 5G7 |
| 28 | $V_H$ CDR2 a.a. 13F1 |
| 29 | $V_H$ CDR2 a.a. 46E8 |
| 30 | $V_H$ CDR3 a.a. 21D4 & 21D4a |
| 31 | $V_H$ CDR3 a.a. 47G4 |
| 32 | $V_H$ CDR3 a.a. 27F3 |
| 33 | $V_H$ CDR3 a.a. 3C10 |
| 34 | $V_H$ CDR3 a.a. 5G7 |
| 35 | $V_H$ CDR3 a.a. 13F1 |
| 36 | $V_H$ CDR3 a.a. 46E8 |
| 37 | $V_K$ CDR1 a.a. 21D4 & 21D4a |
| 38 | $V_K$ CDR1 a.a. 47G4 |
| 39 | $V_K$ CDR1 a.a. 27F3 |
| 40 | $V_K$ CDR1 a.a. 3C10 |
| 41 | $V_K$ CDR1 a.a. 5G7 |
| 42 | $V_K$ CDR1 a.a. 13F1 |
| 43 | $V_K$ CDR1 a.a. 46E8 |
| 44 | $V_K$ CDR2 a.a. 21D4 & 21D4a |
| 45 | $V_K$ CDR2 a.a. 47G4 |
| 46 | $V_K$ CDR2 a.a. 27F3 |
| 47 | $V_K$ CDR2 a.a. 3C10 |
| 48 | $V_K$ CDR2 a.a. 5G7 |
| 49 | $V_K$ CDR2 a.a. 13F1 |
| 50 | $V_K$ CDR2 a.a. 46E8 |
| 51 | $V_K$ CDR3 a.a. 21D4 |
| 52 | $V_K$ CDR3 a.a. 21D4a |
| 53 | $V_K$ CDR3 a.a. 47G4 |
| 54 | $V_K$ CDR3 a.a. 27F3 |
| 55 | $V_K$ CDR3 a.a. 3C10 |
| 56 | $V_K$ CDR3 a.a. 5G7 |
| 57 | $V_K$ CDR3 a.a. 13F1 |
| 58 | $V_K$ CDR3 a.a. 46E8 |
| 59 | $V_H$ n.t. 21D4 & 21D4a |
| 60 | $V_H$ n.t. 47G4 |
| 61 | $V_H$ n.t. 27F3 |
| 62 | $V_H$ n.t. 3C10 |
| 63 | $V_H$ n.t. 5G7 |
| 64 | $V_H$ n.t. 13F1 |
| 65 | $V_H$ n.t. 46E8 |
| 66 | $V_K$ n.t 21D4 |
| 67 | $V_K$ n.t. 21D4a |
| 68 | $V_K$ n.t 47G4 |
| 69 | $V_K$ n.t. 27F3 |
| 70 | $V_K$ n.t. 3C10 |
| 71 | $V_K$ n.t. 5G7 |
| 72 | $V_K$ n.t. 13F1 |
| 73 | $V_K$ n.t. 46E8 |
| 74 | VH 5-51 germline a.a. |
| 75 | VH 1-69 germline a.a. |
| 76 | VK L18 germline a.a. |
| 77 | VK A27 germline a.a. |
| 78 | VK L15 germline a.a. |
| 79 | CD19 a.a. |
| 80 | JH4b germline |
| 81 | JH5b germline |
| 82 | JH6b germline |
| 83 | JH6b germline |
| 84 | JK2 germline |
| 85 | JK3 germline |
| 86 | JK1 germline |
| 87 | JK2 germline |

What is claimed is:

1. A monoclonal antibody, or an antigen-binding portion thereof, which binds specifically to CD19, wherein the antibody or antigen-binding portion thereof comprises:
   (a) a heavy chain CDR1 comprising amino acids having the sequence set forth in SEQ ID NO: 16; a heavy chain CDR2 comprising amino acids having the sequence set forth in SEQ ID NO: 23; a heavy chain CDR3 comprising amino acids having the sequence set forth in SEQ ID NO: 30; a light chain CDR1 comprising amino acids having the sequence set forth in SEQ ID NO: 37; a light chain CDR2 comprising amino acids having the sequence set forth in SEQ ID NO: 44; and a light chain CDR3 comprising amino acids having the sequence set forth in SEQ ID NO: 51; or
   (b) a heavy chain CDR1 comprising acids having the sequence set forth in SEQ ID NO: 16; a heavy chain CDR2 comprising amino acids having the sequence set forth in SEQ ID NO: 23; a heavy chain CDR3 comprising amino acids having the sequence set forth in SEQ ID NO: 30; a light chain CDR1 comprising amino acids having the sequence set forth in SEQ ID NO: 37; a light chain CDR2 comprising amino acids having the sequence set forth in SEQ ID NO: 44; and a light chain CDR3 comprising amino acids having the sequence set forth in SEQ ID NO: 52.

2. A monoclonal antibody, or an antigen-binding portion thereof, which binds specifically to CD19, wherein the antibody or antigen-binding portion thereof comprises:
   (a) a heavy chain variable region comprising amino acids having the sequence set forth in SEQ ID NO: 1 and a light chain variable region comprising amino acids having the sequence set forth in SEQ ID NO: 8; or
   (b) a heavy chain variable region comprising amino acids having the sequence set forth in SEQ ID NO: 1 and a light chain variable region comprising amino acids having the sequence set forth in SEQ ID NO: 9.

3. The monoclonal antibody or antigen-binding portion thereof of claim 1 or 2, which is nonfucosylated.

4. The monoclonal antibody or antigen-binding portion thereof of claim 1 or 2, which binds to human CD19 with a $K_D$ of $5 \times 10^{-8}$ M or less.

5. The monoclonal antibody or antigen-binding portion thereof of claim 1 or 2, which binds to human CD19 with a $K_D$ of $5 \times 10^{-9}$ M or less.

6. The monoclonal antibody or antigen-binding portion thereof of claim 1 or 2, which has thermostability temperature greater than 65° C.

7. The monoclonal antibody or antigen-binding portion thereof of claim 1 or 2, wherein the CD19 is human CD19, which is a polypeptide comprising amino acids having the sequence set forth in SEQ ID NO: 79.

8. The monoclonal antibody or antigen-binding portion thereof of claim 1 or 2, which comprises a heavy chain variable region that is the product of a human $V_H 5$-51 or $V_H 1$-69 gene.

9. The monoclonal antibody or antigen-binding portion thereof of claim 1 or 2, which comprises a light chain variable region that is the product of a human $V_K L18$, $V_K A27$ or $V_K L15$ gene.

10. The monoclonal antibody or antigen-binding portion thereof of claim 9, further comprising a heavy chain variable region that is the product of a human $V_H 5$-51 or $V_H 1$-69 gene.

11. The monoclonal antibody or antigen-binding portion thereof of claim 2, comprising:
   (a) a heavy chain variable region comprising amino acids having the sequence set forth in SEQ ID NO: 1; and
   (b) a light chain variable region comprising amino acids having the sequence set forth in SEQ ID NO: 8.

12. The monoclonal antibody or antigen-binding portion thereof of claim 2, comprising:
   (a) a heavy chain variable region comprising amino acids having the sequence set forth in SEQ ID NO: 1; and
   (b) a light chain variable region comprising amino acids having the sequence set forth in SEQ ID NO: 9.

13. A composition comprising the monoclonal antibody or antigen-binding portion thereof of claim 1 or 2, and a pharmaceutically acceptable carrier.

14. An immunoconjugate comprising the monoclonal antibody or antigen-binding portion thereof of claim 1 or 2, linked to a therapeutic agent.

15. The immunoconjugate of claim 14, wherein the therapeutic agent is a cytotoxin or a radioactive isotope.

16. A composition comprising the immunoconjugate of claim 14 and a pharmaceutically acceptable carrier.

17. The monoclonal antibody or antigen-binding portion thereof of claim 1 or 2, which binds to Raji (ATCC Accession Number CCL-86) and Daudi (ATCC Accession Number CCL-213) B-cell tumor cells.

18. The monoclonal antibody or antigen-binding portion thereof of claim 1 or 2, which is a human antibody or portion thereof.

19. The monoclonal antibody or antigen-binding portion thereof of claim 1 or 2, wherein the antibody is, or the antigen-binding portion thereof is from, a full-length antibody of an IgG1 or IgG4 isotype.

20. The monoclonal antibody or antigen-binding portion thereof of claim 1 or 2, wherein the antibody or antigen-binding portion is a single chain antibody.

* * * * *

UNITED STATES PATENT AND TRADEMARK OFFICE
CERTIFICATE OF CORRECTION

| | | |
|---|---|---|
| PATENT NO. | : 8,097,703 B2 | Page 1 of 1 |
| APPLICATION NO. | : 11/917750 | |
| DATED | : January 17, 2012 | |
| INVENTOR(S) | : Chetana Rao-Naik et al. | |

It is certified that error appears in the above-identified patent and that said Letters Patent is hereby corrected as shown below:

In the Claims:

Claim 1, col. 115, line 65, after "comprising" insert -- amino --.

Signed and Sealed this
Second Day of October, 2012

David J. Kappos
*Director of the United States Patent and Trademark Office*